(12) United States Patent
Liu et al.

(10) Patent No.: US 10,004,398 B2
(45) Date of Patent: Jun. 26, 2018

(54) DEVICE FOR DETERMINING A CONDITION OF AN ORGAN AND METHOD OF OPERATING THE SAME

(71) Applicants: Nanyang Technological University, Singapore (SG); Singapore Health Services Pte Ltd, Singapore (SG)

(72) Inventors: Quan Liu, Singapore (SG); Roger Beuerman, Singapore (SG); Shuo Chen, Singapore (SG)

(73) Assignees: NANYANG TECHNOLOGICAL UNIVERSITY, Singapore (SG); SINGAPORE HEALTH SERVICES PTE LTD, Singapore (SG)

( * ) Notice: Subject to any disclaimer, the term of this patent is extended or adjusted under 35 U.S.C. 154(b) by 0 days. days.

(21) Appl. No.: 15/111,091

(22) PCT Filed: Dec. 16, 2014

(86) PCT No.: PCT/SG2014/000598
§ 371 (c)(1),
(2) Date: Jul. 12, 2016

(87) PCT Pub. No.: WO2015/105457
PCT Pub. Date: Jul. 16, 2015

(65) Prior Publication Data
US 2016/0331230 A1 Nov. 17, 2016

Related U.S. Application Data

(60) Provisional application No. 61/926,518, filed on Jan. 13, 2014.

(51) Int. Cl.
*A61B 3/14* (2006.01)
*A61B 3/135* (2006.01)
(Continued)

(52) U.S. Cl.
CPC ............ *A61B 3/135* (2013.01); *A61B 3/0025* (2013.01); *A61B 3/0075* (2013.01); *A61B 3/14* (2013.01);
(Continued)

(58) Field of Classification Search
CPC ......... A61B 3/10; A61B 3/13; A61B 5/14532; A61B 5/0066; A61B 5/0205; A61B 5/145;
(Continued)

(56) References Cited

U.S. PATENT DOCUMENTS 6,574,501 B2   6/2003   Lambert et al.
7,039,452 B2   5/2006   McClane et al.
(Continued)

FOREIGN PATENT DOCUMENTS

CN    103598871 A     2/2014
WO    2009/133980 A1  11/2009

OTHER PUBLICATIONS

Avunduk et al., "Comparison of efficacy of topical and oral fluconazole treatment in experimental Aspergillus keratitis," *Current Eye Research* 26(2):113-117, 2003. (6 pages).
(Continued)

*Primary Examiner* — Mahidere Sahle
(74) *Attorney, Agent, or Firm* — Seal IP Law Group LLP

(57) ABSTRACT

In various embodiments, a device for determining a condition of an organ of either a human or an animal may be provided. The device may include a first optical source and a second optical source. The device may also include a detector. The device may additionally include a lens system. The device may further include a switching mechanism configured to switch between an optical examination mode and a Raman mode. The lens system during the optical examination mode may be configured to direct a first light (Continued)

emitted from the first optical source. The lens system during the Raman mode may be configured to direct a second light emitted from the second optical source. The lens systems during the Raman mode may be further configured to direct a third light to the detector.

18 Claims, 33 Drawing Sheets

(51) Int. Cl.
    *A61B 3/00* (2006.01)
    *A61B 5/00* (2006.01)
    *G02B 7/09* (2006.01)
(52) U.S. Cl.
    CPC .......... *A61B 5/0075* (2013.01); *A61B 5/7203* (2013.01); *G02B 7/09* (2013.01); *A61B 2503/40* (2013.01); *A61B 2576/02* (2013.01)
(58) Field of Classification Search
    CPC ..... A61B 5/14507; A61B 5/165; A61B 5/445; A61B 5/4842; A61B 5/0082; A61B 5/02055; G01B 9/02091; G01N 21/65
    USPC .................................................. 351/205–221
    See application file for complete search history.

(56) References Cited

U.S. PATENT DOCUMENTS

| | | | |
|---|---|---|---|
| 8,553,219 B2 | 10/2013 | Patil et al. | |
| 2002/0095257 A1 | 7/2002 | Rosen et al. | |
| 2007/0049809 A1* | 3/2007 | Bechtel | A61B 5/14532 600/316 |
| 2010/0049057 A1 | 2/2010 | Gellerman et al. | |
| 2014/0063495 A1* | 3/2014 | Kimura | G01N 21/65 356/300 |

OTHER PUBLICATIONS

Avunduk et al., "Confocal microscopy of *Aspergillus fumigatus* keratitis," *British Journal of Ophthalmology* 87:409-410, 2003. (3 pages).

Chen et al., "Modified Wiener estimation of diffuse reflectance spectra from RGB values by the synthesis of new colors for tissue measurements," *Journal of Biomedical Optics* 17(3):030501, 2012. (4 pages).

Feng et al., "Gastric cancer detection based on blood plasma surface-enhanced Raman spectroscopy excited by polarized laser light," *Biosensors and Bioelectronics* 26:3167-3174, 2011.

Godavarty et al., "Fluorescence-enhanced optical imaging in large tissue volumes using a gain-modulated ICCD camera," *Physics in Medicine and Biology* 48:1701-1720, 2003. (21 pages).

Hosseini et al., "Non-Invasive Monitoring of Commonly Used Intraocular Drugs Against Endophthalmitis by Raman Spectroscopy," *Lasers in Surgery and Medicine* 32:265-270, 2003.

Kernt et al., "Endophthalmitis: Pathogenesis, clinical presentation, management, and perspectives," *Clinical Ophthalmology* 4:121-135, 2010. (16 pages).

Kuijper et al., "Usefulness of Gram Stain for Diagnosis of Lower Respiratory Tract Infection or Urinary Tract Infection and as an Aid in Guiding Treatment," *European Journal of Clinical Microbiology & Infectious Diseases* 22:228-234, 2003.

Lin et al., "Surface-enhanced Raman scattering spectroscopy for potential noninvasive nasopharyngeal cancer detection," *Journal of Raman Spectroscopy* 43:497-502, 2012.

Patil et al., "Combined Raman spectroscopy and optical coherence tomography device for tissue characterization," *Optics Letters* 33(10):1135-1137, 2008.

Rossi et al., "Raman spectroscopy for differential diagnosis of endophthalmitis and uveitis in rabbit iris in vitro," *Experimental Eye Research* 91:362-368, 2010.

Thomas et al., "Procedure for the computation of hazards from diffusely scattering surfaces under the Z136.1-2000 American National Standard for Safe Use of Lasers," *Journal of Laser Applications* 19(1):46-54, 2007. (10 pages).

Whitcher et al., "Corneal blindness: a global perspective," *Bulletin of the World Health Organization* 79(3):214-221, 2001. (9 pages).

Yeung et al., "Applications of the polymerase chain reaction in clinical ophthalmology," *Canadian Journal of Ophthalmology* 44(1):23-30, 2009.

* cited by examiner

1500 activate a switching mechanism to switch between an optical examination mode and a Raman mode

1502

DEVICE FOR DETERMINING A CONDITION OF AN ORGAN AND METHOD OF OPERATING THE SAME

CROSS-REFERENCE TO RELATED APPLICATION

This application claims the benefit of priority of U.S. patent application No. 61/926,518, filed 13 Jan. 2014, the content of it being hereby incorporated by reference in its entirety for all purposes.

TECHNICAL FIELD

Various aspects of this disclosure relate to devices for determining a condition of an organ of either a human or an animal as well as methods of operating the same.

BACKGROUND

Eye infection is a serious clinical problem, which has a high likelihood to lead to blindness without proper treatment. According to the Bulletin of the World Health Organization, eye infection lead to about 1 million new cases of blindness in Asia alone. One major cause of this serious disease is the infection caused by microorganisms such as bacteria and fungi, which usually occurs after intraocular surgery or simply is induced by a distant infective source in the body. Early diagnosis is critical in the management of this disease. The essential prerequisite for the optimal treatment of eye infection is to identify the microorganism causing infection as each type of microorganism causing eye infection requires a different therapeutic approach. For example, systemic antimicrobial therapy is usually recommended for patients with endogenous endophthalmitis. In this case, the type and extent of the infection needs to be diagnosed to determine potential complications and find underlying systemic cause or risk factors.

The current clinical procedure for identifying the microorganism species causing eye infection includes Gram staining and culture of aqueous and vitreous smear samples taken from the surface of infected eyes, which is typically performed in the pathology or microbiology department. Gram staining empirically differentiates bacterial species into two large groups (Gram-positive and Gram-negative) based on the chemical and physical properties of their cell walls. It is fast and cheap. However, it is not meant to be a definitive tool for diagnosis. For example, it only works for bacteria and not every bacterium can be definitively classified. Culture is considered as the gold standard but this procedure is labor intensive and expensive. The cost for Gram staining and culture can range from about 60 Singapore dollars to about 180 Singapore dollars for material charge alone (excluding labor), not mentioning a much larger cost incurred for disease management if not treated in time and appropriately. It usually takes a few days to culture the microorganisms in smears to get reliable results. Such a long delay in diagnosis could result in the exacerbation of patients' symptoms. The delay may also lead to the optimal time frame for treatment being missed as well as the subsequent rising cost for disease management. In addition, taking smear samples from eyes for culturing is unpleasant and can be challenging in some patients. In addition to Gram staining and culturing, Polymerase Chain Reaction (PCR) is sometimes used to assist diagnosis especially for those species that cannot be cultured but PCR is in general expensive and its false-positive rate is often high.

SUMMARY

In various embodiments, device for determining a condition of an organ of either a human or an animal may be provided. The device may include a first optical source and a second optical source. The device may also include a detector. The device may additionally include a lens system. The device may further include a switching mechanism configured to switch between an optical examination mode and a Raman mode. The lens system during the optical examination mode may be configured to direct a first light emitted from the first optical source. The lens system during the Raman mode may be configured to direct a second light emitted from the second optical source. The lens systems during the Raman mode may be further configured to direct a third light to the detector.

In various embodiments, a method of operating a device for determining a condition of an organ of either a human or an animal. The method may include activating a switching mechanism to switch between an optical examination mode and a Raman mode. During the optical examination mode, a lens system may be configured to direct a first light emitted from a first optical source. During the Raman mode, the lens system may be configured to direct a second light emitted from a second optical source. During the Raman mode, the lens systems may be further configured to direct a third light to the detector.

BRIEF DESCRIPTION OF THE DRAWINGS

The invention will be better understood with reference to the detailed description when considered in conjunction with the non-limiting examples and the accompanying drawings, in which:

FIG. 15 is a schematic illustrating a method of operating a device for determining a condition of an organ of either a human or an animal according to various embodiments.

DETAILED DESCRIPTION

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

It should be understood that the terms "on", "over", "top", "bottom", "down", "side", "back", "left", "right", "front", "lateral", "side", "up", "down" etc., when used in the following description are used for convenience and to aid understanding of relative positions or directions, and not intended to limit the orientation of any device, or structure or any part of any device or structure.

The time consuming and costly culture procedure currently used in clinical practice may warrant the development of a new clinical method, which may be able to rapidly and accurately identify the microorganism causing eye infection. Such a method may assist an ophthalmologist to make appropriate therapeutic strategies in a timely manner. Furthermore, it may be desirable to eliminate the unpleasant step of getting smear samples from the eye for the benefit of patients thus the method to be developed should be able to scan the eye non-invasively. A device for use the such a clinical method may be developed.

Figure 1:
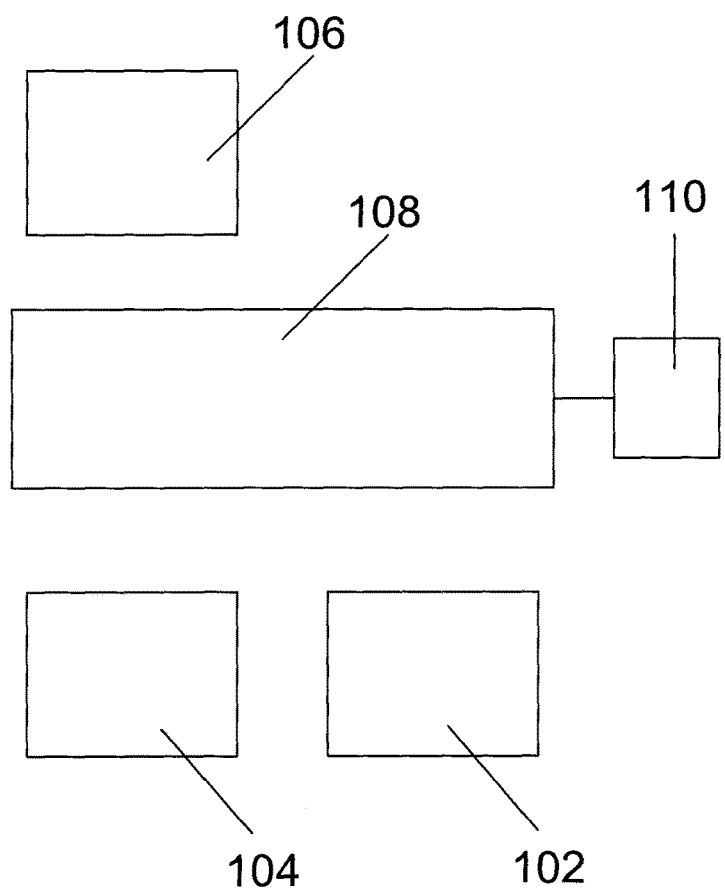
FIG. 1 is a schematic illustrating a device for detecting a condition of an organ of either a human or an animal according to various embodiments.

FIG. 1 is a schematic 100 illustrating a device for detecting a condition of an organ of either a human or an animal according to various embodiments. The device may include a first optical source 102 and a second optical source 104. The device may also include a detector 106. The device may additionally include a lens system 108. The device may further include a switching mechanism 110 configured to switch between an optical examination mode and a Raman mode. The lens system 108 during the optical examination mode may be configured to direct a first light emitted from the first optical source 102. The lens system 108 during the Raman mode may be configured to direct a second light emitted from the second optical source 104. The lens systems 108 during the Raman mode may be further configured to direct a third light to the detector 106.

In other words, the device may be configured to operate in two modes: an optical examination mode and a Raman mode. The device may be configured to emit a first light from a first optical source 102 during the optical examination mode. The device may be configured to emit a second light from a second optical source 104 and detect a third light using the detector 106 during the Raman mode. The two modes may be switched between each other using a switching mechanism 110.

The organ may be an eye. The device may be or may include an opthalmoscope with a Raman module.

In various embodiments, the first optical source 102 may be or may include an incoherent light source. The second optical source 104 may be or may include a laser module.

The third light may be derived or may be based on the second light. The second light emitted by second optical source 104 may incident on the organ, e.g. an eye. The light reflected by the organ may be the third light. Similarly, a first light emitted by the first optical source 102 may incident on the organ to generate or derive a fourth light. The fourth light may be the light reflected by the organ when the first light is incident on the organ.

The second light and the third light may be laser. The second light emitted from the second optical source 104 may have a frequency shift from the third light directed to the detector 106. In other words, the second light may have a first frequency and the third light may have a second frequency. The first frequency and the second frequency may be different.

The first light and the fourth light may be incoherent light. The electromagnetic waves making up the first light may not have a constant phase difference and constant frequency. Similarly, the electromagnetic waves making up the fourth light may not have a constant phase difference and constant frequency. In various alternate embodiments, the first light and the fourth light may instead be coherent light or a laser and the first optical source may be a coherent light source or a laser source, such as in a laser opthalmoscope.

The device may further include an interface portion. The interface portion may be a portion of the slit lamp system in which the first light exits from the device and in which the fourth light enters the device. During the optical examination mode, the lens system 108 may be configured to direct the first light emitted from the first optical source 102 to the interface portion. The first light may be transmitted through the interface portion towards the organ. The fourth light reflected from the organ may be transmitted again through the interface portion. The fourth light may be in an opposing direction to the first light. The device or the lens system 108 may be configured to direct the fourth light to an observer such as an ophthalmologist or a doctor. The observer may thus be able to examine the organ. The device may include an optical examination output portion such as an eye piece. The device or the lens system 108 during the optical examination mode may be further configured to direct the fourth light from the interface portion to the optical examination output portion. The fourth light may be derived from the first light. The fourth light may be reflected by the organ when the first light is incident on the organ. The fourth light may pass through the optical examination output portion to the observer. The observer may examine the organ by looking through or at the optical examination output portion.

During the Raman examination mode, the lens system during the Raman mode may be configured to direct the second light emitted from the second optical source to the interface portion. The second light may be transmitted through the interface portion towards the organ. The third light reflected from the organ may be transmitted again through the interface portion. The third light may be in an opposing direction to the second light. The device or the lens system 108 during the Raman mode may be configured to direct the third light to the detector.

The lens system 108 may include an objective lens for focusing the second light (onto the organ such as the eye). The lens system 108 may further include an actuator for controlling a position of the objective lens. By controlling the objective lens, the actuator may control the focusing of the second light onto the organ. The actuator is a piezoelectric transducer. The actuator may move the objective lens upon application of a voltage to the actuator. The lens system 108 may further include an actuator feedback circuit coupling the detector to the actuator.

In various embodiments, a "circuit" may be understood as any kind of a logic implementing entity, which may be special purpose circuitry or a processor executing software stored in a memory, firmware, or any combination thereof. Thus, in various embodiments, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program, e.g. a computer program using a virtual machine code such as e.g. Java.

The actuator feedback circuit may be configured to receive an output from the detector and further configured to provide a feedback to the actuator based on the output from the detector 106. The actuator feedback circuit may allow for autofocusing. The actuator feedback circuit may be configured to determine a focus index based on the output from the detector 106. The actuator feedback circuit may be configured to determine a plurality of focus indexes based on a plurality of outputs from the detector when the objective lens is moved during calibration. The actuator feedback circuit may be further configured to determine a maximum focus index based on the plurality of focus indexes. The actuator may be configured to move the objective lens during operation until the focus index is at a reference focus index value, i.e. at the calibrated maximum focus index. The focusing of the first light onto the organ may be optimal when the focus index is at the predetermined value.

In other words, the actuator feedback circuit may be configured to determine a focus index based on the output from the detector and may be further configured to provide a feedback based on the determined focus index and a reference focus index. The actuator feedback circuit may be further configured to control the actuator to move the objective lens until the determined focus index is substantially equal to the reference focus index.

The lens system may include a spatial light modulator (SLM) for modulating the second light emitted from the second optical source reflected (to the organ). In other words, the spatial light modulator (SLM) is configured to reflect the second light from the second optical source to the organ. In various alternate embodiments, the lens system may include another dynamic optical element, such as a digital micromirror device, for modulating the second light emitted from the optical source reflected. The spatial light modulator or dynamic optical element may be configured to reflect different intensities of light. The lens system may further include a spatial light modulator feedback circuit (or a dynamic optical element feedback circuit) coupling the detector to the spatial light modulator (or dynamic optical element). In various embodiments, the spatial light modulator feedback circuit (or a dynamic optical element feedback circuit) may be configured, e.g. during operation, to generate a skeletonized line based on a line formed by the second light (on the organ). The spatial light modulator (or dynamic optical element) may be configured to be adjusted based on a feedback, e.g. a feedback voltage, from the spatial light modulator feedback circuit (or a dynamic optical element feedback circuit) until a focus index of each pixel along a subsequent skeletonized line generated reaches a maximum value. The spatial light modulator (or dynamic optical element) may be configured to reflect different intensities of light based on the feedback. In other words, the lens system may include a dynamic optical element for modulating the second light emitted from the second optical source reflected (to the organ). The dynamic optical element may be a spatial light modulator (SLM) or a digital micromirror device. The lens system may further include a dynamic optical element feedback circuit coupling the detector to the dynamic optical element. The dynamic optical element feedback circuit may be configured to generate a skeletonized line based on a line formed by the second light The maximum value may be predetermined, e.g. during a calibration stage. During a calibration stage, the spacial light modulator (or dynamic optical element) may be adjusted and a plurality of focus indexes of each pixel may be determined. The maximum value may be determined based on the plurality of focus indexes of each pixel. During operation, the spatial light modulator (or dynamic optical element) may be adjusted until the maximum value is reached.

The lens system 108 may include one or more beam splitters or dichroic mirrors configured to direct the first light during the optical examination mode and further configured to direct the second light during the Raman mode. In other words, the one or more beam splitters or dichroic mirrors may be used in both modes, i.e. shared for both modes.

The device may further include a processor coupled to the detector 106. The device or lens system 108 may additionally include one or more filters configured to generate one or more narrow-band Raman images from an image (of the organ) captured by the detector 106. The processor may be configured to generate one or more reconstructed Raman images based on the one or more narrow Raman images. Each of the one or more reconstructed images may correspond to one wavelength or one range of wavelengths. The processor may be further configured to generate a Raman spectrum at each pixel based on the one or more reconstructed Raman images. There may be a plurality, e.g. hundreds, of reconstructed images, each corresponding to one wavelength (or wavenumber). The intensity values of these reconstructed images may be concatenated to form a Raman spectrum at each pixel.

The one or more filters may be configured to generate one or more reference narrow-band Raman images from one or more reference images, for instance, during the calibration stage. The one or more reference images may contain or include full spectral information at each pixel (for all pixels). The processor may be further configured to determine a Wiener matrix based on the one or more reference narrow-band Raman images and the one or more reference images. The one or more reference images may be generated based on the one or more reference samples. Each reference sample may include one or more basic (biochemical) components. The processor may be configured to generate the one or more reconstructed Raman images based on the one or more narrow-band Raman images and the Wiener matrix. The processor may be configured to remove fluorescence background from the one or more reconstructed Raman images. The one or more narrow-band Raman images may have a spectral resolution lower than the one or more reconstructed Raman images. The one or more filters may include one or more principal component filters. Additionally or alternatively, the one or more filters may include one or more commercial filters and/or one or more gaussian filters. The one or more filters may be generated from one or more principal components based on or calculated from Raman spectra of the reference portion.

Figure 2:
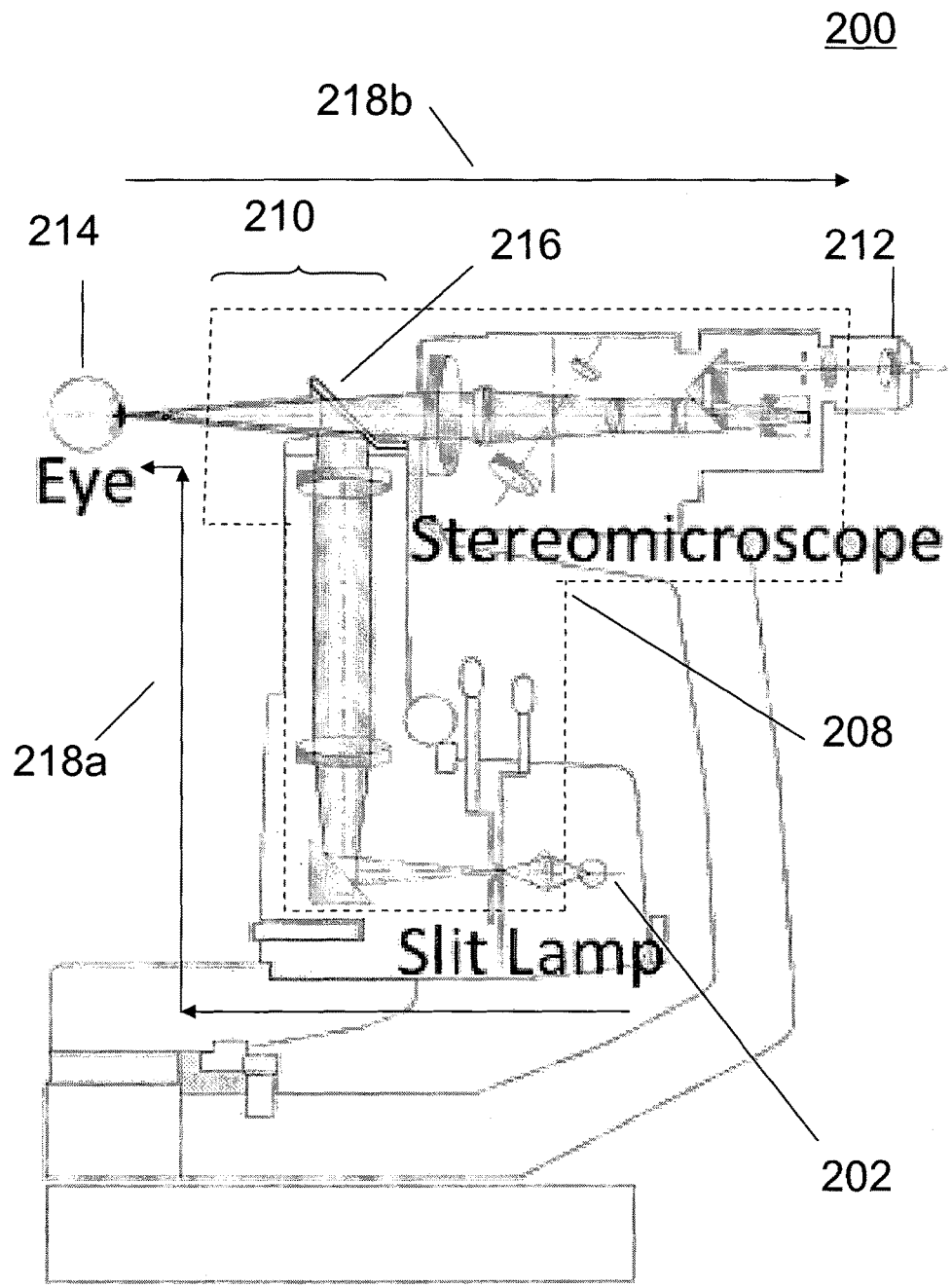
FIG. 2 is a schematic illustrating a slit lamp system according to various embodiments.

FIG. 2 is a schematic 200 illustrating a slit lamp system according to various embodiments. The slit lamp may be configured to determine a condition of an organ such as an eye 214. The slit lamp system may include an optical source 202 and a lens system 208. The lens system may be configured to direct a first light (indicated by 218a) emitted from the first optical source 202 to the eye 214. A fourth light (indicated by 218b) may be reflected from the eye 214.

The slit lamp system may further include an interface portion 210. The interface portion 210 may provide an interface between the slit lamp system and the eye 214. The interface portion 210 may be a portion of the slit lamp system in which the first light exits from the slit lamp system and in which the fourth light enters the slit lamp system. The lens system 208 may be configured to direct the first light emitted from the first optical source 202 to the interface portion 210. The first light may be transmitted through the interface portion 210 towards the eye 214. The fourth light reflected from the organ may be transmitted again through the interface portion 210. The fourth light may be in an opposing direction to the first light. The lens system 208 may be configured to direct the fourth light to an obsever such as an opthalmologist or a doctor. The observer may thus be able to examine the organ. The slit lamp system may include an optical examination output portion 212 such as an eye piece. The lens system 208 may be further configured to direct the fourth light, the fourth light derived from the first light, from the interface portion 210 to the optical examination output portion 212. The fourth light may pass through the optical examination output portion 212 to the observer. The observer may examine the organ by looking through or at the optical examination output portion. The lens system 208 may include one or more beam splitters or dichoric mirrors 216. The lens system 208 may further include other optical components for directing the first light and/or the second light.

Figure 3:
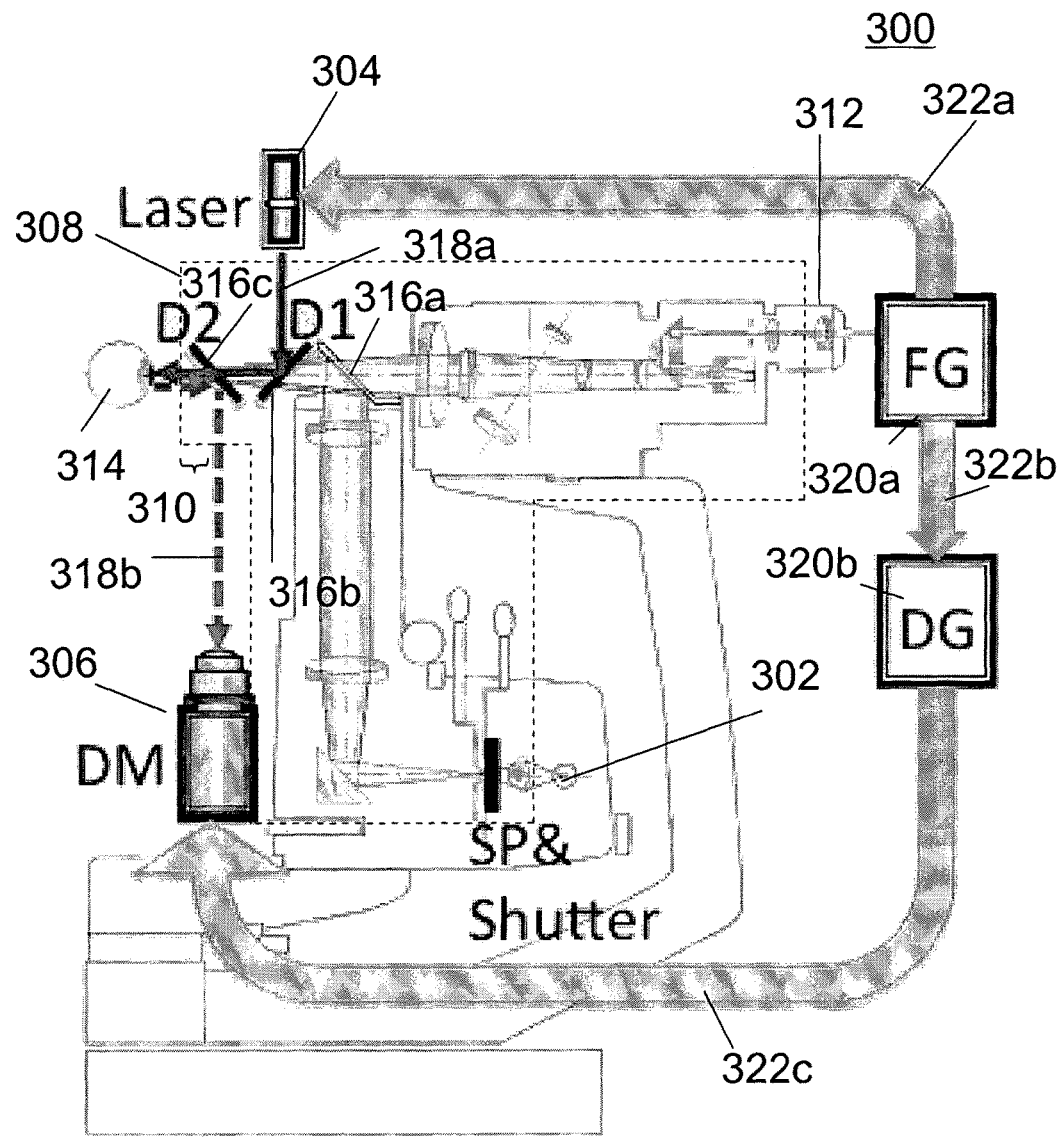
FIG. 3 is a schematic illustrating a device according to various embodiments.

FIG. 3 is a schematic 300 illustrating a device according to various embodiments. The device may be modified from the slit lamp system illustrated in FIG. 2. The device may include the slit lamp system illustrated in FIG. 2. The device may further include a Raman module.

Various embodiments may provide a device for eye scanning based on Raman spectroscopy which aims to rapidly and noninvasively detect Raman spectra from infected cornea and identify the species of microorganisms causing eye infection. The device may include a Raman module in a slit lamp ophthalmoscope so that the scanning procedure and the outlook of the equipment are similar to those in a routine slit lamp examination. The observer or operator may be able to conveniently switch between an optical examination mode (also referred to as slit lamp examination mode) and a Raman mode (using the switching mechanism) while the imaged area (of the eye) remains unchanged. Detected Raman spectra may be processed by a method of multi-variate statistical analysis to identify the species of microorganisms causing eye infection. The outcome of Raman analysis may assist the clinician in diagnosing eye infection. The device may serve as an adjunct tool to provide an alternative to the current clinical procedure for the diagnosis of eye infection in the short term. Based on the result of rapid Raman analysis, the clinician may decide whether the culture step is necessary to reconfirm the diagnosis and/or make appropriate treatment plans early. The wide use of this technique may reduce the need of the expensive and time consuming culture step in the current procedure and cut down the cost of eye infection management.

The device may include a first optical source 302 and a second optical source 304. The device may also include a detector 306. The device may additionally include a lens system 308. The device may further include a switching mechanism configured to switch between an optical examination mode and a Raman mode. The lens system 308 during the optical examination mode may be configured to direct a first light emitted from the first optical source 302. The lens system 308 during the Raman mode may be configured to direct a second light emitted from the second optical source 304. The lens systems 308 during the Raman mode may be further configured to direct a third light to the detector 306.

The operation of the device during the optical examination mode may be similar to the operation of the slit lamp system illustrated in FIG. 2. The device may include an interface portion 310 and an optical examination output portion 312.

The interface portion 310 may be a portion of the device in which the first light exits from the device and in which the fourth light enters the device. The lens system 308 may be configured to direct the first light emitted from the first optical source 302 to the interface portion 310. The first light may be transmitted through the interface portion 310 towards the eye 314. The fourth light reflected from the eye 314 may be transmitted again through the interface portion 310. The lens system 308 may be configured to direct the fourth light to an obsever such as an opthalmologist or a doctor through the optical examination output portion 312. The lens system 308 may be further configured to direct the fourth light, the fourth light derived from the first light, from the interface portion 310 to the optical examination output portion 312.

During the Raman examination mode, the lens system 308 during the Raman mode may be configured to direct the second light (indicated by 318a) emitted from the second optical source to the interface portion 310. The second light may be transmitted through the interface portion towards the eye 314. The third light (indicated by 318b) reflected from the eye 314 may be transmitted again through the interface portion 310. The third light may be in an opposing direction to the second light. The device or the lens system 308 during the Raman mode may be configured to direct the third light to the detector 306. The interface portion 310 may be a portion of the device in which the second light exits from the device and in which the third light enters the device.

The device may further include a function generator 320a and a delay generator 320b. The arrows 322a, b, c may represent the flow of control signals. The function generator 320a may be configured to provide control signal 322a to the second optical source 304 to activate the second optical source 304. The function generator 320b may be configured to provide control signal 322b to the delay generator 320b. The delay generator 320b may be configured to provide control signal 322c to the detector 306 after a predetermined delay from receiving control signal 322b.

The lens system 308 may include one or more beam splitters or dichoric mirrors 316a-c. The one or more beam splitters or dichroic mirrors 316a-c may be configured to direct the first light during the optical examination mode and further configured to direct the second light during the Raman mode. In other words, the one or more beam splitters or dichroic mirrors may be used in both modes, i.e. shared for both modes. The dichroic mirrors 316a-c may be separate mirrors.

The lens system 308 may further include other optical components for directing the first light and/or the second light.

Various embodiments may provide fast and accurate Raman measurements as required by clinical examination. The integration of a Raman module into a slit lamp ophthalmoscope may require careful detailed design to achieve fast and accurate Raman measurements as required by clinical examination which is highly challenging.

For instance, it may not practical to expect a clinician to be able to manually focus laser light onto the area of interest on the cornea surface considering that they are not experts in optical alignment. The fact that the cornea is transparent may make it more difficult to achieve a good focus. Unfortunately, this may be required to get a good Raman signal.

Various embodiments may include an autofocusing method and system developed to eliminate or reduce the need of manual focusing. A red laser adjusted at a small power following exactly the same optical path as the excitation light for Raman excitation may be used to facilitate alignment. The laser spot for alignment, which may be visible to clinicians, may be manually moved vertically along the line illuminated by the slit lamp to help the physician trace the location to be examined by Raman measurements. Once the location of interest is identified, the autofocusing procedure may be started. The procedure may take advantage of the fact that the reflected light intensity increases dramatically when a laser spot crosses a boundary with refractive index mismatch. A computer may control a piezoelectric transducer (PZT) based actuator to move a microscope objective lens to achieve autofocusing.

The same light source for Raman excitation (working at a small power) and detector 306 (e.g. spectrograph and charged coupled device (CCD)) may also be used for alignment to save the extra light source and photodetector for alignment. The disadvantage of this approach may be that the clinician may not be able to see the laser spot as clear as the red laser spot. Only the vertical dimension of the image in this case may represent the spatial dimension that is used to calculate the contrast and spot size. The other dimension (horizontal dimension) may correspond to the spectral dimension and should not be used for the purpose of calculating contrast and spot size.

Another issue may be that a patient's eye may not stay at one fixed position for long, typically only a couple of seconds or shorter. It may be challenging to detect Raman spectra with a decent signal to noise ratio within such a short time frame.

The eye movement problem may be overcome by fast data acquisition, ideally in real time. Within the short data acquisition period, the cornea may be viewed as stationary and the effect of eye movement on Raman spectra may be neglected. To achieve this, a modified Wiener estimation for spectral reconstruction and relevant algorithms may be used to speed up data acquisition. The method of data acquisition using the modified Wiener estimation may be distinguished from most other Raman systems. A spectrograph with much poorer spectral resolution compared to a normal one used in Raman acquisition may be used to improve the signal to noise ratio by providing a larger bandwidth at each wavenumber. Then a modified Wiener estimation may be used to reconstruct Raman spectra at the required spectral resolution rapidly.

The idea of using Raman spectroscopy to identify the microorganisms causing eye infection may be based on the following phenomena. First, bacteria and fungi, which are the two major microorganisms causing infection, may exhibit unique Raman fingerprints. Second, the change in the biochemical composition, and thus the Raman patterns, of ocular tissues induced by eye infection may vary with the microorganism species. This may be a secondary effect compared to the Raman spectra of the microorganism in terms of the diagnostic value. Raman spectroscopy has been recently used for the differential diagnosis of eye infection and uveitis in rabbit iris in vitro and monitoring intraocular drugs against endophthalmitis, which demonstrates the feasibility of using Raman spectroscopy for the in vivo identification of microorganisms causing eye infection.

However, the following requirements may have to be fulfilled in order to perform Raman measurements in the eye in vivo.

1. The excitation power density may be required to be lower than the safety threshold prescribed in International Laser Safety Standards while data acquisition may need to be fast to prevent the motion artifact.

2. There may be a requirement to avoid optical alignment or realignment when switching between the route slit lamp examination mode and Raman mode.

3. Data analysis may need to be fast to provide quick feedback.

The strategies below may be employed to address these requirements one by one.

1. A strategy may be taken to improve the signal to noise ratio in order to achieve the goals of lowering the excitation power density and fast data acquisition. Various filters may be used to remove the sideband in the excitation light and the influence of ambient light on Raman spectra. A lock-in detection scheme using a gain-modulated intensified CCD may be utilized to improve the signal-to-noise ratio.

2. The Raman module may be designed to minimize the changes or modification to the slit lamp system as shown in FIG. 2A. FIG. 2B is a non-limiting example to illustrate one of several options for incorporating the Raman module. A computer code may be developed to automate the operation of switching between the routine slit lamp examination mode and Raman mode. In other words, the switching mechanism may include a processing circuit including a computer algorithmn. A clinician may work in the routine examination mode first to locate the target area. Then the scanner may be switched to Raman mode to take Raman spectra from the area without the need of any further adjustment.

3. An ex vivo study may be carried out to identify optimal Raman bands for differentiating various species of microorganisms. Only selected Raman bands may be involved in clinical data analysis to speed up the diagnosis.

By applying these strategies, a device including a Raman module integrated with a slit lamp system may enable fast and sensitive Raman measurements from the eye 314 without interrupting the routine slit lamp examination procedure. The high sensitivity of Raman measurements to a range of microorganisms causing infection demonstrated previously may help ensure the accuracy of the non-invasive optical diagnosis. With the advance in laser technology and sensitive optical detectors, the cost of optical components in a sensitive Raman system has dropped significantly, which may make it feasible to build a cost-effective Raman module for eye scanning. Due to the nature of non-contacting optical measurements, the device may require minimum maintenance, thus further bringing down the total cost of operating such a system on a regular basis.

The lens system 308 may include an objective lens (not shown in FIG. 3) for focusing the second light (onto the organ such as the eye 314). The lens system 308 may further include an actuator (not shown in FIG. 3) for controlling a position of the objective lens. By controlling the objective lens, the actuator may control the focusing of the second light onto the eye 314. The actuator is a piezoelectric transducer. The actuator may move the objective lens upon application of a voltage to the actuator. The lens system 308 may further include an actuator feedback circuit (not shown in FIG. 3) coupling the detector to the actuator.

The actuator feedback circuit may be configured to receive an output from the detector 306 and further configured to provide a feedback, e.g. a feedback voltage, to the actuator based on the output from the detector 306. The actuator feedback circuit may allow for autofocusing. The actuator feedback circuit may be configured to determine a focus index based on the output from the detector 306. The actuator feedback circuit may be configured to determine a plurality of focus indexes based on a plurality of outputs from the detector when the objective lens is moved during calibration. The actuator feedback circuit may be further configured to determine a maximum focus index based on the plurality of focus indexes. The actuator may be configured to move the objective lens during operation until the focus index is at a reference focus index value, i.e. at the calibrated maximum focus index. The focusing of the first light onto the eye 314 may be optimal when the focus index is at the predetermined value.

In other words, the actuator feedback circuit may be configured to determine a focus index based on the output from the detector 306 and may be further configured to provide a feedback, e.g. a feedback voltage, based on the determined focus index and a reference focus index. The actuator feedback circuit may be further configured to control the actuator to move the objective lens until the determined focus index is substantially equal to the reference focus index.

Figure 4A:
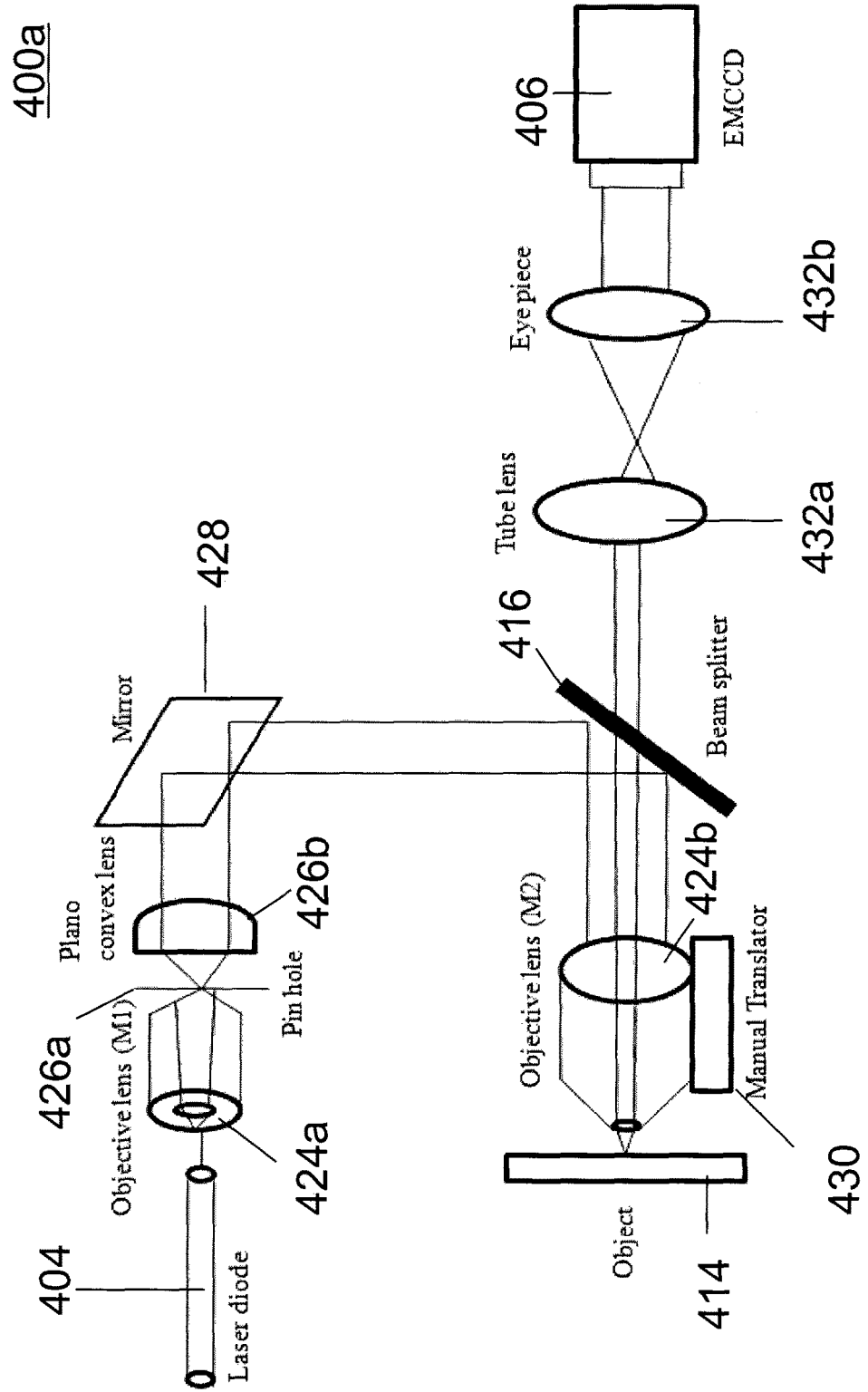
FIG. 4A is a schematic 400a of a setup to illustrate focusing according to various embodiments.
Figure 4B:
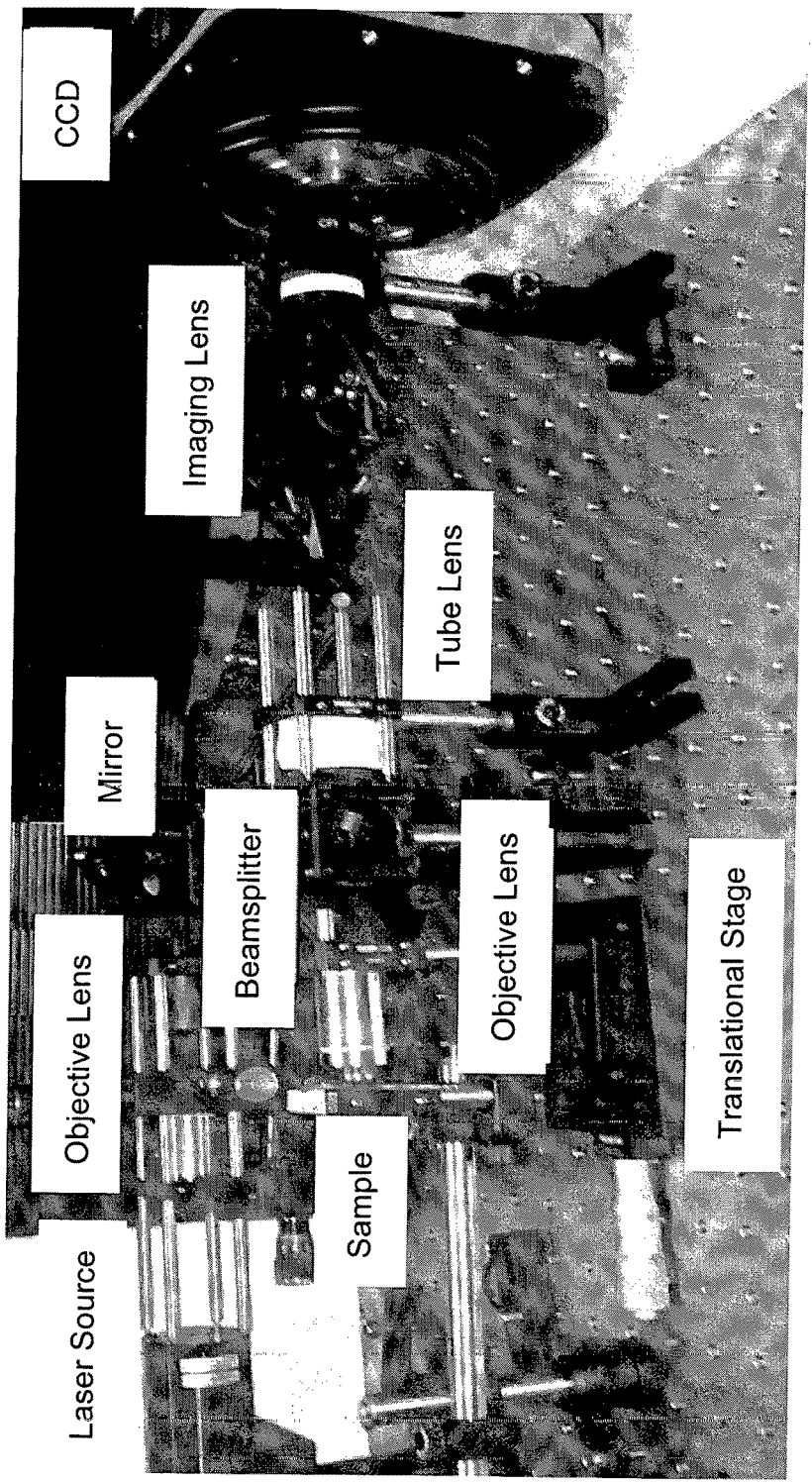
FIG. 4B is an image of the setup illustrated in FIG. 4A according to various embodiments.

FIG. 4A is a schematic 400a of a setup to illustrate focusing according to various embodiments. The device according to various embodiments may include various components of the setup in a similar manner. In various embodiments, references to the setup may include references to the device. FIG. 4B is an image 400b of the setup illustrated in FIG. 4A according to various embodiments.

The auto-focusing option may include two portions 1) hardware components and/or 2) software. The orientation of the experimental setup for focusing the specific area of the sample includes both hardware and software components. The hardware components used for the experimental setup may be illustrated in FIG. 4A. The hardware component may be used to obtain the stack of images and the software may be used to perform the image processing.

The setup may include a laser (or LASER) source 404. The laser source may also be used in the device. LASER is an acronym for light amplification by stimulated emission of radiation. A laser is a component which may be configured to emit light by the principle of stimulated emission. When a particle is hit by the photons it may absorb some energy and may jump to the excited state from the ground state. When returning back to the original position, the particle may emit some of its energy in the form of photons. Lasers may be used in many biomedical and biological applications due to different wavelengths.

The setup may also include a beam splitter 416. The beam splitter 416 may also be included in the device. As the name implies, the beam splitter 416 may split an optical beam into two by allowing a first light to pass through it and a second light to be reflected at substantially 90° (at the point of incidence). The optical beam may be treated as the second light as highlighted earlier. The beam splitter 416 may work in a similar manner to a mirror in transmitting the part of incident light (the second light). One part of the second light may be made to pass through the beam splitter 416 and the rest of the second light may be reflected from the reflecting surface of the beam splitter 416.

The setup and/or device may include one or more objective lens 424a, 424b. For the optical imaging, microscopic objective may play a major role in the determining the image quality and may also interpret the primary image formation process. The primary purpose of objective lens 424b may be to collect the light from the sample or object 414 and to magnify the information and to provide the magnified information to detector 406. Objective lens 424b may come with different degrees of magnification power. The sample or object 414 may be an organ such as an eye but may also be a non-living object for the purposes of experiment. The third light reflected from the object 414 may pass through the beam splitter 416 to the detector 406.

Objective lens 424a, 424b may be characterized by two parameters, namely magnification factor and numerical aperture. The objective lens 424a, 424b may provide information by enlarging the content with a specified range. The magnification factor for objective lens may range from 40× to 100×. The numerical aperture may be defined as the accepted angle of the lens 424a, 424b from which it is determined how the lens 424a, 424b may readily emit or accept light. As numerical aperture increases, the working distance may decrease. The working distance may be defined as the maximum distance between the sample 414 and front part of the lens 424b from which all the information of the sample can be collected and it is defined as sharp focus. The parfocal length may be defined as the distance between the objective mounting position to the sample surface, i.e. the summation of focal length and working distance.

The setup or device may also include a detector such as a charge coupled device (CCD) 406. The detector may include a photographic film. The CCD may include a thin silicon wafer which may be divided into a plurality of small light sensitive areas. Each separate area or square may be referred to as a photosite. Here each photosite may be substantially equivalent to a pixel of the image. Each photosite may include a capacitor which is positively charged. Basically, the CCD is an analog device which may convert light to electrons by photoelectric effect. Since the photosites are positively charged, the electrons, which are negatively charged, may be attracted towards photosites. The particular movement of charges inside the device may provide the output voltage, which may be proportional to the number of photons that are incident on the photosites. However, the analog signal may be converted into digital signals. The CCD may record the video instead of taking the pictures. The cost of the scientific CCD may be expensive because the size is big and only little silicon wafers may fit to design.

Exposure may start at the time the capacitors of the photosites are positively charged and may end by disconnection and opening the shutter of the CCD. The light from the objective lens 424b may be made to pass through the silicon within the CCD. However this may lead to transfer of some electrons from low energy valence band to high energy conduction band. Some of the electrons may be attracted towards the positively charged capacitor, which may allow the capacitor to discharge partially. The amount of discharge may be directly equal or may be proportional to the number of photons incident on the photosite during the exposure time. At or near the end of the exposure, the electrons at each photosite may be amplified and may pass through the analog to digital converter (ADC) device to digitize the signal.

While a piezoelectric transducer (PZT) has not been used in the preliminary experiment, a device including a piezoelectric transducer may be envisioned. A piezoelectric transducer may be a device which converts mechanical movement to electrical energy and electrical energy into mechanical movement. The PZT may include a polarized material. When the electric current passes through the transducer, the polarized material may realign in the different manner compared to an initial alignment, consequently producing a different shape of the material and generating mechanical movement. This process may be called electrostriction.

A fully polarized material such as quartz may generate electric, energy according to the change in dimension of the material. This process may be called piezoelectric effect.

The polarized material may be or may include a ceramic material, which may have a high efficiency to change size and shape. The efficiency of the transducer may be measured by the ratio of output energy to input energy. The efficiency of the transducer may be good when the output energy is greater than the input energy.

The principle of focusing technique may depend on the image spatial resolution. For the digital images, resolution may be dependent on the number of pixels in an image. The spatial resolution is used to find closeness of pixels revolved to create an image. Even if the number of pixels is high, the spatial resolution of the image may not be good. The spatial resolution depends on the clarity of the image.

When the image is in focus, the spatial resolution may be high. Conversely, when the image is out of focus, the spatial resolution may be lower. The determination of the focus position may be widely dependent on the spatial frequency at different planes of each image extracted.

It may be important to align the laser beam straight because even with the slight disturbance, it may lead to misalignment of the images at different distance. The components shown in FIG. 4 are aligned in such way that the laser beam travels all through the components in the straight direction without any deviation.

The laser beam from the laser diode 404 may be first made to pass through the infinite microscopic objective lens 424a. Without using the microscopic objective 424a in the preliminary setup of the experiment, it was found that the images are not along the same point, i.e. the image obtained was fluctuating along the frame with respect to different distances. The microscopic objective lens 424a (M1) was included to minimize the fluctuation and to make the size of the beam larger. The pinhole 426a and the plano convex lens 426b may be placed in between the objective 424a and the mirror 428 to collimate the forecoming light in order to prevent it from diverging.

Later the beam is reflected from the mirror 428 for the sake of requirement of the experiment. As already mentioned, a beam splitter 416 may be included to split the light into two. The beam splitter 416 may reflect about 50% of light to the microscopic objective 424b (M2) and allow another about 50% of light to pass through in a straight direction (not shown in FIG. 4A). The microscopic objective 424b may play a major role in determining the quality of the image and to trace the focus position. In initial experiment, objective lens 424b is placed on the manual translator 430, which moves the objective lens 424b forward and backward along a direction, e.g. in the z direction, relative to the sample 414. The objective lens 424b may be moved relative to the sample 414 to achieve the best focusing.

The manual translator 430 may have a millimeter range along the main scale and a microns range along the rotating scale. The light from the objective lens 424b M2 may converge at some point when moving out of the lens 424b. The converging distance from the particular point to the front of the lens 424b may be called the working distance of the objective lens 424b. The point, i.e. the focus point, may be related to the working distance of the objective lens 424b. The objective lens used here may be purchased from Thorlabs. Here the microscopic objective used has the magnification factor of 40× with a working distance is about 0.6 mm. The effective focal length of the objective lens 424b is 4.5 mm and parfocal length is about 45.06 mm. The numerical aperture of the objective lens 424b is 0.65.

The reflected light (i.e. third light) from the sample 414 may pass through the beam splitter 416. The reflected light may contain the collected information of the sample and the detector 406 may capture the image. Tube lens 432a and microscopic eye piece lens 432b may be placed between the beam splitter 416 and CCD 406. The purpose of the objective lens 424b is to collect the image of the sample 414 at infinity. The objective lens 424b sends reflected light from the sample 414 as a bundle of parallel lights across to tube lens 432a. The tube lens 432a behaves as a receiver and sender which may center the parallel lights from the lens 424b to the centre part of the detector 406. Microscopic eye piece lens 432b may collect the light from tube lens 432a so that the lights from lens 432b are again substantially parallel. Tube lens 432a may be accompanied with the microscopic eye piece lens 432b for obtaining better results. The main advantage of using the tube lens 432a is that it provides a space between beam splitter 416 and detector 406 so an external optical component like another beam splitter or filter may be included when necessary.

The working distance of the tube lens 432a may vary according to different manufacturers. The tube lens may have a working distance range from about 70 to about 200 mm. The focal distance of the tube lens 432a may be about 200 mm. The tube lens 432a may be placed at a distance from about 70 mm to about 200 mm from the objective lens 424b. When the tube lens 432a is placed at below 70 mm from the objective lens 424b, the resultant image may be affected by aberrations. Conversely, when the tube lens 432a is placed at beyond 200 mm from the objective lens 424b, the scan lens in the tube may be overfilled, which may result in inaccurate results.

The macroscopic eye piece lens 432b may have a different magnification power from tube lens 432a. The main purpose of the macroscopic eye piece lens 432b is magnification. The magnification factor of 10× is used in our experiment. The light reflected from the sample 414 is magnified accordingly and fed to the central part of the detector 406.

The detector 406 may be an Electron Multiplying Charge Coupled Device (EMCCD). The manufacture of the EMCCD used in our study is the Princeton Instruments. ProEM cameras are designed in such a way to overcome the challenges of low-light, high frame rate, and light-starved applications. A ProEM camera may include 512×512 back-illuminated EMCCD and may support both electron multiplication (EM) and traditional readout ports. The images of the sample 414 may be obtained by varying the distance of the sample 414 with the detector 406 at regular intervals.

A focusing technique based on the image spatial resolution may be provided. As discussed earlier, the spatial resolution is a factor which determines how closely the pixels are related to form an image. When the objective lens 424b M2 is in focus position, the image obtained at that position may have a high value of the spatial resolution. When objective lens 424b M2 moves out of the focus position, the spatial resolution of the images obtained may decrease. Consequently, when the image spatial resolution decreases, the high frequency components of the image may also be decreased. The device or setup may be configured to measure the high frequency components for the captured images at each plane and determine an optimal focus.

Generally, the high frequency content is extracted from the full frequency spectrum of the captured image by using a high band pass filter. The external analog filters or the digital filters inside the computer may be used for this purpose. In other words, the filter may be a physical filter or a digital filter.

For each turn, the manual translator 430 may be moved at constant intervals of distance. The stack of images with respect to the change in distance may be captured by the detector 406. With the help of the computer, digital image processing may be carried out for all the images to find the focus index. The focus index may be described as the ratio of the sum of square of the each pixel value of the convoluted image to the square of the sum of the pixel values of the original image. The convoluted image is may be generated by convolution of the image with the high pass filter.

The focus index may be calculated from the formula stated below, $$F(z) = \frac{\sum_x \sum_y [f(x,y) \otimes i_z(x,y)]^2}{[\sum_x \sum_y i_z(x,y)]^2} \quad (1)$$

where x, y are the index of the pixels, $i_z(x,y)$ denotes the value of each pixels, f(x,y) is the value of high pass filter and $\otimes$ operator denotes convolution factor The added advantage of using the digital filters is that using the digital filters may provide a wide number of choices to select the different filters. In the experiment, the kernel integer filters are used for the image processing. The kernel filters are the most used filters for convoluting the image. Kernel filters may provide several options like blurring, edging, sharp detection, smoothening and even more in the field of image processing. Generally, kernel filters may allow both low pass and high pass filtering.

The sample or object 414 may be a glass slide with particles distributed on the glass slide. Each particle is about 10 μm in size. The sample particle on the glass slide may be placed in front of the objective lens 424b (M2). The manual translator 430 may be moved along a line (i.e. one dimensional translation) towards and away from the sample or object 414. The objective lens 424b may be placed as near as possible the sample or object 414 initially but without touching the glass slide. The objective lens is sensitive component and even a small disturbance can cause damage to lens, one should be very careful with moving the objective lens 424b near the sample or object 414. The objective lens 424b may be moved away from the sample or object 414 using the translator 430.

The focus index may be calculated for each image on the detector 406 according the formula. The first image may taken when the objective is placed very near to the sample and the later images may be obtained when moving the objective lens away from the sample which is mounted on the manual translator 430.

Figure 5A:
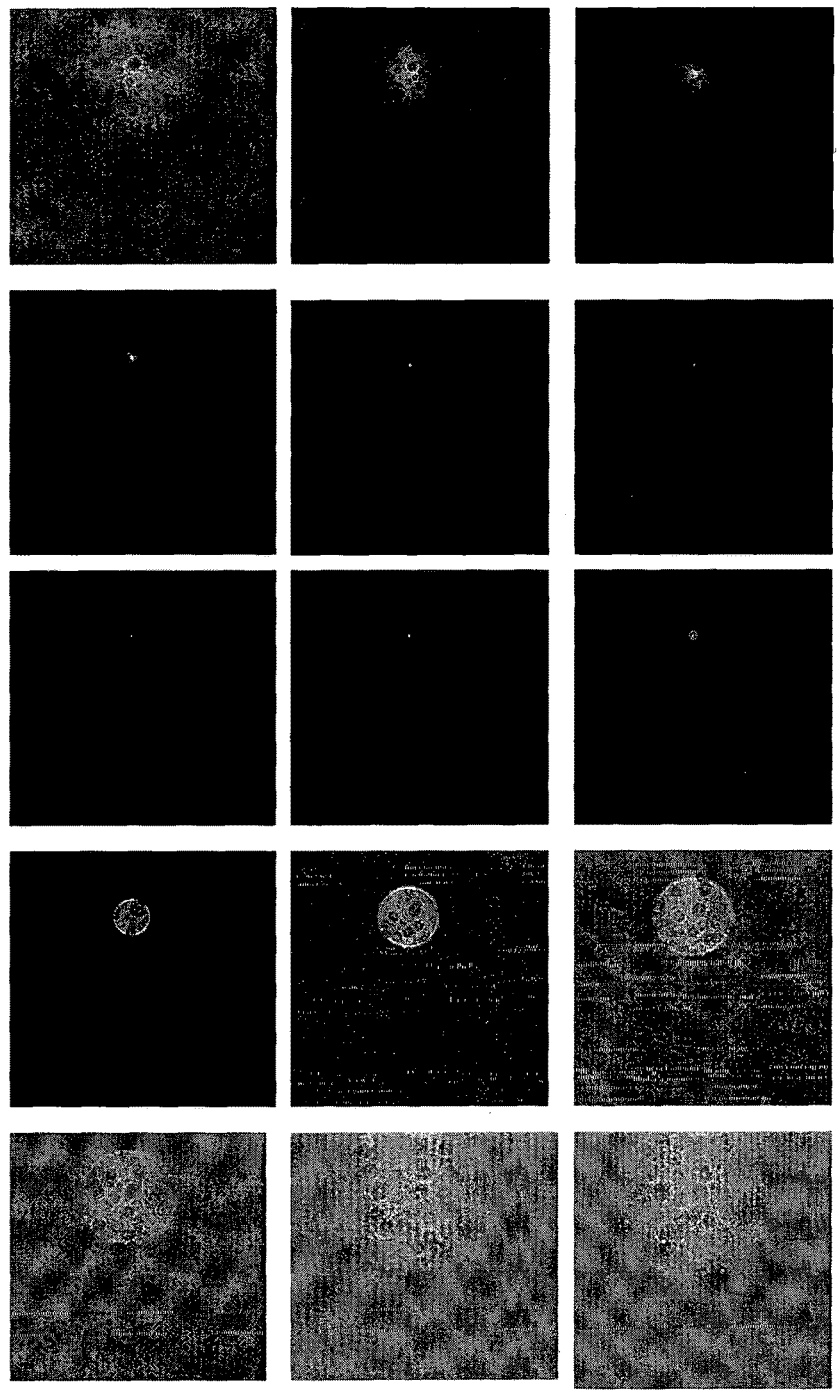
FIG. 5A is a sequence of images obtained at the detector according to various embodiments.

FIG. 5A is a sequence 500a of images obtained at the detector 406 according to various embodiments. The images are obtained by varying distances of the objective lens 424b from sample or object 414 (captured with constant intervals). The images are obtained in the interval of 0.5 microns distance. The resultant images were originally in the tif format and it was converted to bmp file with the help of Image J software. The images obtained was read by the computer and stored in the appropriate space for subsequent use in the program. MATLAB software was used for the image processing and to perform calculations. Any other software like C, C++ may also be used. The advantages of MATLAB may include that the speed is high and hence may result in a less time consuming process. Manual adjustment may be time consuming and automation may increase the speed.

The integer kernel filter may be used as the high pass filter to filter the high frequency content of the images from the full spectrum of the images. The integer filter used here is, $$\begin{matrix} -1 & -2 & -2 \\ -1 & -12 & -1 \\ -1 & -2 & -1 \end{matrix} \quad (2)$$

As discussed, the first image is taken when the objective is placed very near to the sample. The region of interest (ROI), i.e. where the particle is spread vastly on the glass slide, is found on the first image. The objective lens 424b is securely fixed to the translator 430 for reducing errors. The manual translator 430 is moved away from the sample 414. The objective lens 422b is moved away from the sample 414 by moving of the manual translator.

Further images are captured at subsequent constant intervals. The total illumination of the original image is calculated by summing up of all pixel values in each images and the whole sum is squared according to Equation (1). The convoluted image is generated by convoluting the image with the filter in (2).

Figure 5B:
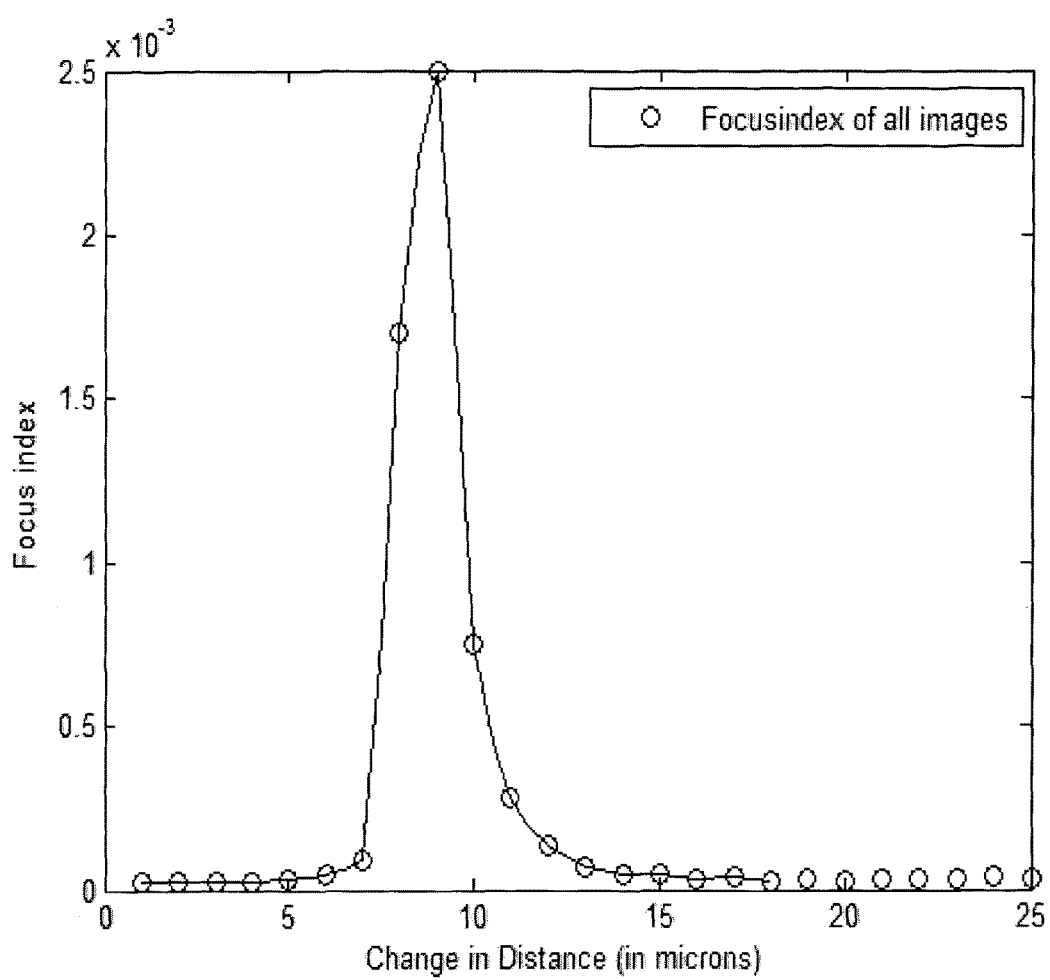
FIG. 5B is a plot of the focus index as a function of distance in microns.

Then the sum of square of all the gray pixels values (for the convoluted image) is calculated. The focus index for each image is then calculated by dividing the numerator, i.e. the square of the sum of the original image, with the denominator, i.e. the sum of the square of the pixel value of the convoluted image. The focus index values may be plotted as a function of the distance of the objective lens 424b from the object 414. FIG. 5B is a plot 500b of the focus index as a function of distance in microns.

A bell shaped curve may be obtained as shown in FIG. 5B. The peak in the curve provides the highest value of the focus index. This value may represent a focus image at the detector 406 when the objective lens 424b is at an optimal distance from the object 414. The high frequency content of the focus image may be high compared to the other images which are out of focus.

The eye is a semi-transparent object which has many layers with different values of refractive index. As such, the experiment has been done on a transparent surface. In summary, a stack of images may be generated at the detector 406 and the focus index of each image may be determined. The highest value of the focus index may be determined from the focus indexes of the images. The image with the highest focus index value may be the focus image. The spatial frequency of each image may correspond to the spatial resolution of the image.

Figure 6:
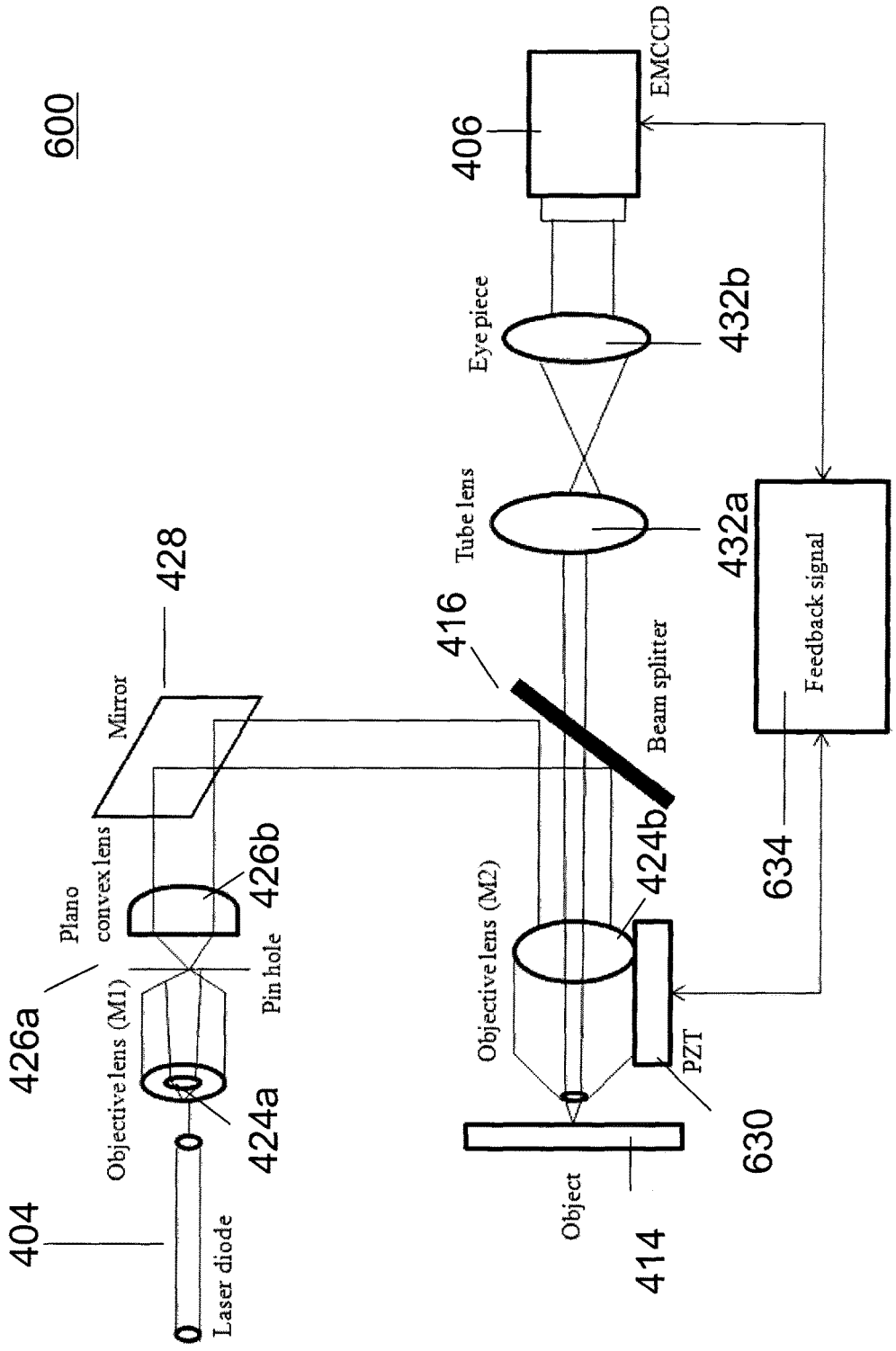
FIG. 6 is a schematic of a setup to illustrate auto-focusing according to various embodiments.

FIG. 6 is a schematic 600 of a setup to illustrate auto-focusing according to various embodiments. The setup may be similar to the setup illustrated in FIG. 4A but with the manual translator replaced by a piezoelectric transducer 630 (such as a lead zirconium titanate (PZT) transducer) and an actuator feedback circuit 634 coupled between the detector 406 and the piezoelectric transducer 630. The device according to various embodiments may include various components of the setup in a similar manner. In various embodiments, references to the setup may include references to the device.

The actuator feedback circuit 634 may be configured to receive an output from the detector 406 and further configured to provide a feedback, e.g. a feedback voltage, to the piezoelectric transducer 630 based on the output from the detector 406. The first calculated focus index for an image may be taken as the reference value (reference focus index). The feedback voltage may be provided to the piezoelectric transducer 630 for an subsequent image based on the focus index of the subsequent image. The feedback voltage may be further based on the reference focus index or the focus index of a preceding image. The piezoelectric transducer 630 may be moved accordingly towards or away from the object 414, e.g. the eye, until the focus index reaches a maximum value, i.e. when the focus image is detected. The actuator feedback circuit 634 may be configured to determine a focus index based on the output from the detector 406 and may be further configured to provide a feedback, e.g. a feedback voltage, based on the determined focus index and a reference focus index.

Figure 7:
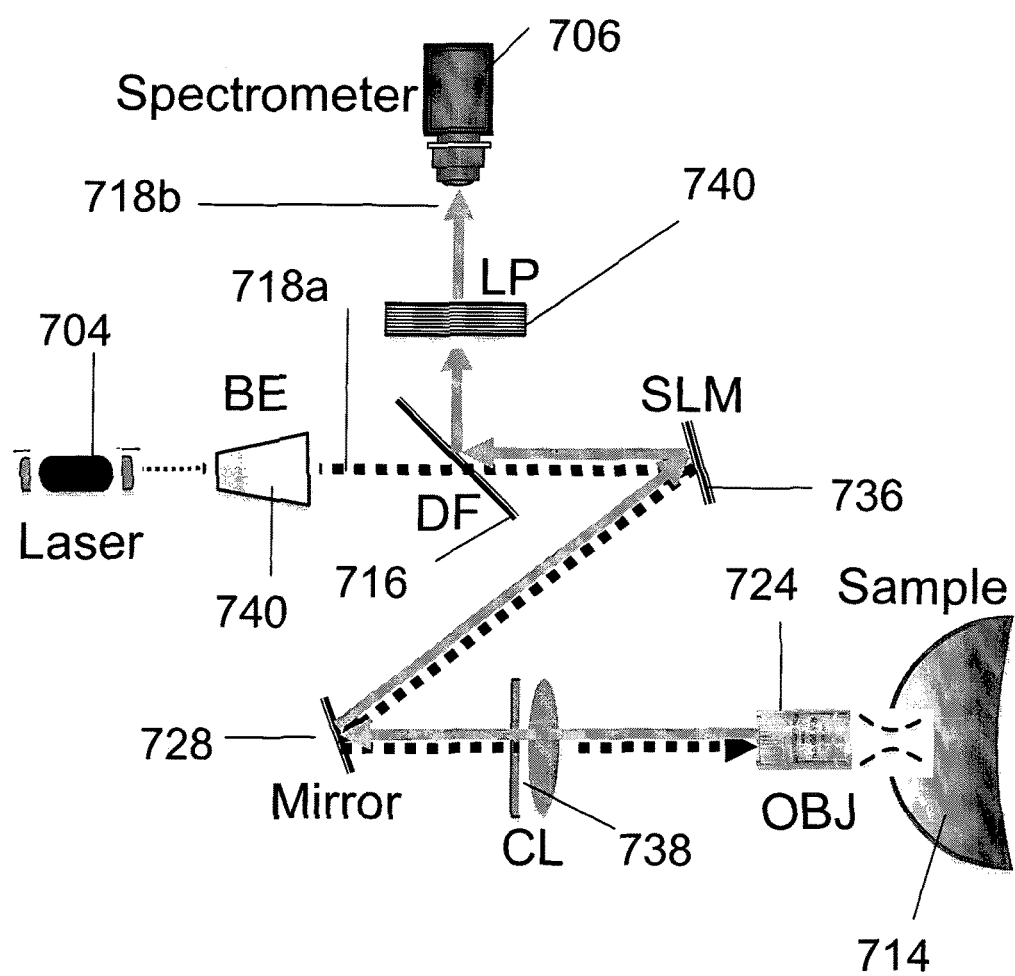
FIG. 7 is a schematic of a setup to illustrate line auto-focusing according to various embodiments.

FIG. 7 is a schematic 700 of a setup to illustrate line auto-focusing according to various embodiments. In various embodiments, references to the setup may include references to the device.

The setup may include a laser source 704 and a detector 706 such as a spectrometer. The spectrometer may include a CCD. The setup may be configured to focus a light (i.e. the second light represented by 718a) on a sample 714. The sample 714 may be an organ such as an eye but may be a non-living object for the purposes of the experiment. The setup may be further configured to direct a third light from the sample 714 to the detector 706. The third light may be the second light reflected from the sample 714.

The setup may further include a spatial light modulator (SLM) 736 for modulating the second light emitted from the laser source 704. The setup may further include a cylindrical lens (CL) 738 so that the second light focused onto the sample is a curved line.

Most current autofocusing methods may be designed for focusing on a single point. However, for Raman measurements on the eye surface, line scanning may be advantageous over point scanning because the former method offers much higher speed in data acquisition. There may be some difficulties involved in line autofocusing for the purposes of eye scanning. One difficulty may be that there are currently no existing methods for autofocusing on a line. Another difficulty may be that the eye surface is curved. The second difficulty may mean that light needs to be focused on a curve instead of a straight line. The setup may include a cylindrical lens (CL) 738 and a spatial light modulator 736 to implement line autofocusing as shown in FIG. 7. The setup may also include a filter 740, e.g. a long-pass filter (LP), between the detector 706 and a dichroic filter (DF) 716.

Light (i.e. the second light) from the laser source 704 may be expanded by the beam expander (BE) 740 first. The light (i.e. the second light) may be deflected by the SLM 736 and mirror 728 (and through the dichroic filter (DF) 716) onto the cylindrical lens (CL) 738. After passing through the cylindrical lens (CL) 738 and the objective lens (OBJ), the light (i.e. the second light) may form a line focus onto the surface of a sample to yield a bright line. The line may be a curve if the sample surface is curved. The line may be distorted if part of the light is not focused well. The line formed on the tissue surface may be imaged by the spectrometer 706 when the spectrograph inside the spectrometer is set to the position acquisition mode and its central wavelength is set to zero. The image on the CCD, which is most likely blurred initially, may be skeletonized by a computer algorithm to generate a thin line. This thin line may represent the perfect image when the line focusing is achieved. The third light may be directed by the mirror 728, the SLM 736, the DF 716 (and passing through LP 740) to detector 706. There may be two alternative methods to implement autofocusing.

In the first method, the root mean square deviation between the line image and the skeletonized image may be used to guide the spatial light modulator (SLM) 736 to shape the wavefront of light, which may in turn change the focus of each point on the line until the deviation between the two images (i.e. the line image and the skeletonized image) is minimized. All points along the line focus may be considered simultaneously.

The device or setup may include a spatial light modulator feedback circuit coupling the detector 706 to the spatial light modulator (SLM) 736. The spatial light modulator feedback circuit may be configured to generate a skeletonized line (e.g. an initial skeletonized line) based on a line (e.g. an initial line), formed by the second light (on the sample 714 or organ). The spatial light modulator feedback circuit may be configured to determine a root mean square deviation between a subsequent line (i.e. the line image) and the initial skeletonized line. The spatial light modulator (SLM) 736 may be configured to adjust, based on a feedback from the spatial light modulator feedback circuit, until the root mean square deviation of the subsequent line (i.e. the line image) and the initial skeletonized line is at a minimum.

In the second method, the focus index of each point in the skeletonized image may be calculated and fed back to the spatial light modulator (SLM) 736. The corresponding pixels in the spatial light modulator (SLM) 736 may adjust their phase values to maximize the focus index. Every point along the line focus may be considered separately.

The device or setup may include a spatial light modulator feedback circuit coupling the detector 706 to the spatial light modulator (SLM) 736. The spatial light modulator feedback circuit may be configured to generate a skeletonized line, e.g. an initial skeletonized line based on a line, e.g. an initial line, formed by the second light (on the sample 714 or organ). The (initial) skeletonized line may be used as a reference line and a focus index of each pixel along the (initial) skeletonized line may be used as reference focus index. The spatial light modulator (SLM) 736 may be configured to adjust, based on a feedback from the spatial light modulator feedback circuit, until a focus index of each pixel along a subsequent skeletonized line generated reaches a maximum value. The focus index of each pixel may be compared with the focus index of a corresponding pixel of the other skeletonized lines, e.g. the (initial) skeletonized line and the subsequent skeletonized lines. A pixel with the highest value may be determined and the spatial light modulator (SLM) 736 may be configured to be adjusted (by adjusting the phase value of each pixel of the SLM 736) so that an optimized skeletonized line including a plurality of pixels, each pixel having a highest value compared to corresponding pixels of other skeletonized line, may be generated on the sample 714.

Raman spectroscopy has been widely used in biomedical and clinical applications. Raman spectroscopy measures the inelastic scattering of photons induced by interaction with molecular bonds, and may thus contain rich biochemical information. However, due to inherently weak Raman signal, Raman data acquisition may be generally slow, which may prohibit Raman spectroscopic imaging from being used to investigate fast changing phenomena especially in biological samples.

Several Raman imaging techniques may be developed to overcome this limitation. Line scanned Raman imaging may collect both spatial and spectral information along a line simultaneously. Laser light may be shaped into a line using cylindrical optics or a scanning mechanism and Raman spectra may be collected by a two-dimensional detector array, i.e. charge-coupled device (CCD). While spatial information is acquired along the laser line, the spectral information may be collected in the dimension perpendicular to the laser line. Although the data acquisition speed is improved significantly, this method may cause field-curvature artifacts. Its actual speed may be limited by the requirement of autofocusing prior to data acquisition. Another approach for Raman imaging may be based on acousto-optic tunable filter (AOTF) or on liquid crystal tunable filter (LCTF). This approach may benefit from the capability of transmitting a selectable wavelength of light using tunable filters. However, the disadvantage of this method may include long data acquisition when the required spectral resolution is high. Fiber array Raman imaging may also be a technique which could speed up Raman acquisition significantly. Both spatial and spectral information may be collected at the same time with a fiber array by rearranging two-dimensional optical fibers array at the sample end to one-dimensional array on the detector end. However, the number of pixels in the fiber array may be limited by the amount of fibers that could be mapped onto the CCD and the spatial resolution is limited by the fiber size.

Reconstruction of the Raman signal from a few narrow-band measurements at each pixel may realize the fast Raman imaging. Only a few narrow-band Raman images may be required and the full Raman spectrum at each pixel may be reconstructed. Due to the small number of images required, the traditional spectral imaging setup, i.e. using multiple filters in front of a CCD, may work well and high spatial resolution as well as high spectral resolution may also be achieved at the same time. Data acquisition may be much faster than most current Raman imaging setups based on laser scanning.

Various embodiments may include reconstructing Raman spectra in the absence of fluorescence background. However, the drawback of this method is that it may require a calibration data set. The calibration data set may have to be similar to those obtained from test samples. Therefore, when a new type of samples is tested, a new calibration data set may be required and the size of the new calibration data may be several dozens or even several hundreds. Various embodiments may seek to find a method to suppress the calibration data size or to reduce the need of measuring the calibration data set for every new type of samples. Fluorescence background may be present in a great variety of situations and its magnitude may be often significant compared to the Raman signal unless sophisticated techniques, such as shifted excitation Raman difference spectroscopy, Fourier transformed Raman spectroscopy or temporal gating, are employed to suppress fluorescence.

Various embodiments may involve measuring the basic components, from which most test samples are made, instead of similar samples for the calibration purpose. Every type of samples may include several basic components, and the number of basic components may be much smaller than the size of the traditional calibration data set. In addition, different types of samples may share same basic components. If those basic components have been measured before, the repeated measurements of calibration data may be reduced or eliminated.

The feasibility of using basic components as the calibration data set has been demonstrated on 25 agar phantoms. The results show the potential of using basic components instead of the traditional calibration data set. This method may be extended to cell spectra of an organ such as the eye.

The phantoms were made by mixing urea (V3171, Promega corporation, US) and potassium formate (294454-500G, Sigma-Aldrich, US) in 1.5% agar (PC0701-500G, Vivantis Technologies, US) dissolved in distilled water. The concentrations of two calibration phantoms were 1 M urea and 1 M potassium formate respectively. The concentrations of 25 test phantoms for both urea and potassium formate under investigation included 0.25 M, 0.5 M, 1 M, 1.5 M and 2 M. The two calibration phantoms were used as the calibration data set and the 25 test phantoms were used as the test data set in this study.

Raman spectra were measured over a range from 600 $cm^{-1}$ to 1800 $cm^{-1}$, by using a micro-Raman system (innoRam-785S, B&W TEK, US) coupled to a video microscope sampling system (BAC151A, B&W TEK, US). The excitation wavelength was 785 nm and the spectral resolution was 4 $cm^{-1}$. The exposure time for Raman spectra was 10 s and each spectrum was accumulated for 30 times.

The narrow-band measurement c was simulated according to Equation (3).

$$c = Fs + e \quad (3)$$

where s (m×1 matrix, in which m is the number of wavenumbers) is the Raman spectrum with fluorescence background, F (n×m matrix, in which n is the number of filters) represents the transmission spectra of the filters and e (n×1 matrix) is the noise in narrow-band measurements. In Wiener estimation, a Wiener matrix W (n×m matrix) is used to transform narrow-band measurements c (m×1 matrix) into the corresponding Raman spectrums (n×1 matrix), $$\hat{s} = Wc \quad (4)$$

so that the mean square error between the original and estimated spectra is minimized. The Wiener matrix W is given by Equation (4).

$$W = K_s F^T (F K_s F^T + K_e)^{-1} \quad (5)$$

where $$K_s = E\{ss^T\}, K_e = E\{ee^T\} \quad (6)$$

In Equations (5) and (6), the superscript "T" represents matrix transpose, the superscript "−1" represents matrix inverse and E{ } represents an ensemble average. Plugging Equation (6) into Equation (7) and ignoring the noise term yields $$W = E\{sc^T\}[E\{ec^T\}]^{-1} \quad (7)$$

The PCs (principal components) based filter was used to generate the narrow-band measurements. The relative root mean square error (RMSE) of the reconstructed Raman spectrum after the removal of fluorescence background, relative to the measured Raman spectrum in which fluorescence background was also removed in the same manner, was computed as in Eq. (8).

$$\text{Relative } RMSE = \left[ \frac{\sum_{i=1}^{N} [R_r(\lambda_i) - R_m(\lambda_i)]^2}{N \times \max[R_m(\lambda_i)]^2} \right]^{1/2} \quad (8)$$

where $R_r$ and $R_m$ are the reconstructed Raman spectrum and the measured Raman spectrum (both after fluorescence background removed), respectively, $\lambda_i$ is the i-th wavenumber (i is varied from 1 to N) and the function, max[ ], returns the maximum intensity of the input spectrum.

Table 1 shows the relative RMSE for different number of Principal Components (PCs) based filters. Because there're only two basic components, the number of the PCs based filters was selected up to 2. From the result, the relative RMSE improves significantly when 2 PCs based filters were used. Table 1 shows the relative RMSE for different number of PCs based filters

TABLE 1

| PC number | 1 | 2 |
| --- | --- | --- |
| Relative RMSE | 13.9458 | 0.0642 |

Figure 8A:
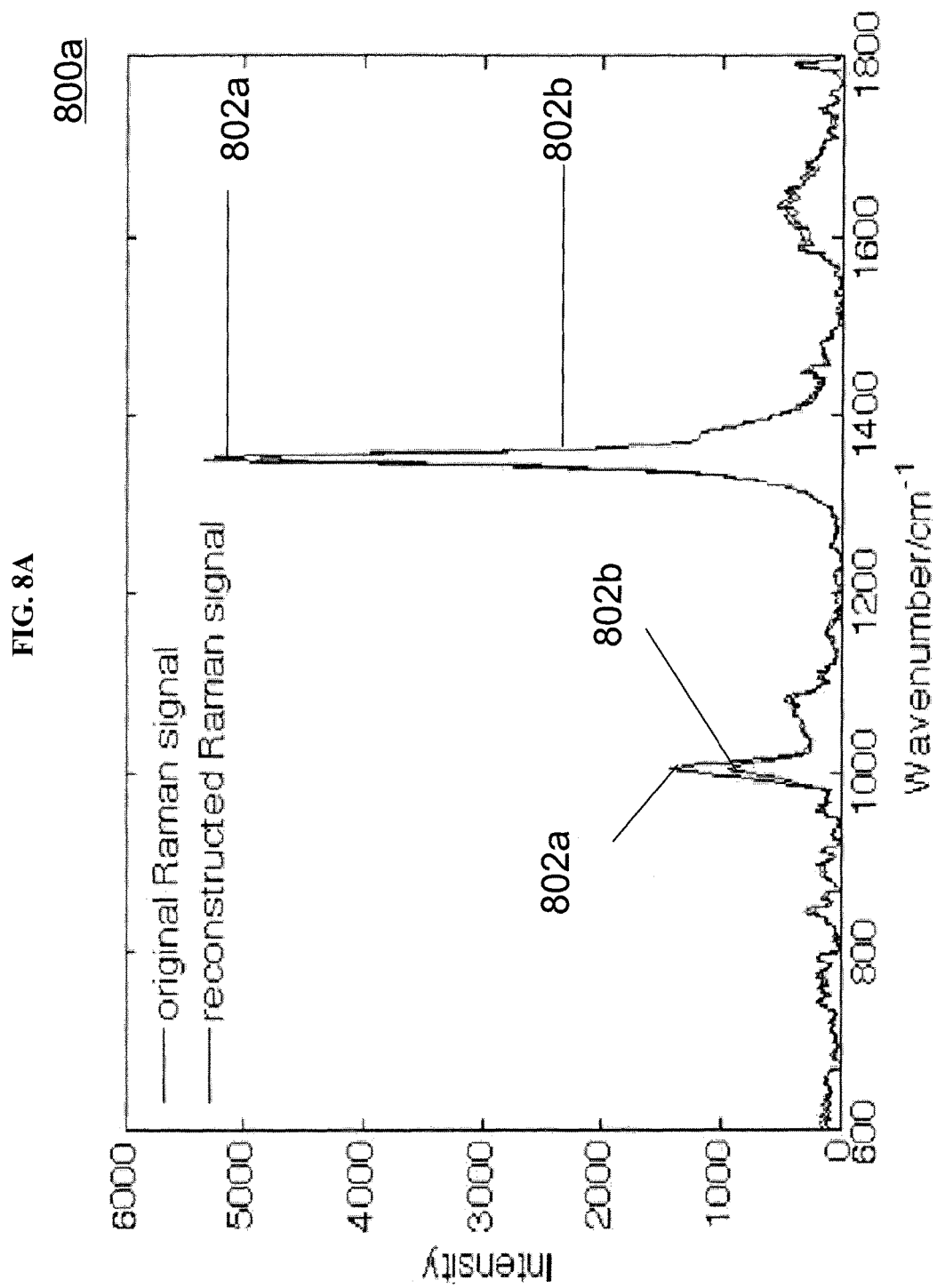
FIG. 8A is a plot of intensity (arbitrary units) against wavenumber ($cm^{-1}$) illustrating the best case of the test phantoms.
Figure 8B:
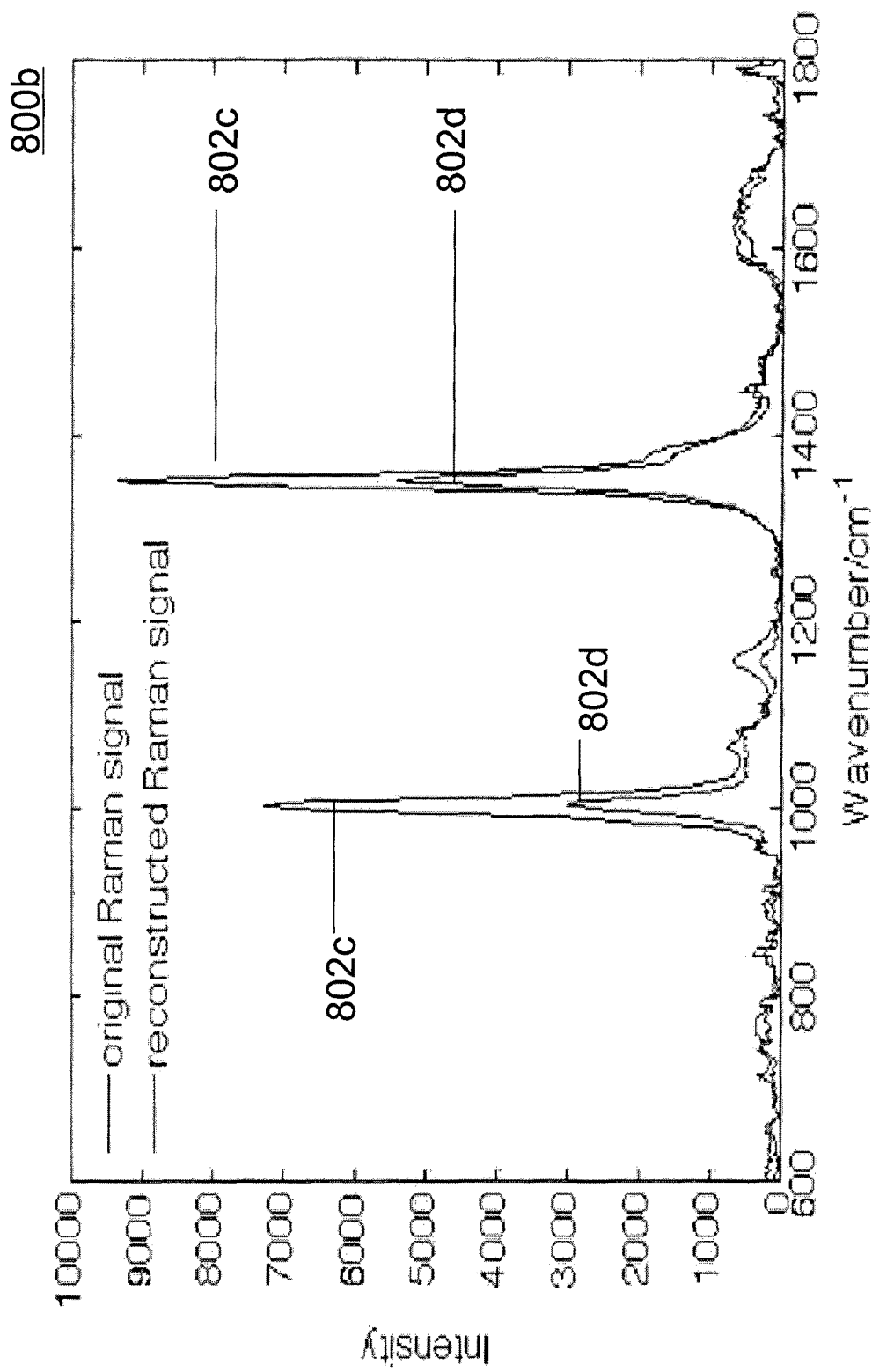
FIG. 8B is a plot of intensity (arbitrary units) against wavenumber ($cm^{-1}$) illustrating a typical case of the test phantoms.
Figure 8C:
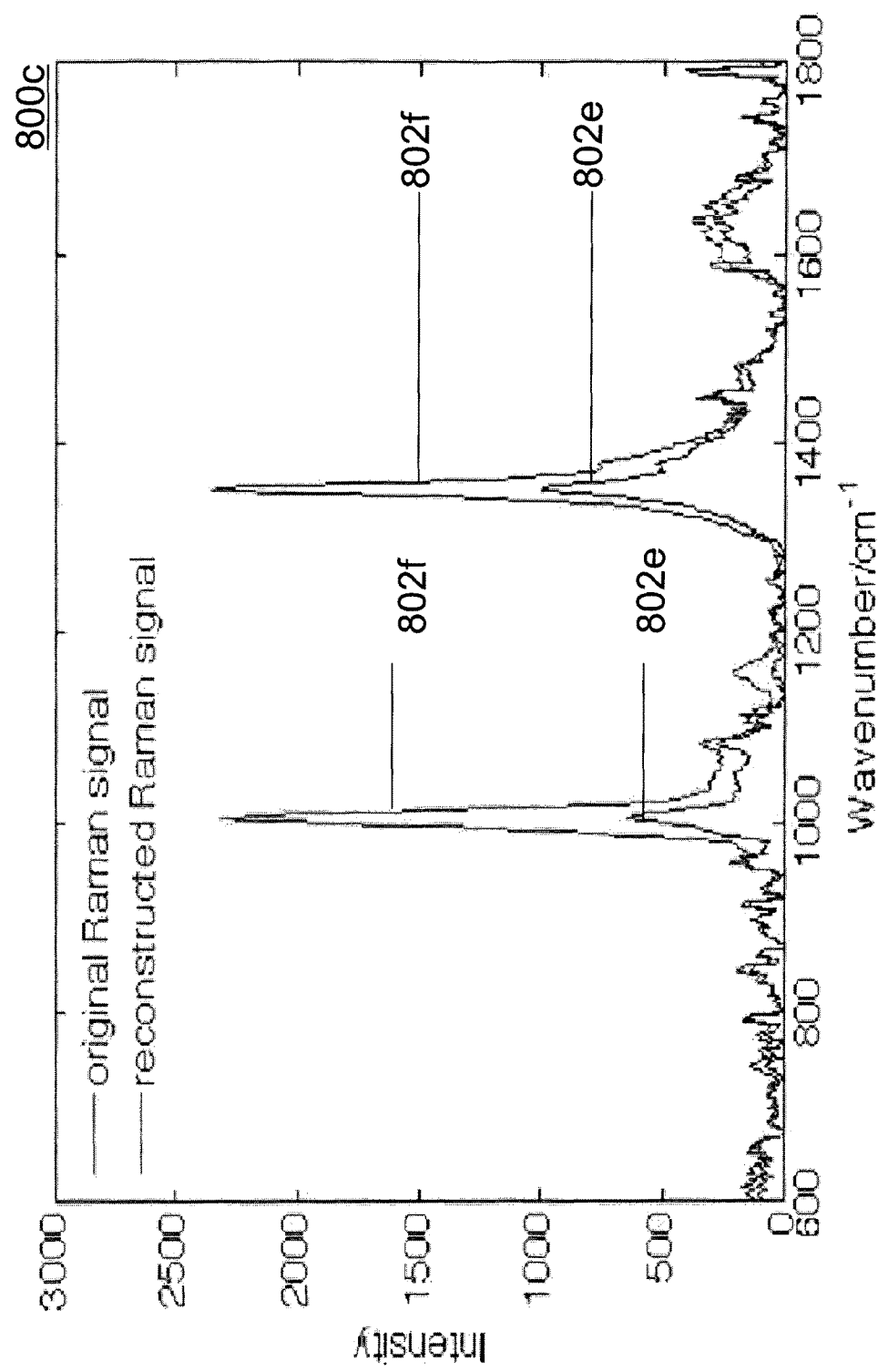
FIG. 8C is a plot of intensity (arbitrary units) against wavenumber ($cm^{-1}$) illustrating the worst case of the test phantoms.

FIG. 8A is a plot 800a of intensity (arbitrary units) against wavenumber ($cm^{-1}$) illustrating the best case of the test phantoms. FIG. 8B is a plot 800b of intensity (arbitrary units) against wavenumber ($cm^{-1}$) illustrating a typical case of the test phantoms. FIG. 8C is a plot 800c of intensity (arbitrary units) against wavenumber ($cm^{-1}$) illustrating the worst case of the test phantoms. 802a represents the original Raman signal while 802b represents the reconstructed Raman signal of the best case. 802c represents the original Raman signal while 802d represents the reconstructed Raman signal of the typical case. 802e represents the original Raman signal while 802f represents the reconstructed Raman signal of the worst case.

The relative RMSEs for the best, typical and worst case are 0.0135, 0.0703 and 0.2449, respectively. From the typical case and the worst case, it may be noted that the peak intensities of the reconstructed Raman signal are different from the peak intensities of the original Raman signal, but the relative intensities between the peaks within each sample is fairly close. The reconstructed Raman spectrum and original Raman spectrum were then normalized by dividing the intensity at each wavenumber by the sum of the intensities at all wavenumbers. The relative RMSE improves significantly to 0.0369 for 2 PCs based filters. As only one concentration for each basic component is used, the mismatching between the reconstructed and origin intensities may be due to the lack of intensity information for different concentrations of basic components. Various embodiments may include multiple concentrations of the basic components for the calibration data set. The size of the calibration data set may still be small because the large amount of combinations of the basic components is avoided and the need for the repeated measurements of the same basic components for different types of samples may be removed or reduced.

Various embodiments may provide a spectral reconstruction method based on Wiener estimation to reconstruct Raman spectra with high spectral resolution from the narrow-band Raman measurements with fluorescence background.

In another experiment, a genetic algorithm is used to identify the optimal combination of different numbers of Gaussian filters and commercial filters for spectral reconstruction to improve accuracy. The importance of spectral information in the Raman signal and that in fluorescence background were studied by exploring two sets of principal components (PCs) based filters, derived separately from principal component analysis (PCA) of clean Raman signal and fluorescence background underlying it, for spectral reconstruction. The new strategy was evaluated on both spontaneous Raman data and SERS data, in which the former data represented the case of high fluorescence background while the latter data represented the case of low fluorescence background. The results suggest the high feasibility of eliminating the requirement of sophisticated Raman system for fluorescence suppression in the reconstruction of Raman spectra using the Wiener estimation based method. Various embodiments may provide a method applicable to a simple and inexpensive Raman setup for fast Raman imaging that involve most Raman spectroscopy based applications.

Spontaneous Raman data were collected from live, apoptotic and necrotic leukemia cells using a micro-Raman system (inVia, Renishaw, UK) coupled to a microscope (Alpha 300, WITec, Germany) in a backscattering setup. Ten Raman spectra from each group were collected over a range from 600 to 1800 $cm^{-1}$. The excitation wavelength was 785 nm and the spectral resolution was 2 $cm^{-1}$.

Surface enhanced Raman spectroscopy (SERS) data were measured from blood serum samples collected from 50 patients with nasopharyngeal cancer in Fujian Tumor hospital, Fuzhou, Fujian Province, China. Blood serum samples were obtained by centrifugation at 2,000 rpm for 15 minutes in order to remove blood cells and then mixed with silver colloidal nanoparticles at a size of 34 nm. The mixture was incubated for two hours at 4° C. before measurement. A confocal Raman micro-spectrometer (inVia, Renishaw, UK) was used to measure Raman spectra over a range from 600 to 1800 $cm^{-1}$ from human blood serum. The excitation wavelength was 785 nm and the spectral resolution was 2 $cm^{-1}$. The details of sample preparation have been described in Feng et al. (Biosensors and Bioelectronics, 26, 3167, 2011) and Lin et al. Journal of Raman Spectroscopy, 43, 497, 2012).

The simulation of narrow-band measurements and methods of reconstruction and evaluation were similar to those in the previous study, which are briefly reiterated below. Since a filter is fully characterized by its transmission spectrum, it may be reasonable to expect that the result shown here faithfully mimics the real situation in which Raman spectra are acquired by using these filters. The narrow-band measurement c was simulated according to Equation (9).

$$c=Fs \qquad (9)$$

where s (m×1 matrix, in which m is the number of wavenumbers) is the Raman spectrum with fluorescence background, F (n×m matrix, in which n is the number of filters) represents the transmission spectra of the filters.

Figure 9:
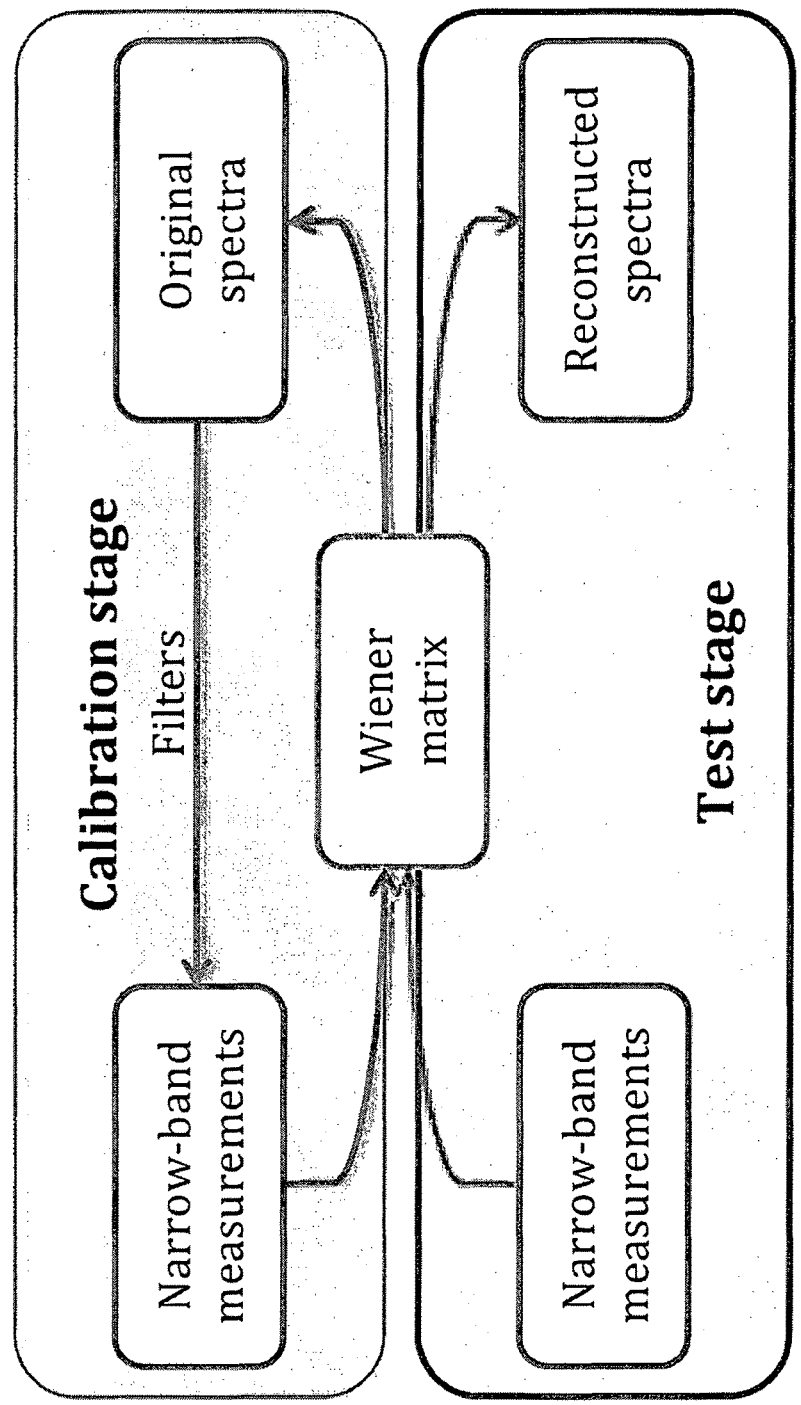
FIG. 9 is a schematic illustrating a procedure for Wiener estimation according to various embodiments.

FIG. 9 is a schematic illustrating a procedure for Wiener estimation according to various embodiments. Wiener estimation may be used to reconstruct Raman spectra from simulated narrow-band measurements, which was performed in two stages as shown in FIG. 9. In the calibration stage, Wiener matrix was constructed, which relates narrow-band measurements to the original Raman spectra measured from samples in the calibration set. In the test stage, Wiener matrix was applied to narrow-band measurements from an unknown sample to reconstruct its Raman spectrum. The Wiener matrix W may be defined in Equation (10), in which the noise term is ignored.

$$W=E(sc^T)[E(cc^T)]^{-1} \qquad (10)$$

where E( ) denotes the ensemble average, the superscript "T" denotes matrix transpose and the superscript "−1" denotes matrix inverse.

In various embodiments, the device may include a processor coupled to the detector. The device may further include one or more filters configured to generate one or more narrow-band Raman images from an image (of the organ, e.g. the eye) captured by the detector. The processor may be configured to generate a reconstructed Raman image based on the one or more narrow Raman images.

The one or more filters may be configured to generate one or more reference narrow-band Raman images from a reference image. The processor may be configured to determine a Wiener matrix based on the one or more reference narrow-band Raman images and the reference image. The processor may be configured to generate the reconstructed Raman image based on the one or more narrow Raman images and the Wiener matrix.

Modified Wiener estimation, which is based on traditional Wiener estimation, may improve reconstruction accuracy by synthesizing new narrow-band measurements with an additional set of filters. In the calibration stage, the modified Wiener matrix may be computed by the combination of original narrow-band measurements and the synthesized narrow-band measurements. In addition, two strategies may be used to find the correction relations for synthesizing new narrow-band measurements. In the test stage, new narrow-band measurements were synthesized and corrected by the correction relations obtained in the calibration stage. The modified Wiener matrix was then applied and Raman spectra may be reconstructed accurately because the new synthesized narrow-band measurements may provide additional information. A final selection step may be needed to select a better one from the results of reconstructed generated using two correction relations. More details about modified Wiener estimation have been described in Chen et al (Journal of Biomedical Optics, 17, 0305011, 2012).

In order to evaluate the accuracy of a reconstructed Raman spectrum, the reconstructed Raman spectrum may be first preprocessed to remove fluorescence background by using the fifth-order polynomial fitting. Then the relative root mean square error (RMSE) of the reconstructed Raman spectrum after the removal of fluorescence background, relative to the measured Raman spectrum in which fluorescence background may also removed in the same manner, was computed as in Equation (8).

Four different categories of filters were examined in this experiment, which include commercial filters, Gaussian filters, principal components (PCs) based filters and non-negative PCs based filters. These commercial filters, Gaussian filters, PCs based filters and non-negative PCs based filters described herein are examples and are not intended to be limiting. Table 2 illustrates the commercial filters used in the simulations of narrow-band measurements.

TABLE 2

| Manufacturer | Product numbers of commercial filters |
|---|---|
| Chroma Technique (Bellows Falls, VT, US) | D850/20m, D850/40m |
| Edmund Optics (Barrington, NJ, US) | NT 84-790, NT 84-791 |
| Omega Filters (Brattleboro, VT, US) | 3RD850LP, 3RD900LP, XB 142, XB 143, XB 146, XB 149, XF 3308, XL 19, XL 40, XLK 18, XLK 20 |
| Semrock (Rochester, NY, US) | FF 01-830/2-25, FF 01-832/37-25, FF 01-835/70-25, FF 01-840/12-25, FF 01-857/30-25, FF 01-910/5-25 |
| Thorlabs (Newton, NJ, US) | FB 830-10, FB 840-10, FB 850-10, FB 850-40, FB 860-10, FB 870-10, FB 880-10, FB 880-40, FB 890-10, FB 900-40, FB 910-10, FL 830-10, FL 850-10, FL 880-10, FL 905-10, FL 905-25 |

A total of 37 commercial filters from five manufacturers were investigated as shown in Table 2. The transmittance spectra of these filters at least partially overlap with the range of about 600 to 1 about 800 cm$^{-1}$ at an excitation wavelength of 785 nm.

A collection of 72 Gaussian filters were synthesized numerically in this study. A Gaussian filter may be expressed mathematically as $$G(\lambda) = \exp\left(\frac{-(\lambda - u)^2}{2\sigma^2}\right) \quad (11)$$

where $G(\lambda)$ denotes the transmittance at the wavelength $\lambda$, $\mu$ represents the central wavelength and $\sigma$ represents the standard deviation. The central wavelength was varied over a range from 830 nm to 910 nm and the increment was 10 nm. The standard deviation was varied over a range from 2.5 nm to 20 nm and the increment was 2.5 nm.

Both PCs based filters and non-negative PCs based filters were derived using the principle component analysis (PCA) method. In this experiment, the transmittance spectra of PCs based filters were equivalent in shape to the first several PCs of the Raman spectra with fluorescence background. The transmittance spectra of non-negative PCs based filters were generated using the same method as in Piche (Journal Optical Society of America A, 19, 1946, 2002).

Genetic algorithm may be usually used to generate useful solutions for optimization and search problems, which is based on the evolution, i.e. the survival of the fittest strategy. In the experiment, genetic algorithm has been used to find the optimal combination of Gaussian filters and that of commercial filters to achieve a minimal relative RMSE in reconstructed Raman spectra. The optimization methodology proceeded in the following manner. Firstly, a population of filter combination was initialized randomly. Secondly, Wiener estimation was applied to reconstruct Raman spectra and the mean accuracy of the reconstructed Raman spectra was evaluated. Thirdly, a new population of filter combination was generated according to the mean accuracy of the reconstructed Raman spectra, in which the filter combination yielding higher reconstruction accuracy is be more likely to become the parent for the generation of the new population. The crossover rate was 0.9 and the mutation rate was 0.1. The second and third steps were repeated iteratively until an optimized combination of filters was found. The optimization method was coded and run in Matlab (MATLAB R2011b, MathWorks, Natick, Mass., US).

The leave-one-out method was used for cross-validation in the experiment to fully utilize each sample in an unbiased manner. The measurement from one sample was used as the test data each time and the measurements from the rest of samples were used as the calibration data set. This procedure was repeated until the measurement from every sample has been tested once. For Gaussian and commercial filters, a new set of the optimal filters and Wiener matrix were generated from the calibration data set by the genetic algorithm in each round of the cross-validation and then applied to the test data. For PCs based filters and non-negative PCs based filters, the filters were fixed, thus it was not necessary to find the optimal filters. Only Wiener matrix was generated from the calibration data set in each round and then applied to the test data.

Figure 10A:
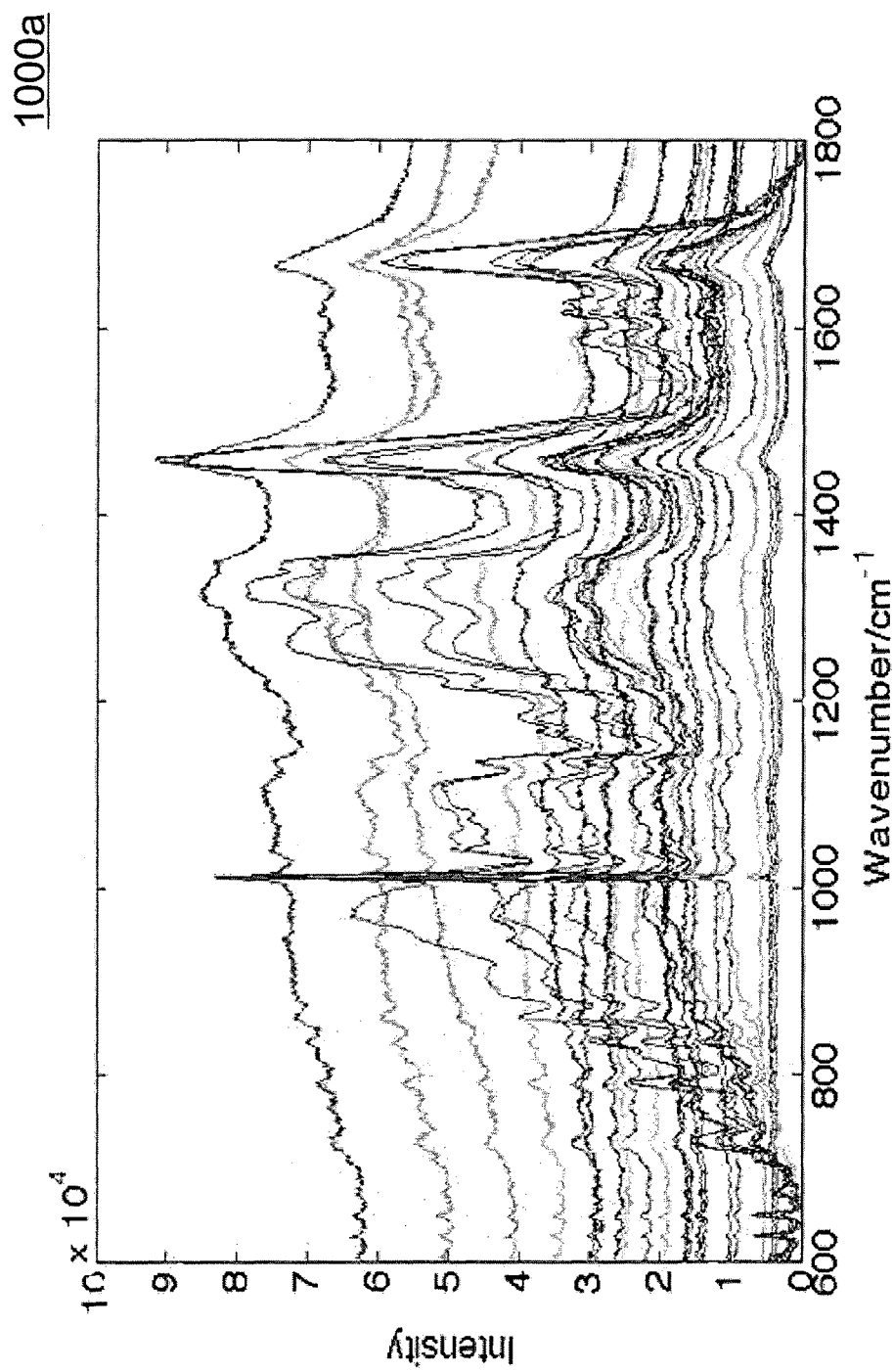
FIG. 10A is a plot of intensity (arbitrary units) against wavenumber (cm$^{-1}$) illustrating an original spontaneous Raman data, including fluorescence background, of leukemia cells.
Figure 10B:
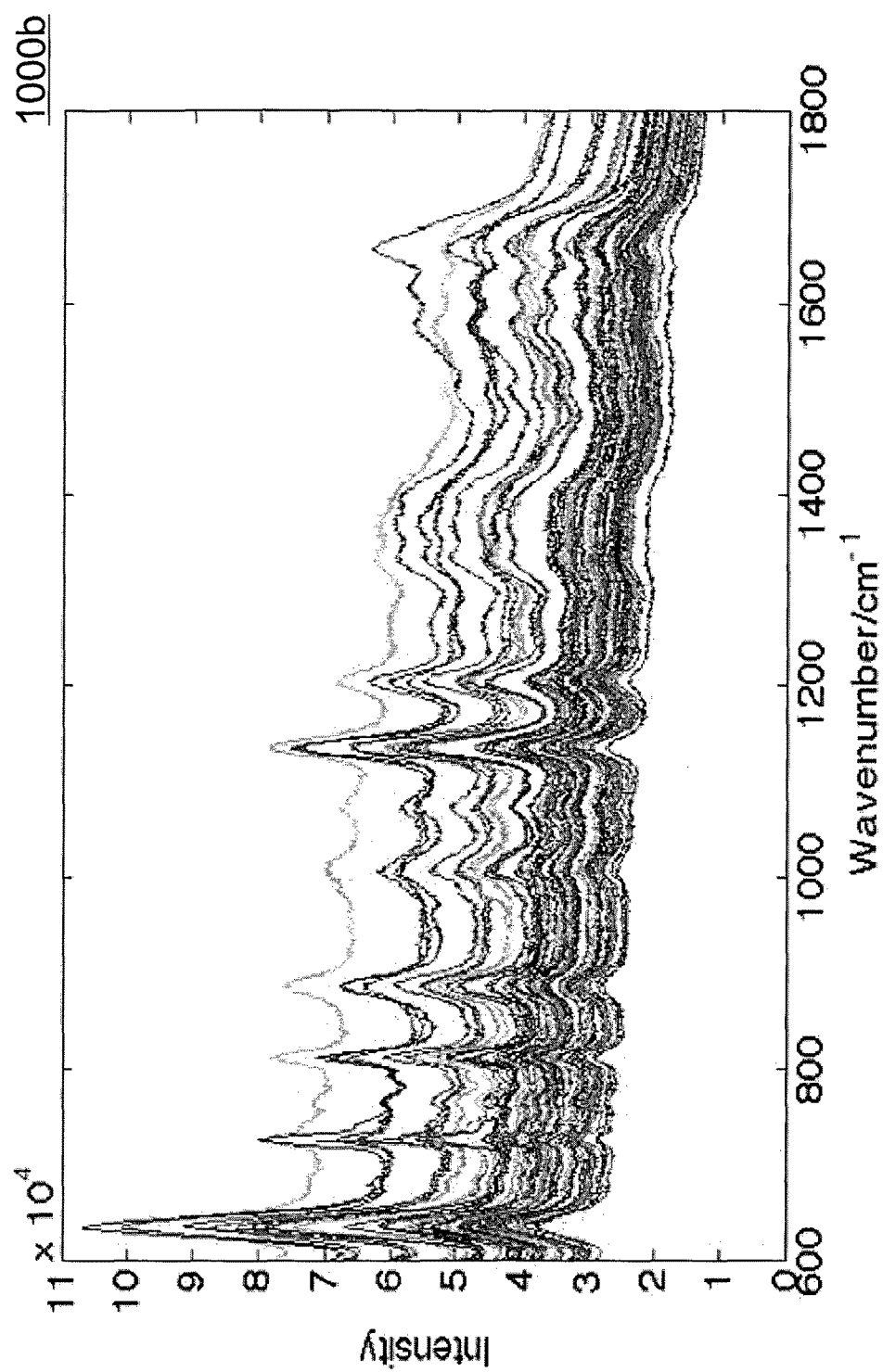
FIG. 10B is a plot of intensity (arbitrary units) against wavenumber (cm$^{-1}$) illustrating an original surface enhanced Raman spectroscopy (SERS) data, including fluorescence background, of blood serum sample.

FIG. 10A is a plot of intensity (arbitrary units) against wavenumber (cm$^{-1}$) illustrating an original spontaneous Raman data, including fluorescence background, of leukemia cells. FIG. 10B is a plot of intensity (arbitrary units) against wavenumber (cm$^{-1}$) illustrating an original surface enhanced Raman spectroscopy (SERS) data, including fluorescence background, of blood serum sample. Compared with SERS spectra from blood serum sample in FIG. 10B, the spontaneous Raman data from leukemia cells in FIG. 10A show higher variance in fluorescence background, which may be shown to affect the accuracy of reconstructed spectra.

Table 3 shows the cumulative contribution ratio of different PC numbers for spontaneous Raman spectra and SERS spectra. The cumulative contribution ratio refers to the ratio of the sum of eigenvalues corresponding to PCs of interest to the sum of all eigenvalues. By using up to six filters, a high percentage of 99.99% is reached in both sets of Raman spectra. Therefore, we test the filter number from three to six, which should be sufficient for Raman reconstruction with high accuracy.

Table 3 compares the cumulative contribution ratio of different PC numbers for spontaneous Raman spectra and SERS spectra.

TABLE 3

| PC number | Spontaneous Raman spectra (%) | SERS spectra (%) |
|---|---|---|
| 2 | 99.69 | 99.96 |
| 3 | 99.89 | 99.98 |
| 4 | 99.95 | 99.99 |
| 5 | 99.99 | 99.99 |
| 6 | 99.99 | 99.99 |
| 7 | 99.99 | 100.00 |

Table 3 shows the cumulative contribution ratio of different PC numbers for spontaneous Raman spectra and SERS spectra. The cumulative contribution ratio refers to the ratio of the sum of eigenvalues corresponding to PCs of interest to the sum of all eigenvalues. By using up to six filters, a high percentage of 99.99% is reached in both sets of Raman spectra.

Three to six filters have been tested, which should be sufficient for Raman reconstruction with high accuracy. Table 4 compares the mean relative RMSE of spontaneous Raman spectra (after fluorescence background removed) reconstructed from narrow-band measurements using different types and numbers of filters.

TABLE 4

|  | Commercial filters | Gaussian filters | PCs based filters | Non-negative PCs based filters |
| --- | --- | --- | --- | --- |
| 3 filters | $5.61 \times 10^{-2}$ | $5.18 \times 10^{-2}$ | $6.93 \times 10^{-2}$ | $6.93 \times 10^{-2}$ |
| 4 filters | $4.91 \times 10^{-2}$ | $5.07 \times 10^{-2}$ | $5.83 \times 10^{-2}$ | $5.83 \times 10^{-2}$ |
| 5 filters | $4.01 \times 10^{-2}$ | $4.37 \times 10^{-2}$ | $3.20 \times 10^{-2}$ | $3.20 \times 10^{-2}$ |
| 6 filters | $3.49 \times 10^{-2}$ | $3.54 \times 10^{-2}$ | $2.57 \times 10^{-2}$ | $2.57 \times 10^{-2}$ |

Table 4 shows the comparison in the mean relative RMSE of spontaneous Raman spectra (after fluorescence background removed) reconstructed from narrow-band measurements using different types and numbers of filters. The percentage values of reduction in the mean relative RMSE from three to four filters were 12.5%, 2.1%, 15.9% and 15.9% for commercial filters, Gaussian filters, PCs based filters and non-negative PCs based filters, respectively. The percentage values of reduction from four to five filters were 18.3%, 13.8%, 45.1% and 45.1% and the reduction from five to six filters were 13.0%, 19.0%, 19.7% and 19.7%, respectively.

Figure 11A:
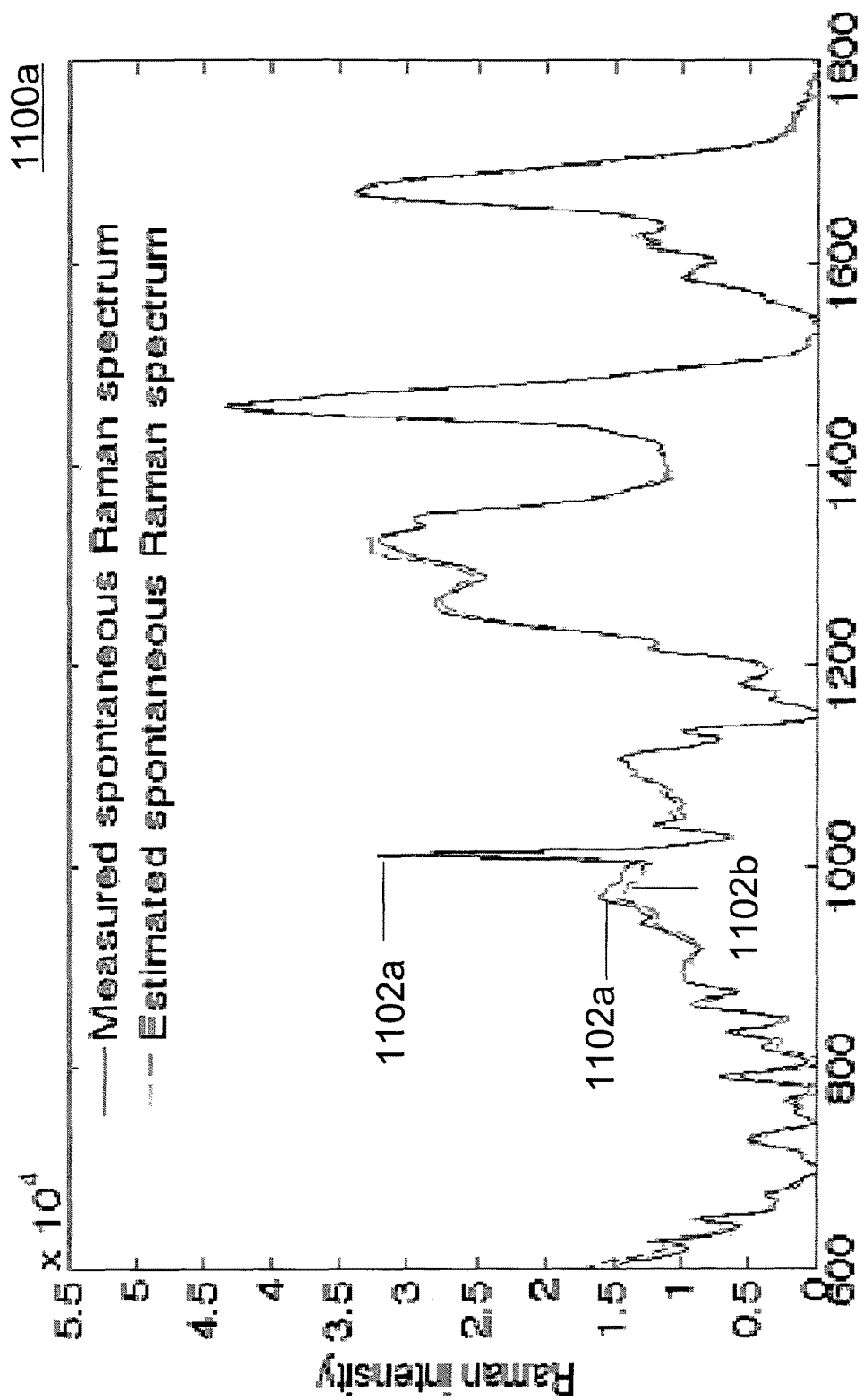
FIG. 11A is a plot of intensity (arbitrary units) against wavenumber (cm$^{-1}$) illustrating measured spontaneous Raman spectrum and the spontaneous Raman spectrum reconstructed by traditional Wiener estimation for the best case using the best combination of six commercial filters.
Figure 11B:
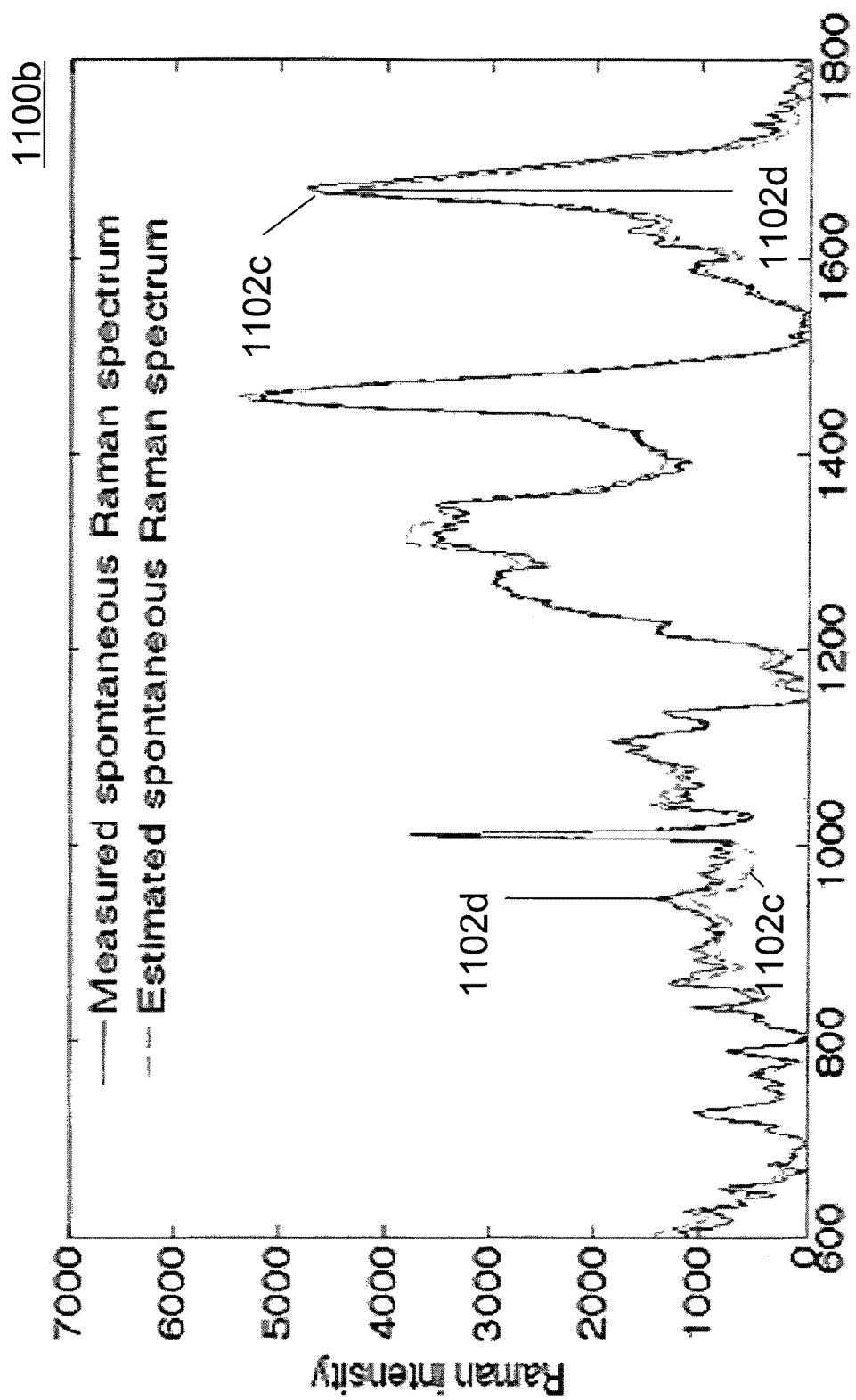
FIG. 11B is a plot of intensity (arbitrary units) against wavenumber (cm$^{-1}$) illustrating measured spontaneous Raman spectrum and the spontaneous Raman spectrum reconstructed by traditional Wiener estimation for a typical case using the best combination of six commercial filters.
Figure 11C:
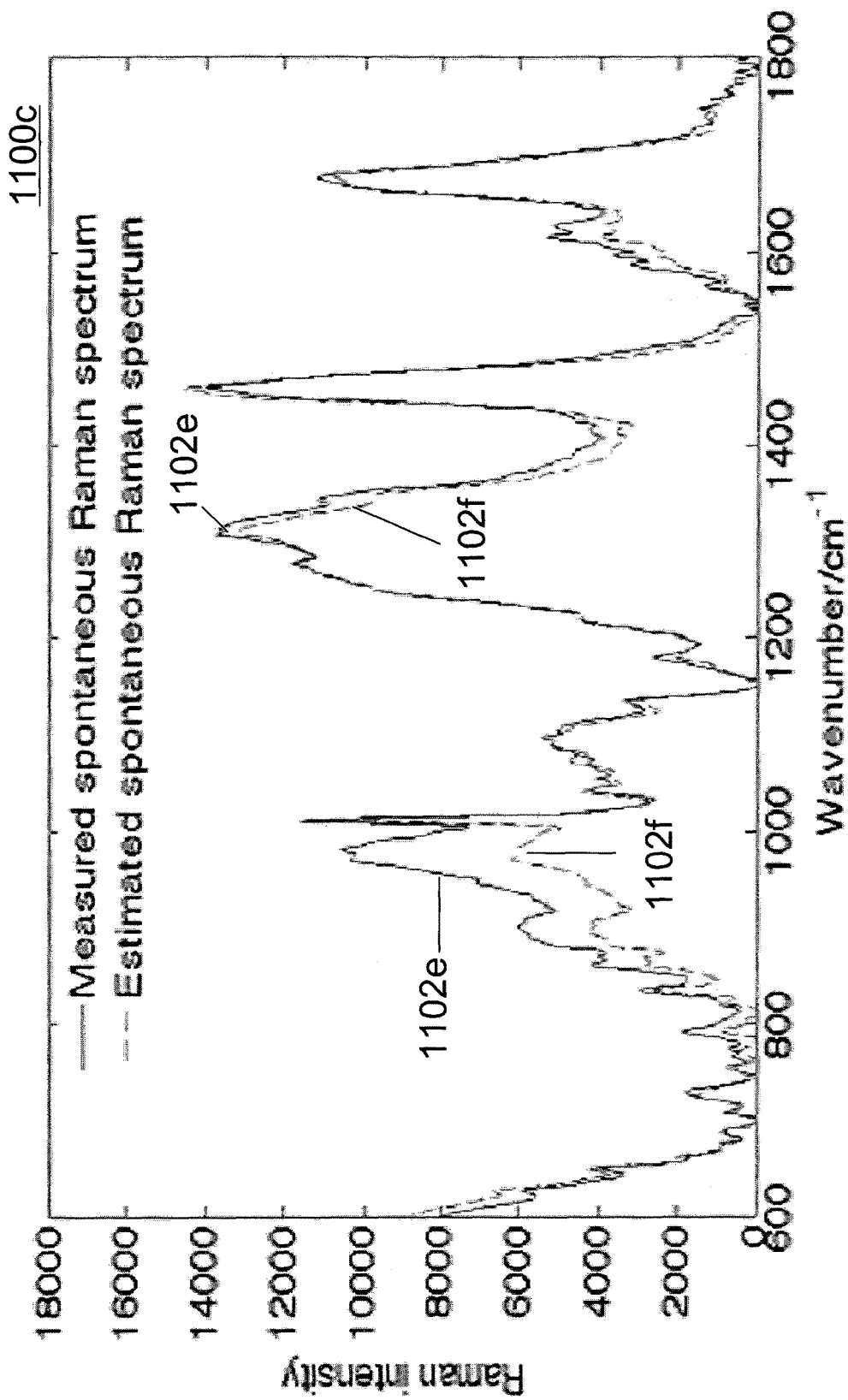
FIG. 11C is a plot of intensity (arbitrary units) against wavenumber (cm$^{-1}$) illustrating measured spontaneous Raman spectrum and the spontaneous Raman spectrum reconstructed by traditional Wiener estimation for the worst case using the best combination of six commercial filters.
Figure 11D:
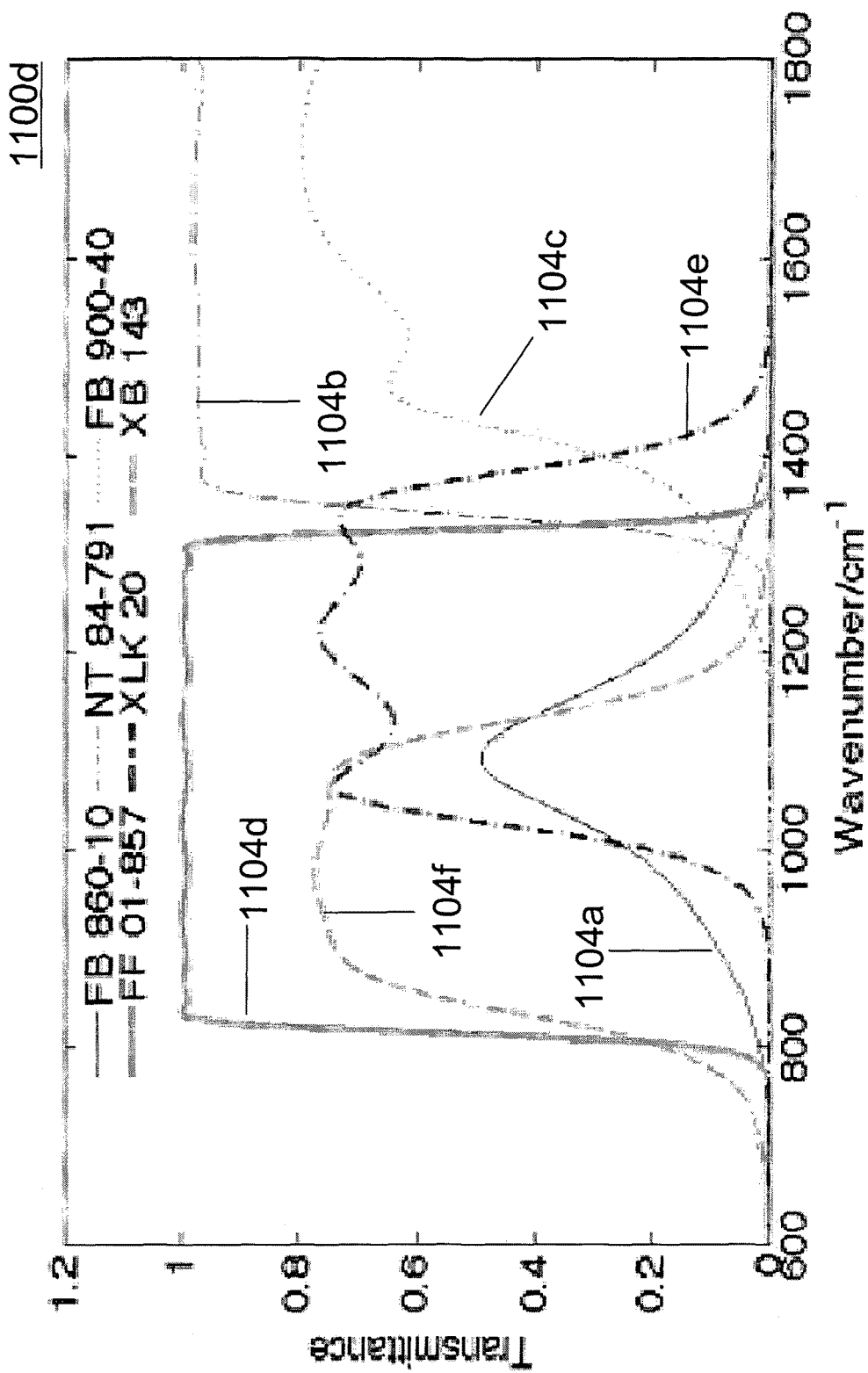
FIG. 11D is a plot of intensity (arbitrary units) against wavenumber (cm$^{-1}$) illustrating the transmittance spectra of the six commercial filters corresponding to the typical case.

FIG. 11A is a plot 1100a of intensity (arbitrary units) against wavenumber (cm$^{-1}$) illustrating measured spontaneous Raman spectrum and the spontaneous Raman spectrum reconstructed by traditional Wiener estimation for the best case using the best combination of six commercial filters. 1102a indicates the measured spontaneous Raman spectrum while 1102b indicates the reconstructed spectrum. FIG. 11B is a plot 1100b of intensity (arbitrary units) against wavenumber (cm$^{-1}$) illustrating measured spontaneous Raman spectrum and the spontaneous Raman spectrum reconstructed by traditional Wiener estimation for a typical case using the best combination of six commercial filters. 1102c indicates the measured spontaneous Raman spectrum while 1102d indicates the reconstructed spectrum. FIG. 11C is a plot 1100c of intensity (arbitrary units) against wavenumber (cm$^{-1}$) illustrating measured spontaneous Raman spectrum and the spontaneous Raman spectrum reconstructed by traditional Wiener estimation for the worst case using the best combination of six commercial filters. 1102e indicates the measured spontaneous Raman spectrum while 1102f indicates the reconstructed spectrum. FIG. 11D is a plot 1100d of intensity (arbitrary units) against wavenumber (cm$^{-1}$) illustrating the transmittance spectra of the six commercial filters corresponding to the typical case. 1104a represents the transmittance spectra of FB 860-10, 1104b represents the transmittance spectra of NT 84-791, 1104c represents the transmittance spectra of FB 900-40, 1104d represents the transmittance spectra of FF 01-857, 1104e represents the transmittance spectra of XLK 20 and 1104f represents the transmittance spectra of XB 143. The fluorescence background has been removed in both sets of spectra (measured spontaneous Raman spectrum and the spontaneous Raman spectrum reconstructed by traditional Wiener estimation) to facilitate comparison in Raman features.

FIGS. 11A-C show the comparison between the measured spontaneous Raman spectra and the spontaneous Raman spectra reconstructed by traditional Wiener estimation. FIG. 11D shows the transmittance spectra of six commercial filters corresponding to the typical case, i.e. FB 860-10, NT 84-791, FB 900-40, FF 01-857, XLK 20 and XB 143. The fluorescence background has been removed in both sets of spectra, i.e. the measured spontaneous Raman spectra and the spontaneous Raman spectra reconstructed by traditional Wiener estimation, to facilitate comparison in Raman features. The typical case (shown in FIG. 11B) is the reconstructed spontaneous Raman spectrum with a relative RMSE close to the mean relative RMSE, while the best case (shown in FIG. 11A) and worst case (shown in FIG. 11C) are the reconstructed spontaneous Raman spectra with the minimum relative RMSE and maximum relative RMSE. The relative RMSEs are $1.57 \times 10^{-2}$, $3.29 \times 10^{-2}$, $6.69 \times 10^{-2}$ in the best case, the typical case and the worst case, respectively.

Figure 12A:
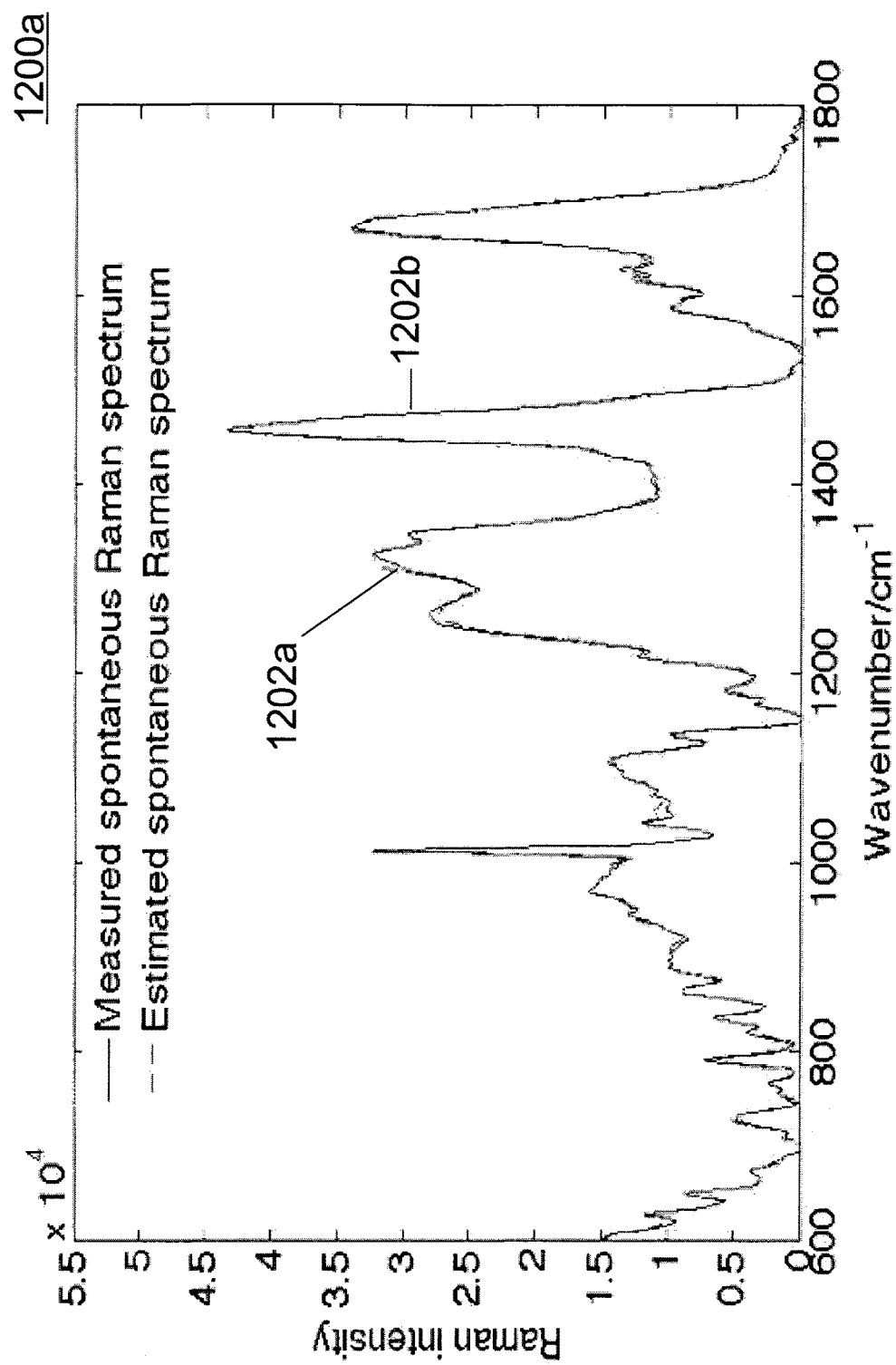
FIG. 12A is a plot of intensity (arbitrary units) against wavenumber (cm$^{-1}$) illustrating measured spontaneous Raman spectrum and the spontaneous Raman spectrum reconstructed by traditional Wiener estimation for the best case using the best combination of six non-negative principal components (PCs) based filters.
Figure 12B:
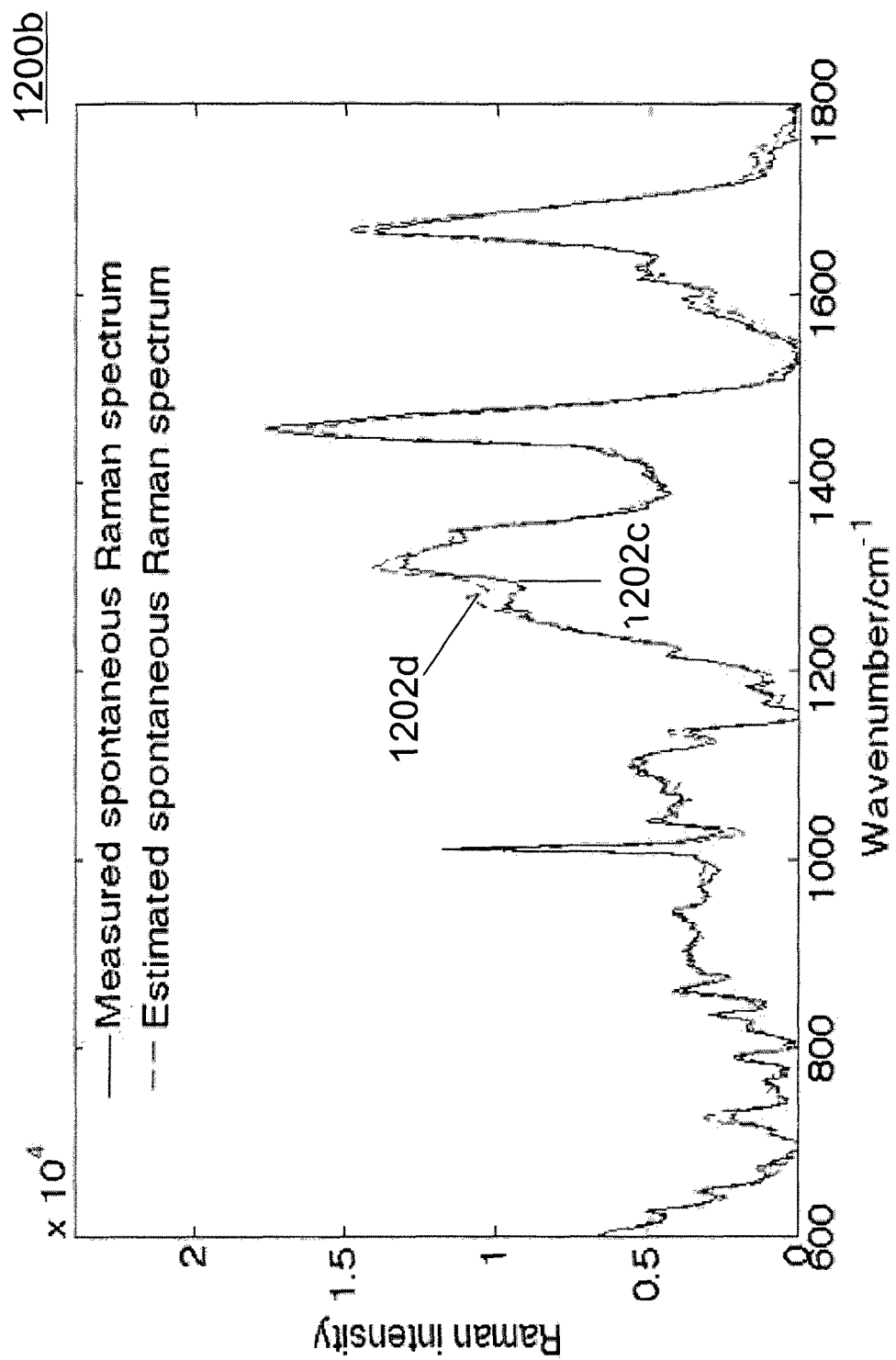
FIG. 12B is a plot of intensity (arbitrary units) against wavenumber (cm$^{-1}$) illustrating measured spontaneous Raman spectrum and the spontaneous Raman spectrum reconstructed by traditional Wiener estimation for a typical case using the best combination of six non-negative principal components (PCs) based filters.
Figure 12C:
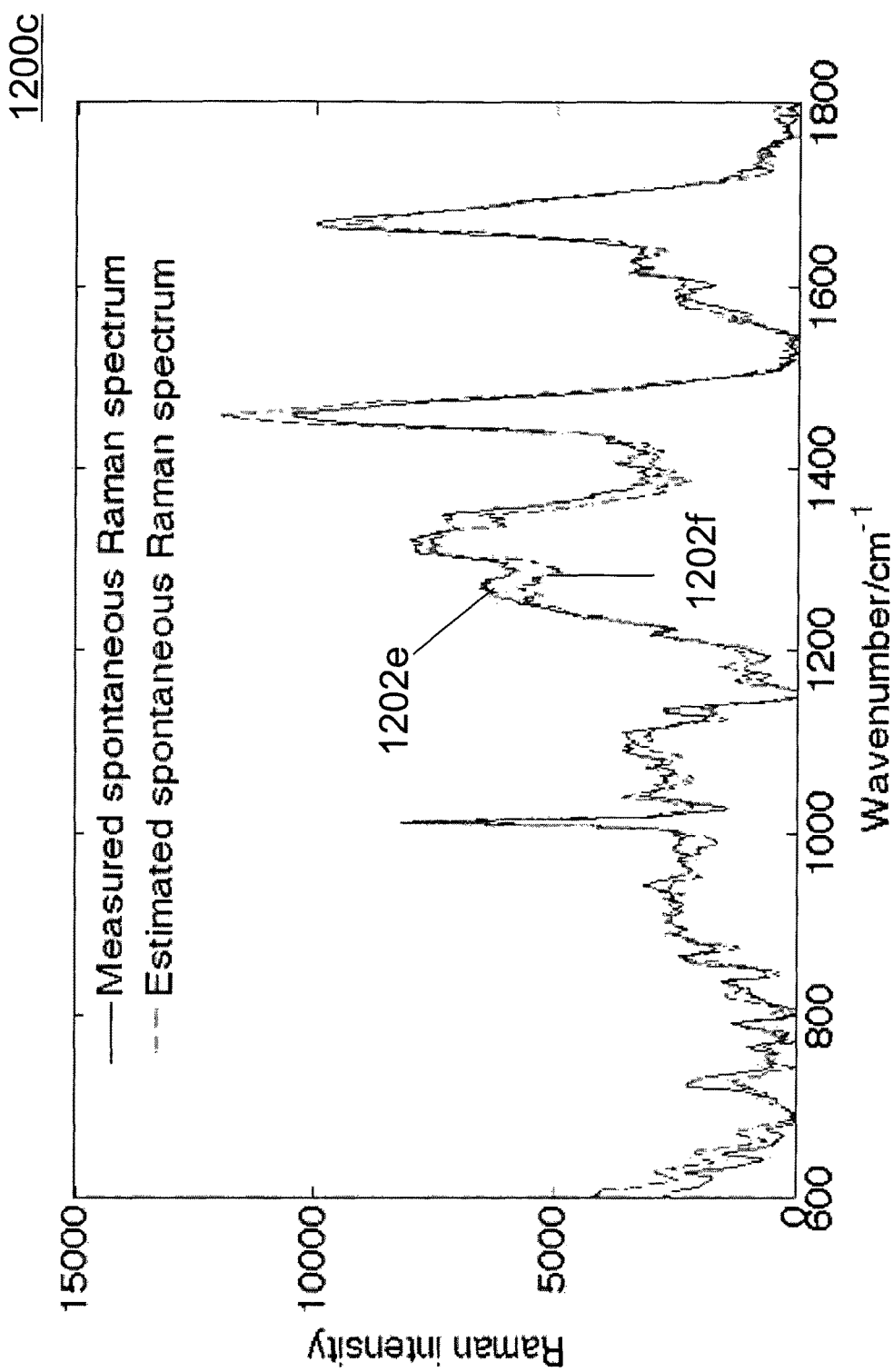
FIG. 12C is a 1200c of intensity (arbitrary units) against wavenumber (cm$^{-1}$) illustrating measured spontaneous Raman spectrum and the spontaneous Raman spectrum reconstructed by traditional Wiener estimation for the worst case using the best combination of six non-negative principal components (PCs) based filters.
Figure 12D:
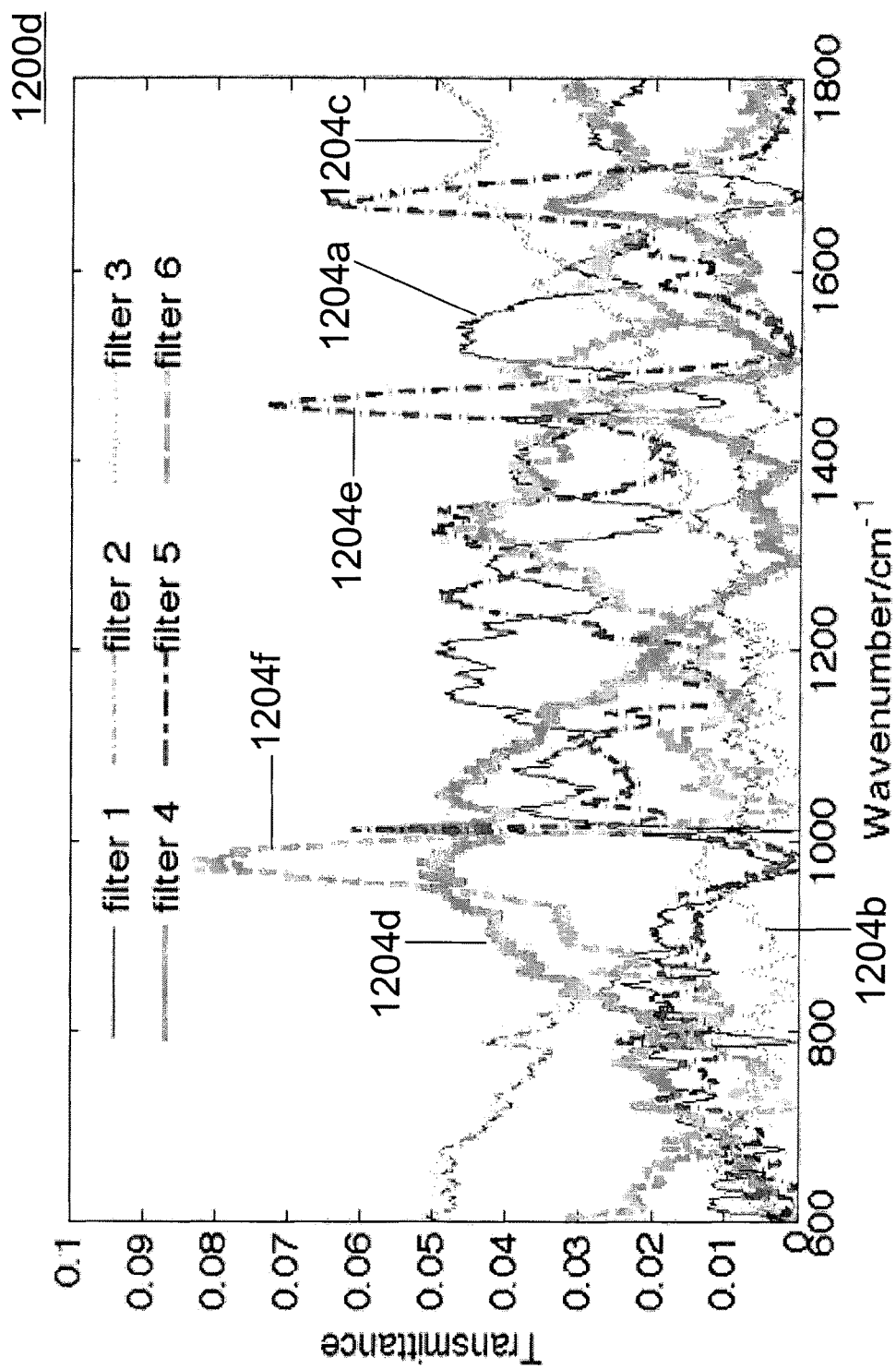
FIG. 12D is a plot of intensity (arbitrary units) against wavenumber (cm$^{-1}$) illustrating the transmittance spectra of the six non-negative principal components (PCs) based filters corresponding to the typical case.

FIG. 12A is a plot 1200a of intensity (arbitrary units) against wavenumber (cm$^{-1}$) illustrating measured spontaneous Raman spectrum and the spontaneous Raman spectrum reconstructed by traditional Wiener estimation for the best case using the best combination of six non-negative principal components (PCs) based filters. 1202a indicates the measured spontaneous Raman spectrum while 1202b indicates the reconstructed spectrum. FIG. 12B is a plot 1200b of intensity (arbitrary units) against wavenumber (cm$^{-1}$) illustrating measured spontaneous Raman spectrum and the spontaneous Raman spectrum reconstructed by traditional Wiener estimation for a typical case using the best combination of six non-negative principal components (PCs) based filters. 1202c indicates the measured spontaneous Raman spectrum while 1202d indicates the reconstructed spectrum. FIG. 12C is a plot 1200c of intensity (arbitrary units) against wavenumber (cm$^{-1}$) illustrating measured spontaneous Raman spectrum and the spontaneous Raman spectrum reconstructed by traditional Wiener estimation for the worst case using the best combination of six non-negative principal components (PCs) based filters. 1202e indicates the measured spontaneous Raman spectrum while 1202f indicates the reconstructed spectrum. FIG. 12D is a plot 1200d of intensity (arbitrary units) against wavenumber (cm$^{-1}$) illustrating the transmittance spectra of the six non-negative principal components (PCs) based filters corresponding to the typical case. 1204a represents the transmittance spectra of the first filter, 1204b represents the transmittance spectra of the second filter, 1204c represents the transmittance spectra of the third filter, 1204d represents the transmittance spectra of the fourth filter, 1204e represents the transmittance spectra of the fifth filter and 1204f represents the transmittance spectra of the sixth filter. The fluorescence background has been removed in both sets of spectra (measured spontaneous Raman spectrum and the spontaneous Raman spectrum reconstructed by traditional Wiener estimation) to facilitate comparison in Raman features.

FIG. 12A-C show the comparison between the measured spontaneous Raman spectra and the spontaneous Raman spectra reconstructed by traditional Wiener estimation with the first six non-negative PCs based filters. The relative RMSEs were $9.3 \times 10^{-3}$, $2.55 \times 10^{-2}$, $4.99 \times 10^{-2}$ in the best case, the typical case and the worst case, respectively.

Table 5 shows the comparison in the mean relative RMSE of reconstructed SERS spectra (after fluorescence background removed) from narrow-band measurements using different types and numbers of filters. The percentage values of reduction in the mean relative RMSE from three to four filters were 2.7%, 2.7%, 5.1% and 5.1% for commercial filters, Gaussian filters, PCs based filters and non-negative PCs based filters, respectively. The percentage values of reduction from four to five filters were 1.2%, 3.9%, 19.3% and 19.3% and the percentage values of reduction from five to six filters were 15.0%, 10.1%, 11.7% and 11.7%, respectively.

Table 5 compares the mean relative RMSE of SERS spectra (after fluorescence background removed) reconstructed from narrow-band measurements using different types and numbers of filters.

TABLE 5

|  | Commercial filters | Gaussian filters | PCs based filters | Non-negative PCs based filters |
|---|---|---|---|---|
| 3 filters | $2.65 \times 10^{-2}$ | $2.64 \times 10^{-2}$ | $2.13 \times 10^{-2}$ | $2.13 \times 10^{-2}$ |
| 4 filters | $2.57 \times 10^{-2}$ | $2.57 \times 10^{-2}$ | $2.02 \times 10^{-2}$ | $2.02 \times 10^{-2}$ |
| 5 filters | $2.54 \times 10^{-2}$ | $2.47 \times 10^{-2}$ | $1.63 \times 10^{-2}$ | $1.63 \times 10^{-2}$ |
| 6 filters | $2.16 \times 10^{-2}$ | $2.22 \times 10^{-2}$ | $1.44 \times 10^{-2}$ | $1.44 \times 10^{-2}$ |

Figure 13A:
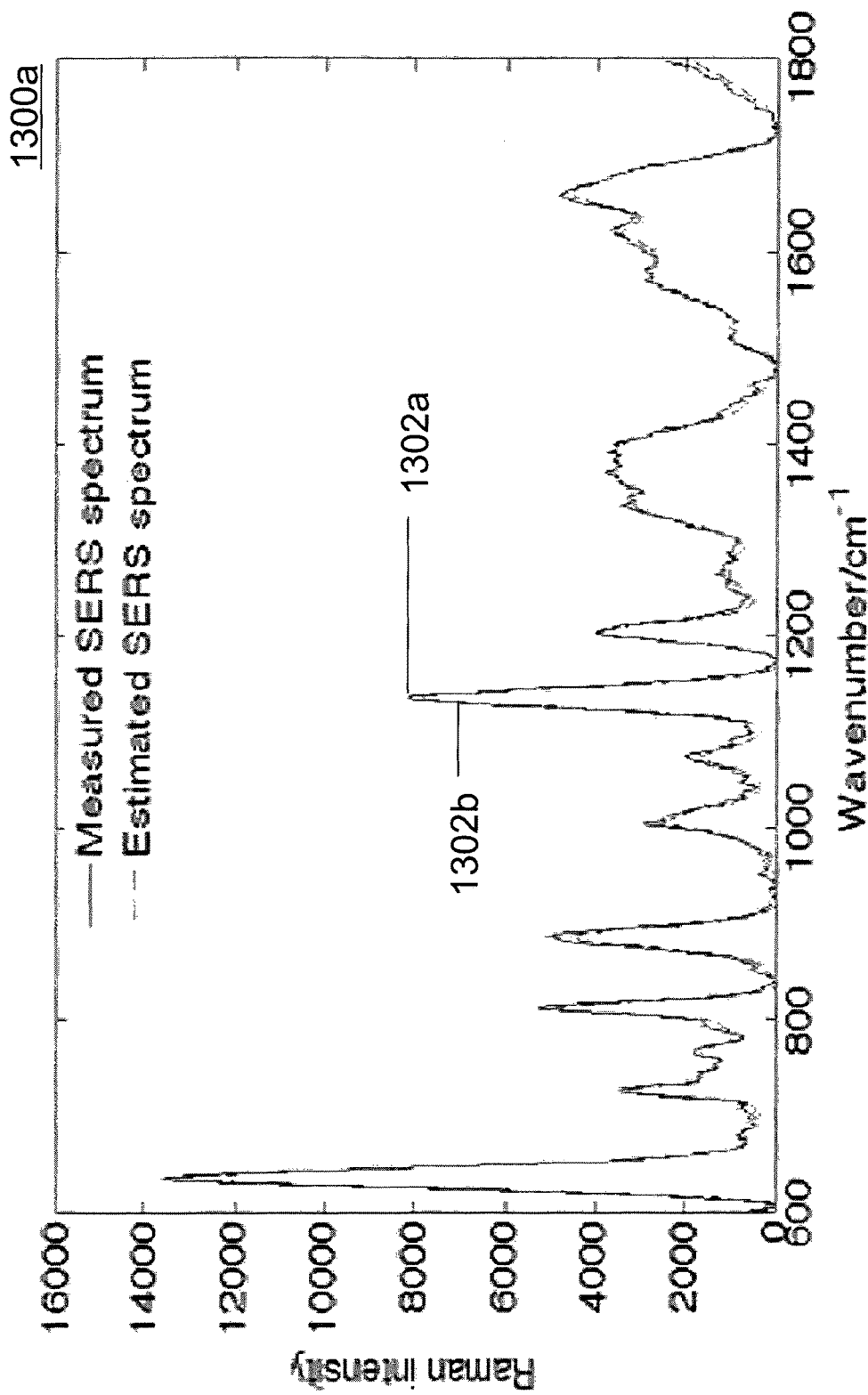
FIG. 13A is a plot of intensity (arbitrary units) against wavenumber (cm$^{-1}$) illustrating measured surface enhanced Raman spectroscopy (SERS) Raman spectrum and the surface enhanced Raman spectroscopy (SERS) Raman spectrum reconstructed by traditional Wiener estimation for the best case using the best combination of six commercial filters.
Figure 13B:
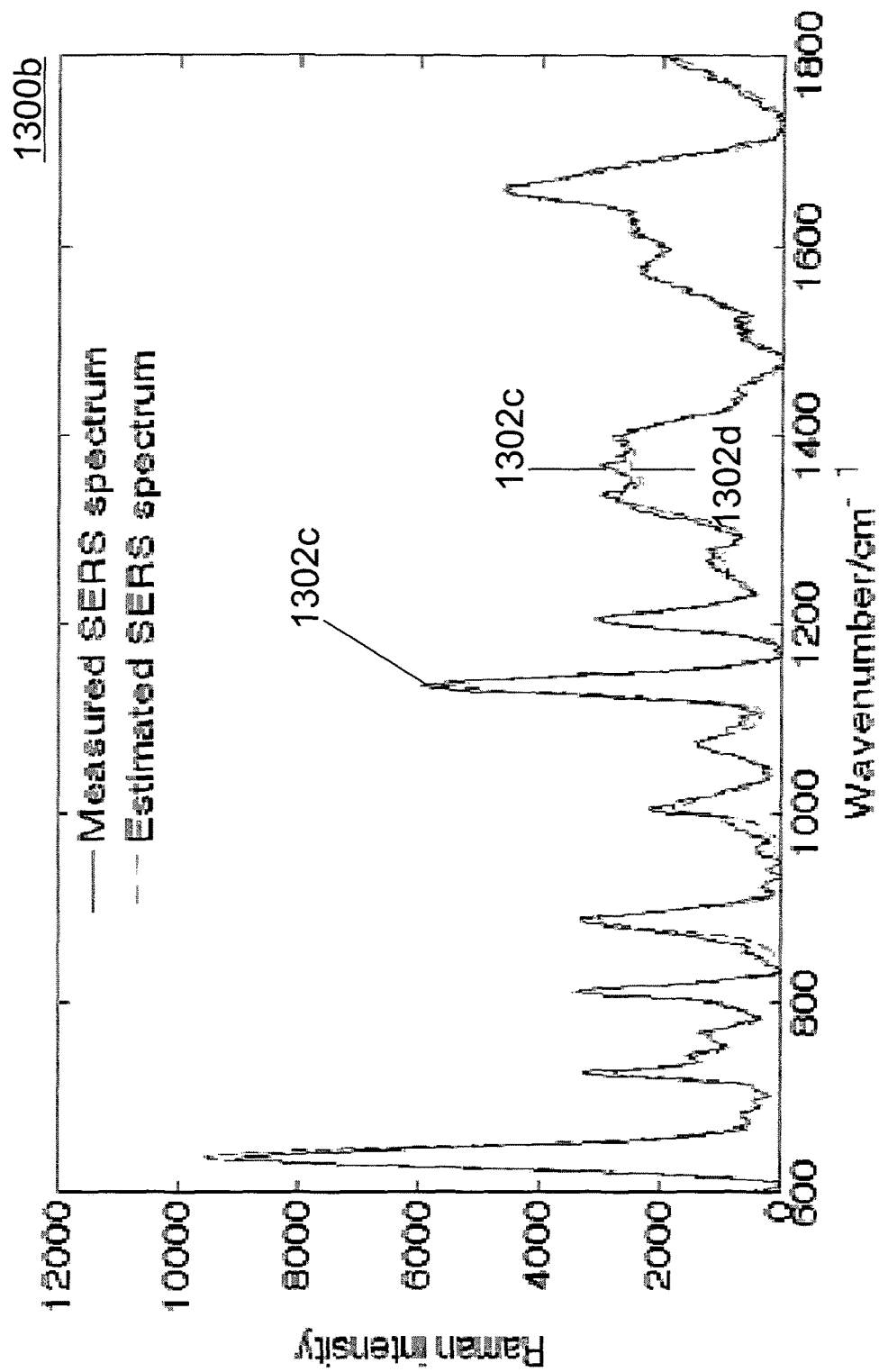
FIG. 13B is a plot of intensity (arbitrary units) against wavenumber (cm$^{-1}$) illustrating measured surface enhanced Raman spectroscopy (SERS) spectrum and the surface enhanced Raman spectroscopy (SERS) spectrum reconstructed by traditional Wiener estimation for a typical case using the best combination of six commercial filters.
Figure 13C:
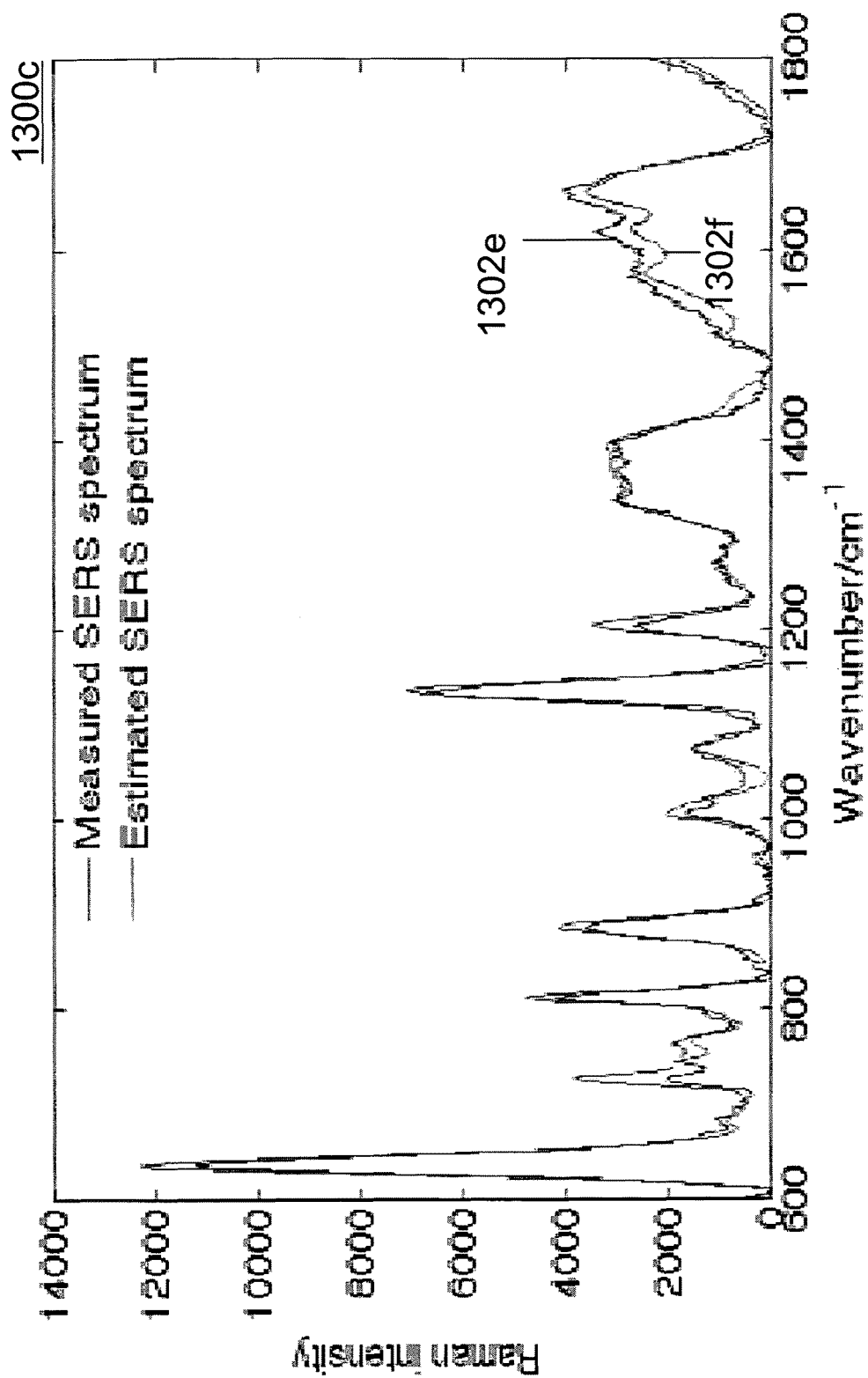
FIG. 13C is a plot of intensity (arbitrary units) against wavenumber (cm$^{-1}$) illustrating measured surface enhanced Raman spectroscopy (SERS) spectrum and the surface enhanced Raman spectroscopy (SERS) spectrum reconstructed by traditional Wiener estimation for the worst case using the best combination of six commercial filters.
Figure 13D:
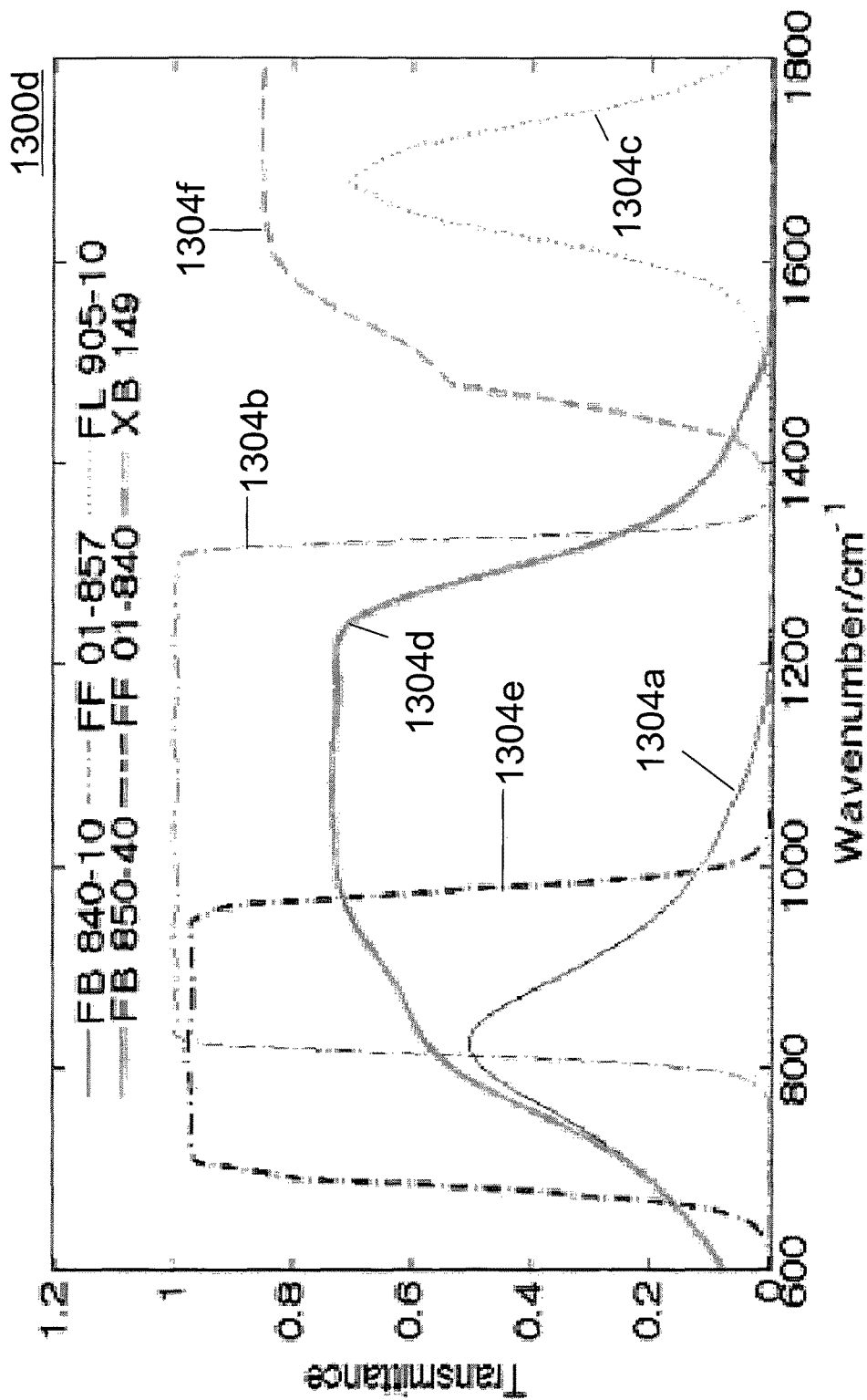
FIG. 13D is a plot of intensity (arbitrary units) against wavenumber (cm$^{-1}$) illustrating the transmittance spectra of the six commercial filters corresponding to the typical case.

FIG. 13A is a plot 1300a of intensity (arbitrary units) against wavenumber ($cm^{-1}$) illustrating llustrating measured surface enhanced Raman spectroscopy (SERS) spectrum and the surface enhanced Raman spectroscopy (SERS) Raman spectrum reconstructed by traditional Wiener estimation for the best case using the best combination of six commercial filters. 1302a indicates the measured surface enhanced Raman spectroscopy (SERS) spectrum while 1302b indicates the reconstructed spectrum. FIG. 13B is a plot 1300b of intensity (arbitrary units) against wavenumber ($cm^{-1}$) illustrating measured surface enhanced Raman spectroscopy (SERS) spectrum and the surface enhanced Raman spectroscopy (SERS) spectrum reconstructed by traditional Wiener estimation for a typical case using the best combination of six commercial filters. 1302c indicates the measured surface enhanced Raman spectroscopy (SERS) spectrum while 1302d indicates the reconstructed spectrum. FIG. 13C is a plot 1300c of intensity (arbitrary units) against wavenumber ($cm^{-1}$) illustrating measured surface enhanced Raman spectroscopy (SERS) spectrum and the surface enhanced Raman spectroscopy (SERS) spectrum reconstructed by traditional Wiener estimation for the worst case using the best combination of six commercial filters. 1302e indicates the measured surface enhanced Raman spectroscopy (SERS) spectrum while 1302f indicates the reconstructed spectrum. FIG. 13D is a plot 1300d of intensity (arbitrary units) against wavenumber ($cm^{-1}$) illustrating the transmittance spectra of the six commercial filters corresponding to the typical case. 1304a represents the transmittance spectra of FB 840-10, 1304b represents the transmittance spectra of FF 01-857, 1304c represents the transmittance spectra of FL 905-10, 1304d represents the transmittance spectra of FB 850-40, 1304e represents the transmittance spectra of FF01-840 and 1304f represents the transmittance spectra of XB 149. The fluorescence background has been removed in both sets of spectra (measured surface enhanced Raman spectroscopy (SERS) spectrum and the surface enhanced Raman spectroscopy (SERS) spectrum reconstructed by traditional Wiener estimation) to facilitate comparison in Raman features.

FIGS. 13A-C show the comparison between the measured SERS spectrum and the SERS spectrum reconstructed by traditional Wiener estimation and the transmittance spectra of the best combination of six commercial filters corresponding to the typical case, i.e. FL 840-10, FF 01-857, FL 905-10, FB 850-40, FF 01-840 and XB 149. The relative RMSEs were $9.1 \times 10^{-3}$, $2.13 \times 10^{-2}$ and $5.76 \times 10^{-2}$ in the best case, the typical case and the worst case, respectively.

Figure 14A:
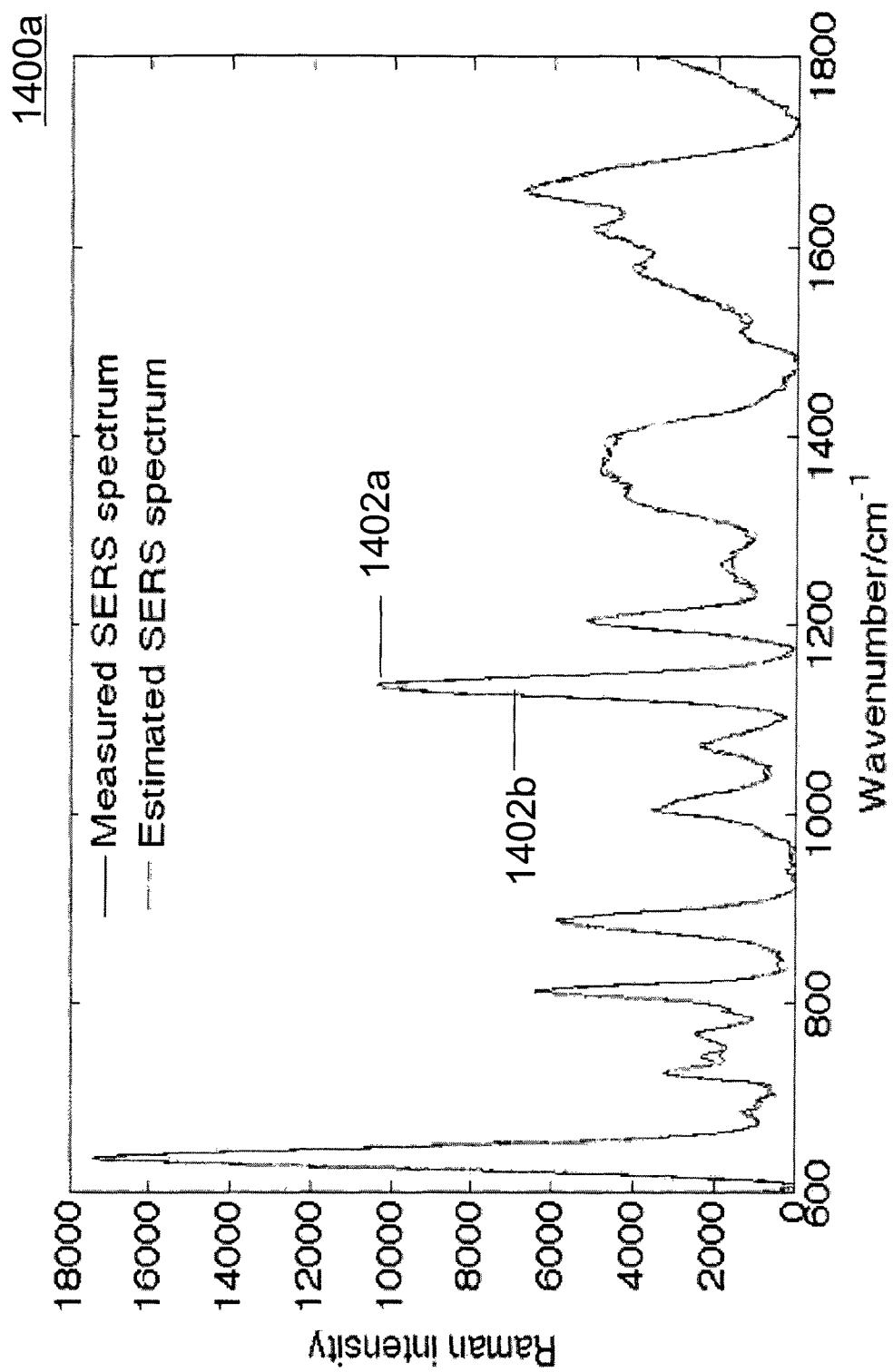
FIG. 14A is a plot of intensity (arbitrary units) against wavenumber (cm$^{-1}$) illustrating measured surface enhanced, Raman spectroscopy (SERS) spectrum and the surface enhanced Raman spectroscopy (SERS) spectrum reconstructed by traditional Wiener estimation for the best case using the best combination of six non-negative principal components (PCs) based filters.
Figure 14B:
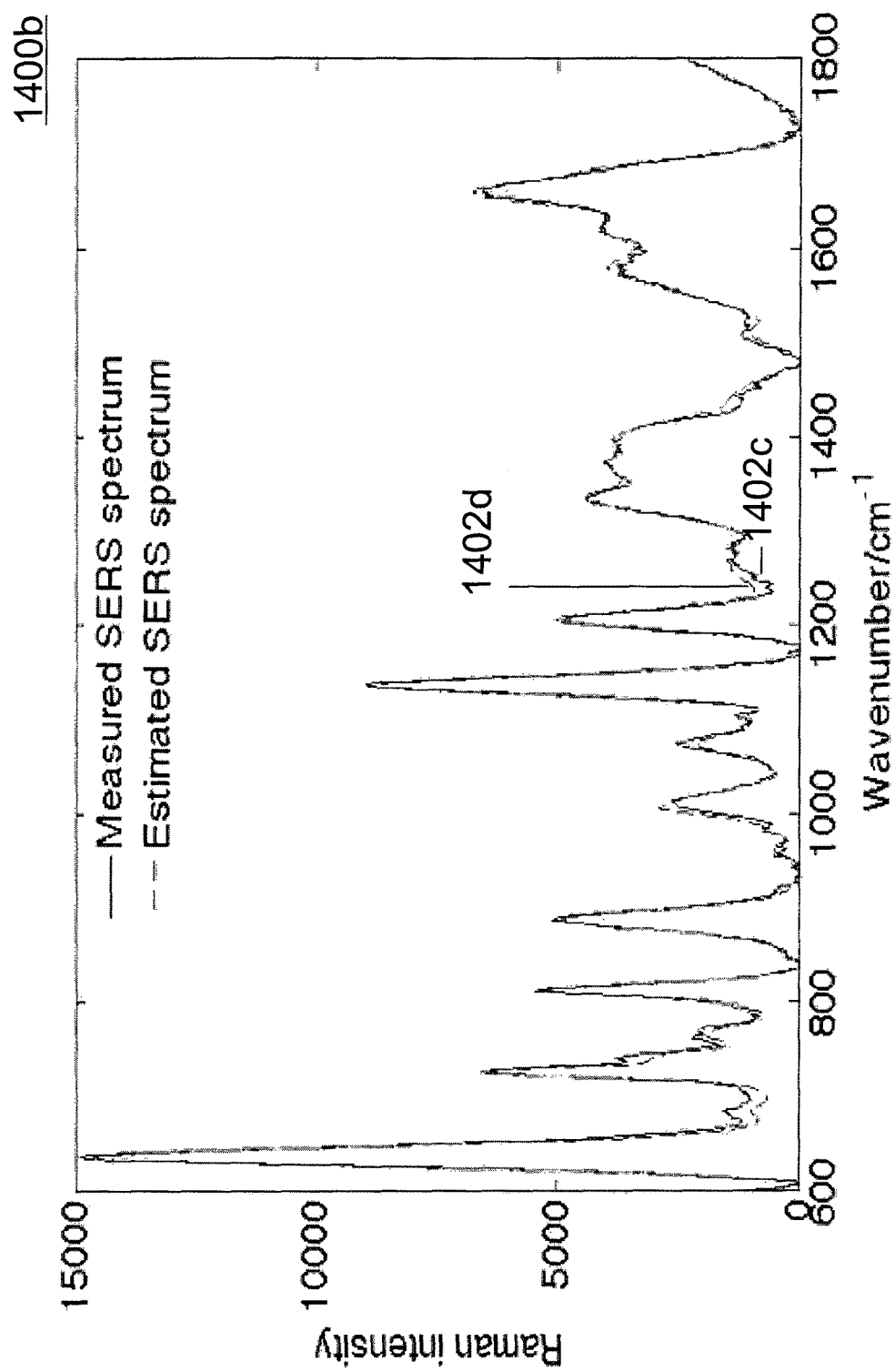
FIG. 14B is a plot of intensity (arbitrary units) against wavenumber (cm$^{-1}$) illustrating measured surface enhanced Raman spectroscopy (SERS) spectrum and the surface enhanced Raman spectroscopy (SERS) spectrum reconstructed by traditional Wiener estimation for a typical case using the best combination of six non-negative principal components (PCs) based filters.
Figure 14C:
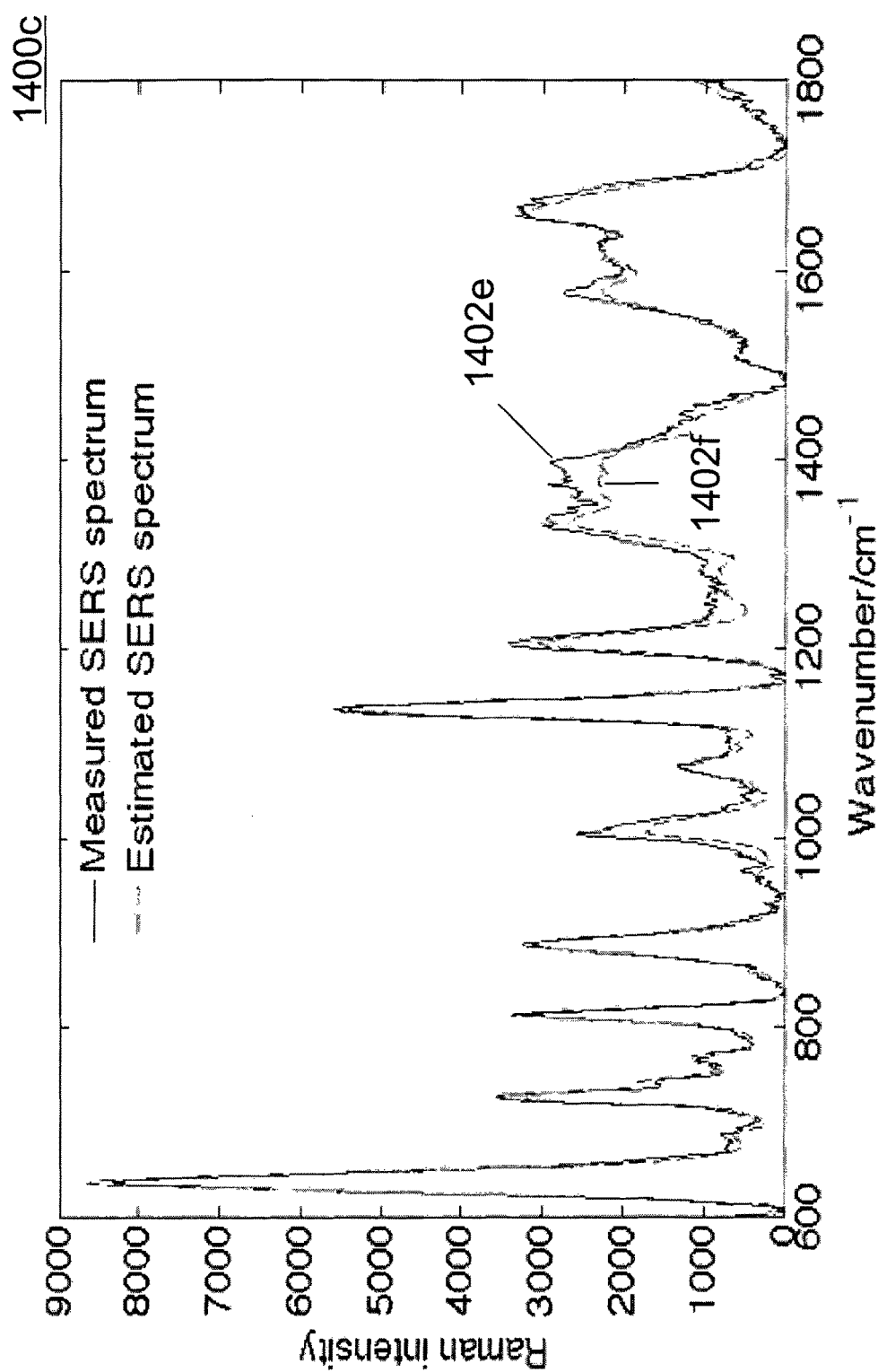
FIG. 14C is a plot of intensity (arbitrary units) against wavenumber (cm$^{-1}$) illustrating measured surface enhanced Raman spectroscopy (SERS) spectrum and the surface enhanced Raman spectroscopy (SERS) spectrum reconstructed by traditional Wiener estimation for the worst case using the best combination of six non-negative principal components (PCs) based filters.
Figure 14D:
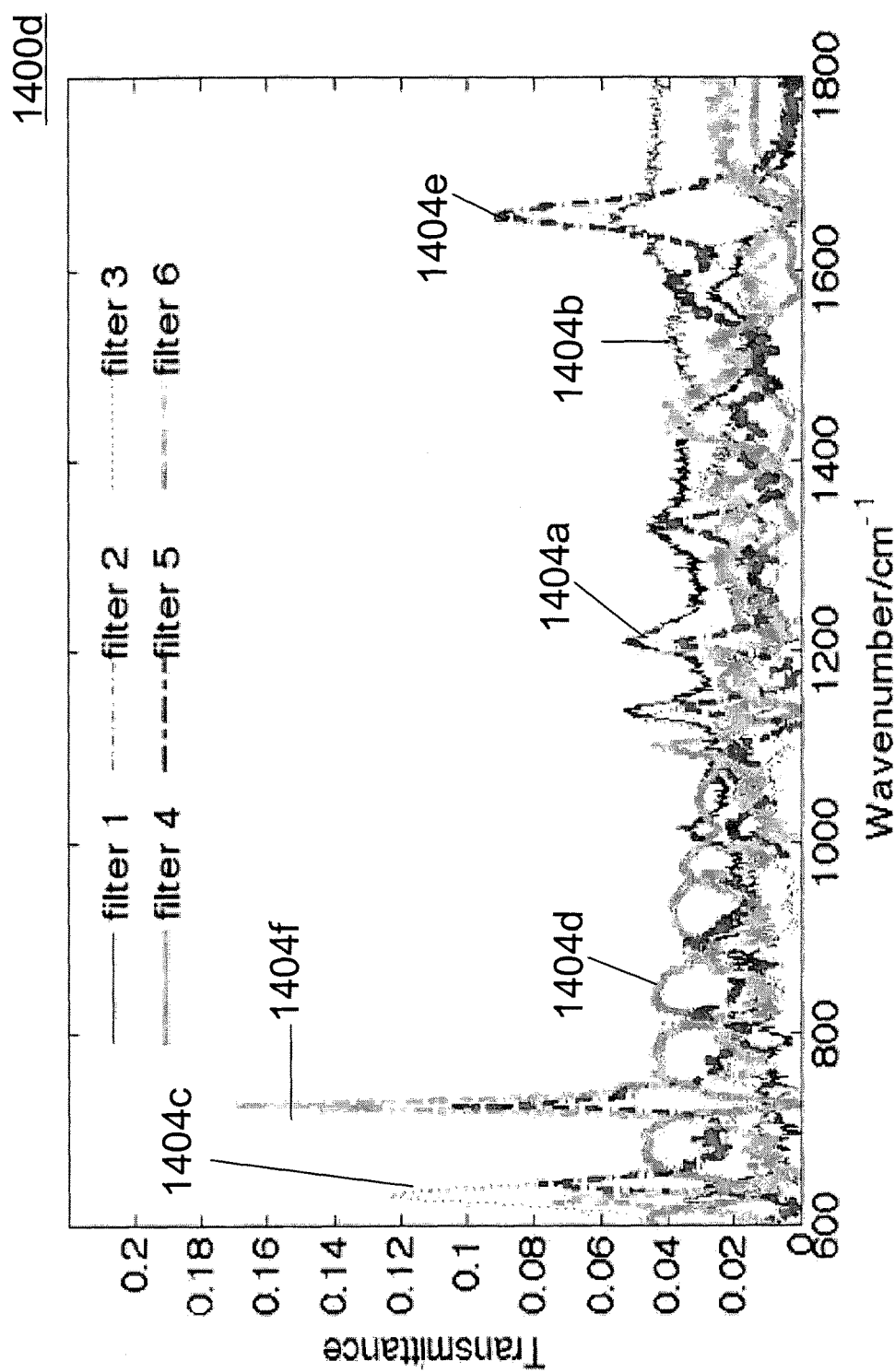
FIG. 14D is a plot of intensity (arbitrary units) against wavenumber (cm$^{-1}$) illustrating the transmittance spectra of the six non-negative principal components (PCs) based filters corresponding to the typical case.

FIG. 14A is a plot 1400a of intensity (arbitrary units) against wavenumber ($cm^{-1}$) illustrating measured surface enhanced Raman spectroscopy (SERS) spectrum and the surface enhanced Raman spectroscopy (SERS) spectrum reconstructed by traditional Wiener estimation for the best case using the best combination of six non-negative principal components (PCs) based filters. 1402a indicates the measured surface enhanced Raman spectroscopy (SERS) spectrum while 1402b indicates the reconstructed spectrum. FIG. 14B is a plot 1400b of intensity (arbitrary units) against wavenumber ($cm^{-1}$) illustrating measured surface enhanced. Raman spectroscopy (SERS) spectrum and the surface enhanced Raman spectroscopy (SERS) spectrum reconstructed by traditional Wiener estimation for a typical case using the best combination of six non-negative principal components (PCs) based filters. 1402c indicates the measured surface enhanced Raman spectroscopy (SERS) spectrum while 1402d indicates the reconstructed spectrum. FIG. 14C is a plot 1400c of intensity (arbitrary units) against wavenumber ($cm^{-1}$) illustrating measured surface enhanced Raman spectroscopy (SERS) spectrum and the surface enhanced Raman spectroscopy (SERS) spectrum reconstructed by traditional Wiener estimation for the worst case using the best combination of six non-negative principal components (PCs) based filters. 1402e indicates the measured surface enhanced Raman spectroscopy (SERS) spectrum while 1402f indicates the reconstructed spectrum. FIG. 14D is a plot 1400d of intensity (arbitrary units) against wavenumber ($cm^{-1}$) illustrating the transmittance spectra of the six non-negative principal components (PCs) based filters corresponding to the typical case. 1404a represents the transmittance spectra of the first filter, 1404b represents the transmittance spectra of the second filter, 1404c represents the transmittance spectra of the third filter, 1404d represents the transmittance spectra of the fourth filter, 1404e represents the transmittance spectra of the fifth filter and 1404f represents the transmittance spectra of the sixth filter. The fluorescence background has been removed in both sets of spectra (measured surface enhanced Raman spectroscopy (SERS) spectrum and the surface enhanced Raman spectroscopy (SERS) spectrum reconstructed by traditional Wiener estimation) to facilitate comparison in Raman features.

FIGS. 14A-C show the comparison between the measured SERS spectra and the SERS spectra reconstructed by traditional Wiener estimation with the first six non-negative PCs based filters. The relative RMSEs were $8.5 \times 10^{-3}$, $1.44 \times 10^{-2}$, $2.85 \times 10^{-2}$ in the best case, the, typical case and the worst case, respectively.

It has been demostrated that full Raman spectra may be reconstructed by Wiener estimation from a few narrow-band measurements in the presence of fluorescence background. The experiment has proved the feasibility of applying reconstruction based on a plurality of narrow-band measurements by Wiener estimation, enabling fast Raman imaging using a simple Raman setup.

For SERS spectra, Gaussian filters and commercial filters showed worse accuracies compared with PCs based filters. This may be attributed to the ability of PCs based filter to capture more variance, i.e. information, compared with Gaussian filters and commercial filters. In addition, the importance of capturing both Raman signal and fluorescence background information have also been verified. SERS spectra generated from the Raman signal or fluorescence background alone using PCs based filters have been tested. For SERS spectra generated from Raman signal using PCs based filters, the relative RMSEs were $4.57\times10^{-2}$, $4.47\times10^{-2}$, $3.28\times10^{-2}$ and $3.02\times10^{-2}$ for three, four, five and six filters, respectively. For SERS spectra generated from fluorescence background using PCs based filters, the relative RMSEs were $2.40\times10^{-2}$, $2.33\times10^{-2}$, $2.14\times10^{-2}$ and $2.03\times10^{-2}$ for three, four, five and six filters, respectively. Both sets of relative RMSEs were considerably greater than those obtained using PCs based filters generated from Raman spectra with fluorescence background as shown in Table 5, which implies that information from both Raman signal and fluorescence background is important for reconstruction.

For spontaneous Raman spectra, the mean values of reconstruction accuracy using Gaussian filters and commercial filters were better than PCs based filters when only three or four filters were used. This may be attributed to the fluorescence background much larger in spontaneous Raman spectra compared to that in SERS spectra. In this case, the variance for fluorescence background in a spontaneous Raman spectrum was considerably larger than the Raman signal in magnitude. Based on the characteristics of PCA, the first three or four PCs, from which the transmittance spectra of these PCs based filters were derived, capture most information from smooth fluorescence background and less information from the Raman signal on top of the fluorescence background. Interestingly, PCs based filters showed better reconstruction accuracy than Gaussian filters and commercial filters when five or six filters were used. Moreover, the improvement in accuracy for PCs based filters from four to five filters was significant, which means that more information about Raman signal was collected by the additional PCs based filters as sufficient information about fluorescence background has been collected by the first four PCs based filters. Spontaneous Raman spectra were also generated from the Raman signal or fluorescence background alone using PCs based filters. For spontaneous Raman spectra generated from the Raman signal using PCs based filters, the relative RMSEs were $1.43\times10^{-1}$, $1.43\times10^{-1}$, $5.60\times10^{-2}$ and $5.42\times10^{-2}$ for three, four, five and six filters, respectively. For spontaneous Raman spectra generated from fluorescence background using PCs based filters, the relative RMSEs were $8.86\times10^{-2}$, $8.28\times10^{-2}$, $9.69\times10^{-2}$ and $8.12\times10^{-2}$ for three, four, five and six filters, respectively. These values were much larger than those obtained using PCs based filters generated from Raman spectra with fluorescence background as shown in Table 4. This further shows the importance of deriving optimal filters from both Raman signal and fluorescence background.

For both spontaneous Raman spectra and SERS spectra, additional filters may improve the reconstruction accuracy significantly. Therefore, a tradeoff between the accuracy and cost needs to be made in the choice of number of filters. Compared with spontaneous Raman spectra, the reconstruction accuracy of SERS spectra was much better when the same number of filters were used as shown in Tables 4 and 5. This observation could be explained by two factors. One is that SERS spectra may contain smaller fluorescence background than spontaneous Raman spectra, which lowers down the requirement on the effectiveness of the filter set in capturing most information. The other is that SERS spectra may exhibit higher signal-to-noise ratio, which reduces the influence of noise on reconstruction. Using sophisticated methods, e.g. shifted excitation Raman difference spectroscopy, Fourier transformed Raman spectroscopy, and temporal gating, to suppress fluorescence background and/or improve the signal-to-noise ratio of Raman signals would further improve the reconstruction accuracy.

Table 6 compares the relative RSME of spontaneous Raman spectra (after fluorescence background removed) reconstructed from narrow-band measurements with the best combination of three filters using traditional Wiener estimation and between modified Wiener estimation.

TABLE 6

| | Commercial filters | Gaussian filters | PCs based filters | Non-negative PCs based filters |
|---|---|---|---|---|
| Traditional Wiener estimation | $5.61 \times 10^{-2}$ | $5.18 \times 10^{-2}$ | $6.93 \times 10^{-2}$ | $6.93 \times 10^{-2}$ |
| Modified Wiener estimation | $4.82 \times 10^{-2}$ | $4.55 \times 10^{-2}$ | $6.99 \times 10^{-2}$ | $7.13 \times 10^{-2}$ |

Table 7 compares the relative RSME of SERS spectra (after fluorescence background removed) reconstructed from narrow-band measurements with the best combination of three filters using traditional Wiener estimation and between modified Wiener estimation.

TABLE 7

| | Commercial filters | Gaussian filters | PCs based filters | Non-negative PCs based filters |
|---|---|---|---|---|
| Traditional Wiener estimation | $2.65 \times 10^{-2}$ | $2.64 \times 10^{-2}$ | $2.13 \times 10^{-2}$ | $2.13 \times 10^{-2}$ |
| Modified Wiener estimation | $2.54 \times 10^{-2}$ | $2.61 \times 10^{-2}$ | $2.14 \times 10^{-2}$ | $2.15 \times 10^{-2}$ |

In addition, the method of modified Wiener estimation developed previously have been compared to traditional Wiener estimation for both spontaneous Raman spectra and SERS spectra as shown in Tables 6 and 7. For spontaneous Raman spectra shown in Table, there were reduction in percentage values of 14.1% and 12.2% in the relative RMSE for commercial filters and Gaussian filters when using modified Wiener estimation compared with the traditional Wiener estimation. In contrast, there was small degradation in reconstruction accuracy from traditional Wiener estimation to modified Wiener estimation for PCs based filters and non-negative PCs based filters.

These observations may be explained as below. In modified Wiener estimation, although additional information was provided by using synthesized narrow-band measurements, error was also induced with the correction process. The final reconstruction accuracy was a compromise between the gain (the additional information) and the loss (the induced error). For commercial and Gaussian filters, the additional filters created in the modified Wiener estimation were the first three PCs based filters. In contrast, the additional filters were the fourth to sixth PCs based filters for PCs based filters and non-negative PCs based filters because the first three PCs filters have been applied. The first three PCs based filters with relatively smooth shapes were likely to capture additional information (mainly from slow changing fluorescence background), which outweighed the error induced (mainly from sharp Raman signals) in the correction process. In comparison, the fourth to sixth PCs based filters with sharp peaks were likely to induce larger errors in the correction process because it can only capture additional information mainly from similarly sharp Raman peaks, which were more difficult to correct. For SERS spectra, which contained much weaker fluorescence background than the spontaneous Raman spectra, shown in Table 7, there was no considerable difference in terms of the relative RMSE between modified Wiener estimation and traditional Wiener estimation. Therefore, the method of modified Wiener estimation may show more significant advantage over traditional Wiener estimation in Raman spectra with intense fluorescence background.

In practice, a new Wiener matrix may need to be constructed with a new set of the calibration data when using a different type of sample. While this may be the major limitation for this method, this method may still find a large number of biomedical applications, such as differentiation of cancer from normal samples and classification of cell death mode etc. Most popular methods for such applications rely on multi-variate statistical analysis, thus also requiring a set of data for training the classifier.

This method of reconstruction may be advantageous when employed in Raman imaging. Currently, most Raman imaging techniques use point scanning or line scanning, in which every scan would involve the acquisition of Raman intensity at many wavenumbers. While wide-field Raman imaging using a CCD may be performed at each wavenumber, this may require a filter with extremely narrow pass band and tunable central wavelength. Moreover, it may be very time consuming given the number of wavenumbers involved (hundreds to thousands depending on spectral resolution required). Various embodiments may require only a few narrow-band filters with much larger bandwidths to get a few Raman images and the full Raman spectrum at each pixel may be reconstructed. The potential improvement in the speed may be dramatic just considering the difference in the number of Raman images required between traditional Raman imaging and the proposed strategy.

The experiment has demonstrated a spectral reconstruction method based on Wiener estimation applied to the narrow-band Raman measurements with fluorescence background for reconstructing the Raman spectra with high spectral resolution. The reconstruction method has been evaluated on both spontaneous Raman data and SERS data. A genetic algorithm was used to identify the optimal combination of different number and types of filters for spectral construction. The agreement between reconstructed spectra and measured spectra was excellent in either set of data, which indicates that this method may be applied to both spontaneous Raman measurements and SERS measurements that involve most Raman spectroscopy based applications. The reconstruction of SERS spectra showed even better results, which demonstrates that the higher signal to noise ratio and lower fluorescence background may improve the reconstruction accuracy. For both spontaneous Raman spectra and SERS spectra, the reconstruction accuracy may be improved significantly by using additional filters and information from both Raman signal and fluorescence background is important. Compared to our previous study, the new results suggest that the proposed method may be used in a simple Raman system that acquires Raman spectra with fluorescence background. Therefore, this method may open a new avenue for Raman imaging to investigate fast changing phenomena in biomedical applications in a simple optical setup without the function of fluorescence suppression.

FIG. 15 is a schematic 1500 illustrating a method of operating a device for determining a condition of an organ of either a human or an animal according to various embodiments. The method may include, in 1502, activating a switching mechanism to switch between an optical examination mode and a Raman mode. During the optical examination mode, a lens system may be configured to direct a first light emitted from a first optical source. During the Raman mode, the lens system may be configured to direct a second light emitted from a second optical source. Further, during the Raman mode, the lens systems may be further configured to direct a third light to the detector.

In other words, the method may include switching between an optical examination mode and a Raman mode. The lens systems may be configured to direct a first light emitted from a first optical source during the optical examination mode. The lens system may be configured to direct a second light emitted from a second optical source during the Raman mode.

The first light emitted from the first optical source may incident on an organ such as an eye. A fourth light may be reflected from the organ when the first light is incident on the organ. The fourth light may be derived from the first light.

The second light emitted from the second optical source may incident on the organ. The third light may be reflected from the organ when the second light is incident on the organ. The third light may be derived from the second light. Raman analysis may be based on the second light and third light.

A method of diagnosing an organ such as the eye may also be provided. The method may include activating a switching mechanism to switch to an optical examination mode so that a first light may be emitted from a first optical source, such as a non-coherent light source, to the organ and detecting a disease or anomaly of the organ (by an observer such as a doctor or an optometrist) based on a second light reflected from the organ. The method may further include activating the switching mechanism to switch to a Raman examination mode so that a second light may be emitted from a second optical source and detecting (via a detector) a third light reflected from the organ.

A method of operating a device may also be provided. The method may include activating a switching mechanism to switch between an optical examination mode and a Raman mode. During the optical examination mode, a lens system may be configured to direct a first light emitted from a first optical source. During the Raman mode, the lens system may be configured to direct a second light emitted from a second optical source. Further, during the Raman mode, the lens systems may be further configured to direct a third light to the detector.

During the optical examination mode, a lens system may be configured to direct the first light emitted from the first optical source to an interface portion.

The lens system during the optical examination mode may be further configured to direct a fourth light, the fourth light derived from the first light, from the interface portion to an optical examination output portion.

The lens system during the Raman mode may be configured to direct the second light emitted from the second optical source to the interface portion.

The lens system during the Raman mode may be configured to direct the third light from the interface to a detector.

The third light may be derived from the second light. The fourth light may be derived from the first light.

In various embodiments, a use of a device may be provided. In various embodiments, a use of a device for determining a condition of an organ of either a human may be provided. The method may include activating a switching mechanism to switch between an optical examination mode and a Raman mode. During the optical examination mode, a lens system may be configured to direct a first light emitted from a first optical source. During the Raman mode, the lens system may be configured to direct a second light emitted from a second optical source. Further, during the Raman mode, the lens systems may be further configured to direct a third light to the detector.

Figure 16:
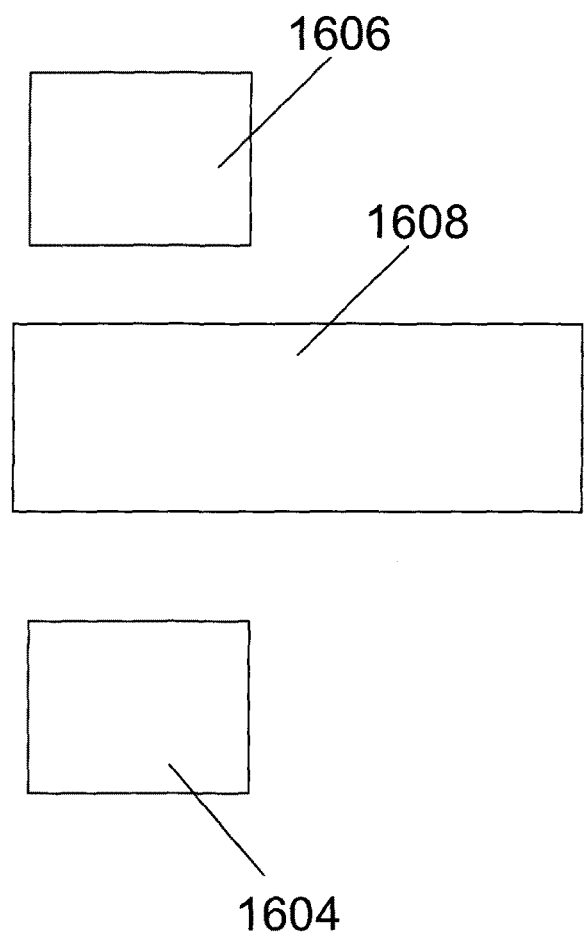
FIG. 16 is a schematic of a device for determining a condition of an organ of either a human or an animal according to various embodiments.

FIG. 16 is a schematic 1600 of a device for determining a condition of an organ of either a human or an animal according to various embodiments. The device may include an optical source 1604, a detector 1606 and a lens system 1608. The lens system 1608 may be configured to direct a light emitted from the optical source 1604. The lens system 1608 may be further configured to direct a further light to the detector 1608. The further light may be based on or derived from the light. The further light may be the light reflected by the light incident on the organ. The lens system 1608 may be configured to direct the light to the organ. The further light reflected from the organ may be directed by the lens system 1608 to the detector 1606.

In various embodiments, the device illustrated in FIG. 1 may only include the components for Raman mode. The components in the device shown in FIG. 16 may work in a similar manner as the Raman components in the device shown in FIG. 1.

The lens system 1608 may include an objective lens for focusing the light. The lens system 1608 may further include an actuator, e.g. a piezoelectric transducer, for controlling a position of the objective lens. The lens system 1608 may include an actuator feedback circuit coupling the detector to the actuator.

The actuator feedback circuit may be configured to receive an output from the detector 1606 and further configured to provide a feedback to the actuator based on the output from the detector 1606. The actuator feedback circuit may be configured to determine a focus index based on the output from the detector 1606 and further configured to provide a feedback based on the determined focus index and a reference focus index.

The lens system may include a spatial light modulator (or another dynamic optical element such as a digital micromirror) for modulating the light emitted from the optical source reflected. The lens system may include a spatial light modulator feedback circuit (or dynamic optical element feedback circuit) coupling the detector 1606 to the spatial light modulator or dynamic optical element. The spatial light modulator feedback circuit (or dynamic optical element feedback circuit) may be configured to generate a skeletonized line based on a line formed by the light. The spatial light modulator (or dynamic optical element feedback circuit) may be configured to be adjusted based on a feedback from the spatial light modulator feedback circuit (or dynamic optical element feedback circuit) until a focus index of each pixel along a subsequent skeletonized line generated reaches a maximum value. In other words, the lens system may include a dynamic optical element for modulating the light emitted from the optical source reflected (to the organ). The dynamic optical element may be a spatial light modulator (SLM) or a digital micromirror device. The lens system may further include a dynamic optical element feedback circuit coupling the detector to the dynamic optical element. The dynamic optical element feedback circuit may be configured to generate a skeletonized line based on a line formed by the light.

The lens system 1608 may include a single beam splitter or a single dichroic mirror configured to direct the light (and/or direct the further light). The device may further include a processor coupled to the detector 1606.

The device may include one or more filters configured to generate one or more narrow-band Raman images from an image captured by the detector 1606. The processor may be configured to generate one or more reconstructed Raman images based on the one or more narrow Raman images, each of the one or more reconstructed Raman images corresponding to one wavelength. The processor may be further configured to generate a Raman spectrum at each pixel based on the one or more reconstructed Raman images. The one or more filters may be configured to generate one or more reference narrow-band Raman images from one or more reference images that contain full spectral information at each pixel for all pixels. The processor may be configured to determine a Wiener matrix based on the one or more reference narrow-band Raman images and the one or more reference images. The one or more reference images may be generated based on one or more reference samples, each reference sample including one or more basic biochemical components. The processor may be configured to generate the one or more reconstructed Raman images based on the one or more narrow-band Raman images and the Wiener matrix. The processor may be configured to remove fluorescence background from the one or more reconstructed Raman images. The one or more narrow-band Raman images may have a spectral resolution lower than the one or more reconstructed Raman images. The one or more filters may be generated from one or more principal components based on Raman spectra of the reference samples.

The device may have an interface portion. The lens system 1608 may be configured to direct the light emitted from the optical source 1604 to the interface portion. The lens system 1608 may be configured to direct the light from the interface portion to the detector 1606. The further light may have a frequency shift from the light. In other words, the frequencies of the light and the further light may be different.

The optical source 1604 may be a laser source.

Methods described herein may further contain analogous features of any structure, device or array described herein. Correspondingly, structures, devices or arrays described herein may further contain analogous features of any method described herein.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A device for determining a condition of an organ of either a human or an animal, the device comprising:
    a first optical source;
    a second optical source;
    a detector;
    a lens system;
    a switching mechanism configured to switch between an optical examination mode and a Raman mode;
    a processor coupled to the detector; and
    one or more filters configured to generate one or more narrow-band Raman images from an image captured by the detector, wherein:

the lens system during the optical examination mode is configured to direct a first light emitted from the first optical source;

the lens system during the Raman mode is configured to direct a second light emitted from the second optical source;

the lens systems during the Raman mode is further configured to direct a third light to the detector;

the processor is configured to generate one or more reconstructed Raman images based on the one or more narrow Raman images, each of the one or more reconstructed Raman images corresponding to a respective wavelength of a plurality of wavelengths; and the processor is further configured to generate a Raman spectrum at each pixel based on the one or more reconstructed Raman images.

2. The device according to claim 1, wherein the lens system comprises:
an objective lens for focusing the second light; and
an actuator configured to control a position of the objective lens.

3. The device according to claim 2, wherein:
the lens system further comprises an actuator feedback circuit coupling the detector to the actuator; and
the actuator feedback circuit is configured to receive an output from the detector and provide a feedback to the actuator based on the output from the detector.

4. The device according to claim 3, wherein the actuator feedback circuit is configured to determine a focus index based on the output from the detector and further configured to provide a feedback based on the determined focus index and a reference focus index.

5. The device according to claim 1, wherein the lens system comprises:
a dynamic optical element for modulating the second light emitted from the second optical source reflected; and
a dynamic optical element feedback circuit coupling the detector to the dynamic optical element, wherein the dynamic optical element feedback circuit is configured to generate a skeletonized line based on a line formed by the second light.

6. The device according to claim 5, wherein the dynamic optical element is configured to be adjusted based on a feedback from the dynamic optical element feedback circuit until a focus index of each pixel along a subsequent skeletonized line generated reaches a maximum value.

7. The device according to claim 1, wherein the lens system comprises one or more beam splitters configured to direct the first light during the optical examination mode and further configured to direct the second light during the Raman mode.

8. The device according to claim 1,
wherein the one or more filters is configured to generate one or more reference narrow-band Raman images from one or more reference images that contain full spectral information at each pixel for all pixels; and
wherein the processor is configured to determine a Wiener matrix based on the one or more reference narrow-band Raman images and the one or more reference images.

9. The device according to claim 8, wherein the one or more reference images are generated based on one or more reference samples, each reference sample comprising one or more basic biochemical components.

10. The device according to claim 8, wherein the processor is configured to generate the one or more reconstructed Raman images based on the one or more narrow-band Raman images and the Wiener matrix.

11. The device according to claim 1, further comprising:
an interface portion, wherein the lens system during the optical examination mode is configured to direct the first light emitted from the first optical source to the interface portion.

12. The device according to claim 11, further comprising:
an optical examination output portion;
wherein the lens system during the optical examination mode is further configured to direct a fourth light, the fourth light derived from the first light, from the interface portion to the optical examination output portion.

13. The device according to claim 12, wherein the lens system during the Raman mode is configured to direct the second light emitted from the second optical source to the interface portion and direct the third light from the interface portion to the detector.

14. The device according to any of claim 1, wherein:
the first optical source is an incoherent light source;
the second optical source is a laser source; and
the third light is derived from the second light.

15. A method of operating a device for determining a condition of an organ of either a human or an animal, the device comprising a first optical source; a second optical source; a detector; a lens system; a switching mechanism configured to switch between an optical examination mode and a Raman mode; a processor coupled to the detector; and one or more filters configured to generate one or more narrow-band Raman images from an image captured by the detector, the method comprising:
activating the switching mechanism to switch between the optical examination mode and the Raman mode, wherein:
during the optical examination mode, the lens system is configured to direct a first light emitted from the first optical source;
during the Raman mode, the lens system is configured to direct a second light emitted from the second optical source;
during the Raman mode, the lens systems is further configured to direct a third light to the detector;
the processor is configured to generate one or more reconstructed Raman images based on the one or more narrow Raman images, each of the one or more reconstructed Raman images corresponding, to a respective wavelength of a plurality of wavelengths; and
the processor is further configured to generate a Raman spectrum at each pixel based on the one or more reconstructed Raman images.

16. The method according to claim 15, wherein during the optical examination mode, the lens system is configured to direct the first light emitted from the first optical source to an interface portion.

17. The method according to claim 16, wherein the lens system during the optical examination mode is further configured to direct a fourth light, the fourth light derived from the first light, from the interface portion to an optical examination output portion.

18. The method according to claim 15, wherein the lens system during the Raman mode is configured to direct the second light emitted from the second optical source to the interface portion and direct the third light from the interface to the detector.

* * * * *